US012241068B2

(12) United States Patent
Pulé et al.

(10) Patent No.: US 12,241,068 B2
(45) Date of Patent: Mar. 4, 2025

(54) CD79-SPECIFIC CHIMERIC ANTIGEN RECEPTOR

(71) Applicant: AUTOLUS LIMITED, London (GB)

(72) Inventors: Martin Pulé, London (GB); Shaun Cordoba, London (GB); Simon Thomas, London (GB); Shimobi Onuoha, London (GB); Mathieu Ferrari, London (GB)

(73) Assignee: AUTOLUS LIMITED, London (GB)

(*) Notice: Subject to any disclaimer, the term of this patent is extended or adjusted under 35 U.S.C. 154(b) by 1113 days.

(21) Appl. No.: 17/055,387

(22) PCT Filed: May 15, 2019

(86) PCT No.: PCT/GB2019/051331
§ 371 (c)(1),
(2) Date: Nov. 13, 2020

(87) PCT Pub. No.: WO2019/220110
PCT Pub. Date: Nov. 21, 2019

(65) Prior Publication Data
US 2022/0273710 A1    Sep. 1, 2022

(30) Foreign Application Priority Data

May 15, 2018    (GB) ...................................... 1807870

(51) Int. Cl.
| | | |
|---|---|---|
| C07K 16/28 | (2006.01) | |
| A61K 39/00 | (2006.01) | |
| A61P 35/00 | (2006.01) | |
| C07K 14/725 | (2006.01) | |
| C12N 5/0783 | (2010.01) | |
| C12N 15/62 | (2006.01) | |
| C12N 15/86 | (2006.01) | |
| A61K 38/00 | (2006.01) | |

(52) U.S. Cl.
CPC ........ *C12N 15/625* (2013.01); *A61K 39/4611* (2023.05); *A61K 39/4631* (2023.05); *A61K 39/464411* (2023.05); *A61K 39/464412* (2023.05); *A61K 39/464413* (2023.05); *A61P 35/00* (2018.01); *C07K 14/7051* (2013.01); *C07K 16/2803* (2013.01); *C12N 5/0636* (2013.01); *C12N 15/86* (2013.01); *A61K 38/00* (2013.01); *A61K 2239/13* (2023.05); *A61K 2239/31* (2023.05); *C12N 2740/10043* (2013.01)

(58) Field of Classification Search
None
See application file for complete search history.

(56) References Cited

U.S. PATENT DOCUMENTS

| | | |
|---|---|---|
| 7,052,906 B1 | 5/2006 | Lawson et al. |
| 10,457,730 B2 | 10/2019 | Pule et al. |
| 2016/0296562 A1 | 10/2016 | Pule et al. |
| 2016/0362472 A1 | 12/2016 | Bitter et al. |
| 2017/0051308 A1 | 2/2017 | Morgan et al. |
| 2018/0044417 A1 | 2/2018 | Pule et al. |
| 2019/0038672 A1 | 2/2019 | Pule et al. |
| 2019/0177412 A1 | 6/2019 | Onuoha et al. |
| 2019/0330337 A1 | 10/2019 | Pule et al. |
| 2020/0140544 A1 | 5/2020 | Pule et al. |

FOREIGN PATENT DOCUMENTS

| | | |
|---|---|---|
| WO | WO-2015/075468 A1 | 5/2015 |
| WO | WO-2015/075469 A1 | 5/2015 |
| WO | WO-2015/075470 A1 | 5/2015 |
| WO | WO-2015/142675 A2 | 9/2015 |
| WO | WO-2016/102965 A1 | 6/2016 |
| WO | WO-2016/139487 A1 | 9/2016 |
| WO | WO-2016/151315 A1 | 9/2016 |
| WO | WO-2016/164731 A2 | 10/2016 |
| WO | WO-2017/009474 A1 | 1/2017 |
| WO | WO-2017/172981 A2 | 10/2017 |
| WO | WO-2017/216561 A1 | 12/2017 |
| WO | WO-2017/216562 A1 | 12/2017 |
| WO | WO-2018/226958 A1 | 12/2018 |
| WO | WO-2019/220109 A1 | 11/2019 |

OTHER PUBLICATIONS

U.S. Appl. No. 17/084,535, filed Oct. 29, 2020.
U.S. Appl. No. 17/054,670, filed Nov. 11, 2020.
Donnelly et al., "The 'cleavage' activities of foot-and-mouth disease virus 2A site-directed mutants and naturally occurring '2A-like' sequences," J. Gen. Virol. 82:1027-1041 (2001).
Dornan et al., "Therapeutic potential of an anti-CD79b antibody-drug conjugate, anti-CD79b-vc-MMAE, for the treatment of non-Hodgkin lymphoma," Blood 114(13):2721-2729 (2009).
Fry et al., "CD22-CAR T Cells Induce Remissions in CD19-CAR Naive and Resistant B-ALL," Nat Med 24(1):20-28 (2018).
International Search Report and Written Opinion from International Application No. PCT/GB2019/051331 dated Aug. 1, 2019.
Palanca-Wessels et al., "Safety and activity of the anti-CD79B antibody-drug conjugate polatuzumab vedotin in relapsed or refractory B-cell non-hodgkin lymphoma and chronic lymphocytic leukaemia: a phase 1 study," Lancet oncol 16:704-715 (2015).
Polson et al., "Antibody-drug conjugates targeted to CD79 for the treatment of non-Hodgkin lymphoma," Blood 110:616-23 (2007).
Ruella et al., "Dual CD19 and CD123 targeting prevents antigen-loss relapses after CD19-directed immunotherapies," Journal of Clinical Investigation, 126(10):3814-3826 (2016).
Schneider et al., "A tandem CD19/CD20 CAR lentiviral vector drives on-target and off-target antigen modulation in leukemia cell lines," Journal for ImmunoTherapy of Cancer 5(1):17 pages (2017).

(Continued)

*Primary Examiner* — Meera Natarajan
*Assistant Examiner* — Cheom-Gil Cheong
(74) *Attorney, Agent, or Firm* — MARSHALL, GERSTEIN & BORUN LLP

(57) ABSTRACT

The present invention provides a chimeric antigen receptor (CAR) which specifically binds CD79 as well as a nucleic acid sequence and a vector encoding the CAR. It further provides a cell which expresses the CAR at the cell surface.

3 Claims, 7 Drawing Sheets

Specification includes a Sequence Listing.

(56) References Cited

OTHER PUBLICATIONS

Chothia et al., "Canonical Structures for the Hypervariable Regions of Immunoglobulins," Journal of Molecular Biology, 196:901-917 (1987).

Haso et al., "Anti-CD22-Chimeric Antigen Receptors Targeting B Cell Precursor Acute Lymphoblastic Leukemia," Blood, DOI: 10.1182/blood-2012-06-438002, ISSN 0006-4971, 121(7):1165-1174 (2013).

Zah, "T Cells Expressing CD19/CD20 Bispecific Chimeric Antigen Receptors Prevent Antigen Escape by Malignant B Cells," Cancer Immunology Research, 4(6):498-508 (2016).

CD79-SPECIFIC CHIMERIC ANTIGEN RECEPTOR

CROSS-REFERENCE TO RELATED APPLICATIONS

This is a U.S. National Phase of International Application No. PCT/GB2019/051331, filed May 15, 2019, which claims priority to Great Britain Application No. 1807870.9, filed May 15, 2018.

FIELD OF THE INVENTION

The present invention relates to chimeric antigen receptors (CARs) which specifically bind Cluster of Differentiation 79 (CD79). It also relates to cells and agents useful in the treatment of B-cell malignancies.

BACKGROUND TO THE INVENTION

A number of immunotherapeutic agents have been described for use in cancer treatment, including therapeutic monoclonal antibodies (mAbs), immunoconjugated mAbs, radioconjugated mAbs and bi-specific T-cell engagers. Typically these immunotherapeutic agents target a single antigen: for instance, Rituximab targets CD20; Myelotarg targets CD33; and Alemtuzumab targets CD52.

Chimeric antigen receptors are proteins which, in their usual format, graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals.

The most common form of these molecules are fusions of single-chain variable fragments (scFv) derived from monoclonal antibodies which recognise a target antigen, fused via a spacer and a transmembrane domain to a signalling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

The human CD19 antigen is a 95 kDa transmembrane glycoprotein belonging to the immunoglobulin superfamily. CD19 is expressed very early in B-cell differentiation and is only lost at terminal B-cell differentiation into plasma cells. Consequently, CD19 is expressed on all B-cell malignancies apart from multiple myeloma. Since loss of the normal B-cell compartment is an acceptable toxicity, CD19 is an attractive CAR target for B-cell leukemias and lymphomas.

CD19-targeted CAR T-cell therapy has proven effective in the clinic, leading to the recent approvals by the U.S. Food and Drug Administration for CD19 CAR T-cell therapy for the treatment of relapsed/refractory ALL (tisagenlecleucel) and for relapsed/refractory diffuse large B-cell lymphoma (axicabtagene ciloleucel).

A problem with CAR T-cell therapies targeted against CD19 is that the B-cell malignancy may mutate and become CD19-negative. CD19 antigen escape can arise by different mechanisms, including differential splicing, missense mutations or lineage switch. CD19 antigen escape results in relapse with CD19-negative cancers which are not responsive to the therapy. For example, in one paediatric study, Grupp et al. reported that half of all relapses following CD19-targeted chimeric antigen receptor therapy for B-acute Lymphoblastic leukaemia (B-ALL) were due to CD19-negative disease (56th American Society of Hematology Annual Meeting and Exposition).

A similar problem has been observed with CAR-T cell approaches which target the B-cell antigen CD22. CD22, like CD19, is expressed on B-cell malignancies such as B-ALL, and is usually retained following CD19 loss. However, a clinical trial using a CD22 CAR showed that although complete remission was initially seen in 73% of patients, relapses were observed after 6 months associated with diminished CD22 site density. It is thought that reduction in CD22 antigen density permitted CD22+cell escape from killing by CD22 CAR T-cells (Fry et al., 2018, Nat Med 24:20-8). Loss of target antigen is also recognised in diffuse large B-cell lymphoma (DLBCL).

There is thus a need for improved CAR-T cell therapies which are less liable to relapse through antigen escape.

SUMMARY OF ASPECTS OF THE INVENTION

The inventors have developed a CAR which specifically binds CD79, a protein component of the B cell receptor (BCR). Given the dependence of certain B cell malignancies on BCR signalling for survival (Burger & Wiestner, 2018), it is predicted that malignant B cells will be less prone to tumour escape from an anti-CD79 CAR than from an anti-CD19 or anti-CD22 CAR.

Thus, in a first aspect, the present invention provides a chimeric antigen receptor (CAR) which binds CD79.

The CAR may specifically bind CD79A. For example, it may bind the unspliced portion of CD79A ectodomain (residues 33 to 143 of SEQ ID NO: 105).

The CAR may specifically bind CD79B. For example it may bind the unspliced portion of CD79B ectodomain (residues 29 to 159 of SEQ ID NO: 106).

The CAR may comprise an antigen binding domain selected from a scFv, a Fab and a dAb antigen binding domain. The antigen binding domain may be or comprise a Fab, a dAb or an scFv.

The CAR may comprise an antigen-binding domain comprising:

a) a heavy chain variable region (VH) having complementarity determining regions (CDRs) with the following sequences:

```
CDR1-
                        (SEQ ID NO: 113)
GFTFSNAA;

CDR2-
                        (SEQ ID NO: 114)
IRTKPNNYAT

CDR3-
                        (SEQ ID NO: 115)
TYYDGSSYAMDA;
``` and
a light chain variable region (VL) having CDRs with the following sequences:

CDR1- QSLEYSDGYTY; (SEQ ID NO: 116)

CDR2- EVS

CDR3- FQATHDPYT; (SEQ ID NO: 117)

or
b) a VH having CDRs with the following sequences:

CDR1- GFTFSHTA; (SEQ ID NO: 121)

CDR2- IRIQPKNYAT (SEQ ID NO: 122)

CDR3- TAAGFGFDY; (SEQ ID NO: 123)

and
a VL having CDRs with the following sequences:

CDR1- QSLEYSDGNTY; (SEQ ID NO: 124)

CDR2- EVS

CDR3- LQATHDPFT; (SEQ ID NO: 125)

or
c) a VH having CDRs with the following sequences:

CDR1- GFTFSNAA; (SEQ ID NO: 113)

CDR2- IRTKPNNYAT (SEQ ID NO: 114)

CDR3- TADGGYGFDY; (SEQ ID NO: 129)

and
a VL having CDRs with the following sequences:

CDR1- QSLEYSDGYTY; (SEQ ID NO: 116)

CDR2- EVS

CDR3- FQGTHDPYT (SEQ ID NO: 130)

or
d) a VH having CDRs with the following sequences:

CDR1- GFTFSNAA; (SEQ ID NO: 113)

CDR2- IRTKPNNYAT (SEQ ID NO: 114)

CDR3- TYYDGSSYAMDA; (SEQ ID NO: 115)

and
a VL having CDRs with the following sequences:

CDR1- QSLEYSDGYTY; (SEQ ID NO: 116)

CDR2- EIS

CDR3- FQATHDPYT. (SEQ ID NO: 117)

or
e) a VH having CDRs with the following sequences:

CDR1- GFTFSNTA; (SEQ ID NO: 136)

CDR2- IRIQPKNYAT (SEQ ID NO: 122)

CDR3- TAAGFGFDY; (SEQ ID NO: 123)

and
a VL having CDRs with the following sequences:

CDR1- QRLEYSDGNTY; (SEQ ID NO: 137)

CDR2- EVS

CDR3- LQATHDPFT (SEQ ID NO: 125)

or
f) a VH having CDRs with the following sequences:

CDR1- GFTFSSAA; (SEQ ID NO: 141)

CDR2- IRTKPNNYAT (SEQ ID NO: 114)

CDR3- TYYDGSSYAMDA; (SEQ ID NO: 115)

and
a VL having CDRs with the following sequences:

```
CDR1-
                                    (SEQ ID NO: 116)
QSLEYSDGYTY;

CDR2-
EVS

CDR3-
                                    (SEQ ID NO: 117)
FQATHDPYT/
```

The antigen-binding domain may comprise a sequence selected from SEQ ID NO: 120, 128, 133, 135, 140 and 144.

In a second aspect, the present invention provides a cell which expresses a CAR according to the first aspect of the invention.

The cell may co-express a second CAR at the cell surface, which binds an antigen other than CD79. For example, the second CAR may bind CD19 or CD22.

The cell may further express a third CAR at the cell surface, which binds an antigen other than CD79. For example, the third CAR may bind CD19 or CD22.

In a preferred embodiment, the antigen binding domain of the second CAR binds CD19 and the antigen binding domain of the third CAR binds CD22.

In a 3-way OR gate comprising a CAR of the present invention, the antigen binding domain of one CAR may comprise an scFv, the antigen binding domain of another CAR may comprise a dAb, and the antigen binding domain of another CAR may comprise a Fab.

In particular the cell may comprise first, second and third CARs, in which the antigen binding domain of the first CAR binds CD79 and is a dAb; the antigen binding domain of the second CAR binds CD19 and is a scFv, and the antigen binding domain of the third CAR binds CD22 and is a Fab.

In a third aspect the present invention provides a nucleic acid sequence which encodes a CAR according to the first aspect of the invention.

In a fourth aspect there is provided a nucleic acid construct which comprises a first nucleic acid sequence according to the third aspect of the invention and a second nucleic acid sequence which encodes a second CAR as defined above.

The nucleic acid construct according may comprise a third nucleic acid sequence which encodes a third CAR as defined above.

In a fifth aspect, there is provided a vector comprising a nucleic acid sequence according to the third aspect of the invention or a nucleic acid construct according to the fourth aspect of the invention.

In a sixth aspect, there is provided a kit which comprises a first nucleic acid sequence according to the third aspect of the invention, a second nucleic acid sequence as defined in above, and a third nucleic acid sequence as defined above.

In a seventh aspect there is provided a kit comprising:
(i) a first vector which comprises a first nucleic acid sequence according to the third aspect of the invention; and
(ii) a second vector which comprises the second nucleic acid construct as defined above; and, optionally,
(iii) a third vector which comprises the third nucleic acid construct as defined above.

In an eighth aspect, there is provided a method for making a cell according to the second aspect of the invention, which comprises the step of introducing a nucleic acid sequence according to the third aspect of the invention and, optionally, a nucleic acid sequence encoding a second CAR and, optionally, a nucleic acid sequence encoding a third CAR; or a nucleic acid construct according to the fourth aspect of the invention; or a vector according to the fifth aspect of the invention; or a first vector and, optionally, a second vector and, optionally, a third vector as defined above, into a cell.

The cell may be from a sample isolated from a subject.

In a ninth aspect, there is provided a pharmaceutical composition comprising a plurality of cells according to the third aspect of the invention.

In a tenth aspect, there is provided a method for treating and/or preventing a disease, which comprises the step of administering a pharmaceutical composition according to the ninth aspect of the invention to a subject.

The method may comprise the following steps:
(i) isolation of a cell-containing sample from a subject;
(ii) transduction or transfection of the cells following the method according to the eighth aspect of the invention; and
(iii) administering the cells obtained in (ii) to the subject.

In an eleventh aspect, there is provided a pharmaceutical composition according to the ninth aspect of the invention for use in treating and/or preventing a disease.

In a twelfth aspect, there is provided the use of a cell according to the third aspect of the invention in the manufacture of a medicament for treating and/or preventing a disease.

The disease may be a cancer, such as a B-cell leukemia or lymphoma.

DETAILED DESCRIPTION OF THE INVENTION

Figure 1:
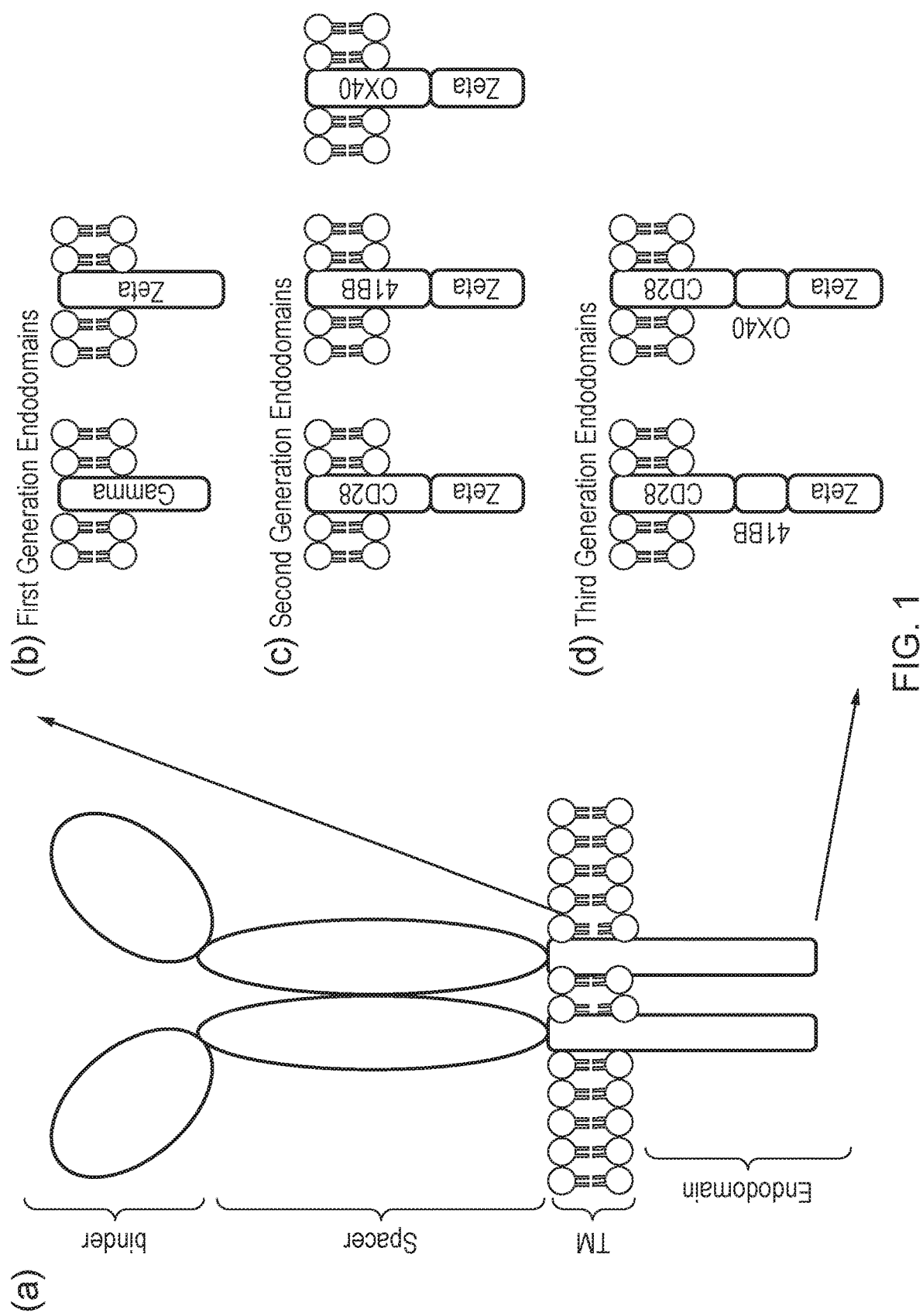
FIG. 1. Overview of chimeric antigen receptors and their endodomains
(a) Basic schema of a chimeric antigen receptor; (b) First generation receptors; (c) Second generation receptors; (d) Third generation receptors.

The present invention relates to a chimeric antigen receptor (CAR) which specifically binds CD79.

1. CD79

The term "CD79" or "Cluster of differentiation 79" refers to the protein at the surface of B cells that encompasses two transmembrane proteins, CD79a and CD79b, which form a disulfide-linked heterodimer and are members of the immunoglobulin (Ig) gene superfamily. The transmembrane CD79a and CD79b proteins couple at the extracellular end with any one of the five different types of transmembrane Ig molecules (IgM, IgD, IgG, IgE, or IgA), which are disulfide-linked proteins composed of two Ig heavy chains and two Ig light chains. This combination of CD79 and immunoglobulin on the B-cell surface forms the B-cell signalling receptor (BCR). The intracytoplasmic domains of CD79a and CD79b contain immunoreceptor tyrosine-based activation motifs (ITAMs) that transmit activation signals to the B-cell upon antigen-induced BCR aggregation.

CD79 expression is restricted to Pre-B cells and mature B cells (excluding plasma cells). CD79 is also expressed on a majority of B-cell-derived malignancies. This narrow expression pattern makes it a promising target for cancer-targeted therapies with minimal targeting to normal tissue.

The term "CD79a" or "CD79A" refers to the B-cell antigen receptor complex-associated protein alpha chain also known as Ig-alpha, MB-1 membrane glycoprotein, membrane-bound immunoglobulin-associated protein, and surface IgM-associated protein. The human isoforms of CD79a are depicted under Accession Nos. P11912.1 (Isoform 1 or long) and P11912.2 (Isoform 2 or short) in the Uniprot database on 20 Apr. 2018.

The term "CD79b" or "CD79B" refers to the B-cell antigen receptor complex-associated protein beta chain also known as Ig-beta, B-cell-specific glycoprotein B29, and immunoglobulin-associated B29 protein. The human isoforms of CD79b are depicted under Accession Nos. P40259-1 (Isoform long), P40259-2 (Isoform short) and P40259-3 (Isoform 3) in the Uniprot database on 20 Apr. 2018.

Activated B lymphocytes have increased amounts of the short or truncated CD79 isoforms. In a particular embodiment, the invention relates to a CAR which specifically binds CD79a. In a preferred embodiment, the CAR binds the unspliced portion or CD79a ectodomain, i.e. residues 33 to 143 of CD79a isoform 1, shown below as SEQ ID NO: 105 (Uniprot Accession No. P11912.1). In another particular embodiment, the invention relates to a CAR which specifically binds CD79b. In another preferred embodiment, the CAR binds the unspliced portion or CD79b ectodomain, i.e. residues 29 to 159 of CD79b isoform long, shown below as SEQ ID NO: 106 (Uniprot Accession No. P40259-1).

```
CD79a isoform 1
                                     SEQ ID NO:NO: 105
MPGGPGVLQALPATIFLLFLLSAVYLGPGCQALWM

HKVPASLMVSLGEDAHFQCPHNSSNNANVTWWRVL

HGNYTWPPEFLGPGEDPNGTLIIQNVNKSHGGIYV

CRVQEGNESYQQSCGTYLRVRQPPPRPFLDMGEGT

KNRIITAEGIILLFCAVVPGTLLLFRKRWQNEKLG
```

```
-continued
LDAGDEYEDENLYEGLNLDDCSMYEDISRGLQGTY

QDVGSLNIGDVQLEKP

Unspliced portion or CD79a ectodomain
(residues 33 to 143 of CD79a isoform 1):
                                     SEQ ID NO: 145
LWMHKVPASLMVSLGEDAHFQCPHNSSNNANVTWW

RVLHGNYTWPPEFLGPGEDPNGTLIIQNVNKSHGG

IYVCRVQEGNESYQQSCGTYLRVRQPPPRPFLDMG

EGTKNR

CD79b isoform 2-
                                     SEQ ID NO:NO: 106
MARLALSPVPSHWMVALLLLLSAEPVPAARSEDRY

RNPKGSACSRIWQSPRFIARKRGFTVKMHCYMNSA

SGNVSWLWKQEMDENPQQLKLEKGRMEESQNESLA

TLTIQGIRFEDNGIYFCQQKCNNTSEVYQGCGTEL

RVMGFSTLAQLKQRNTLKDGIIMIQTLLIILFIIV

PIFLLLDKDDSKAGMEEDHTYEGLDIDQTATYEDI

VTLRTGEVKWSVGEHPGQE

Unspliced portion or CD79b ectodomain
(residues 29 to 159 of CD79b isoform
long):
                                     SEQ ID NO: 146
ARSEDRYRNPKGSACSRIWQSPRFIARKRGFTVKM

HCYMNSASGNVSWLWKQEMDENPQQLKLEKGRMEE

SQNESLATLTIQGIRFEDNGIYFCQQKCNNTSEVY

QGCGTELRVMGFSTLAQLKQRNTLKD
```

2. Chimeric Antigen Receptors

A classical chimeric antigen receptor (CAR) is a chimeric type I trans-membrane protein which connects an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

When the CAR binds the target-antigen, this results in the transmission of an activating signal to the T-cell it is expressed on. Thus the CAR directs the specificity and cytotoxicity of the T cell towards tumour cells expressing the targeted antigen.

CARs typically therefore comprise: (i) an antigen-binding domain; (ii) a spacer; (iii) a transmembrane domain; and (iii) an intracellular domain which comprises or associates with a signalling domain (see FIG. 1).

A CAR may have the general structure:

Antigen binding domain-spacer domain-transmembrane domain-intracellular signalling domain (endodomain).

I.I. Signal Peptide

The CAR of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the SEQ ID NO: 1, 2, 3 or 4 or a variant thereof having 5, 4, 3, 2 or 1 amino acid mutations (insertions, substitutions or additions) provided that the signal peptide still functions to cause cell surface expression of the CAR.

SEQ ID NO: 1:
MGTSLLCWMALCLLGADHADG

The signal peptide of SEQ ID NO: 7 is compact and highly efficient. It is predicted to give about 95% cleavage after the terminal glycine, giving efficient removal by signal peptidase.

SEQ ID NO: 2:
MSLPVTALLLPLALLLHAARP

The signal peptide of SEQ ID NO: 8 is derived from IgG1.

SEQ ID NO: 3:
MAVPTQVLGLLLLWLTDARC

The signal peptide of SEQ ID NO: 9 is derived from CD8.

SEQ ID NO: 4:
METDTLLLWVLLLWVPGSTG

The signal peptide for the first CAR may have a different sequence from the signal peptide of the second CAR (and from the 3$^{rd}$ CAR and 4$^{th}$ CAR etc).

1.2. Antigen Binding Domain

The antigen binding domain is the portion of the CAR which recognises antigen. Numerous antigen-binding domains are known in the art, including those based on the antigen binding site of an antibody. The antibody may be a full-length antibody, a single chain antibody fragment, a F(ab) fragment, a F(ab')$_2$ fragment, a F(ab') fragment, a single domain antibody (sdAb), a VHH/nanobody, a nanobody, an affibody, a fibronectin artificial antibody scaffold, an anticalin, an affilin, a DARPin, a VNAR, an iBody, an affimer, a fynomer, a domain antibody (DAb), an abdurin/nanoantibody, a centyrin, an alphabody, a nanofitin or a D domain which is capable of binding CD79. The antibody may bind CD79a or CD79b.

The antibody or antigen binding domain may be non-human, chimeric, humanised or fully human.

Figure 2:
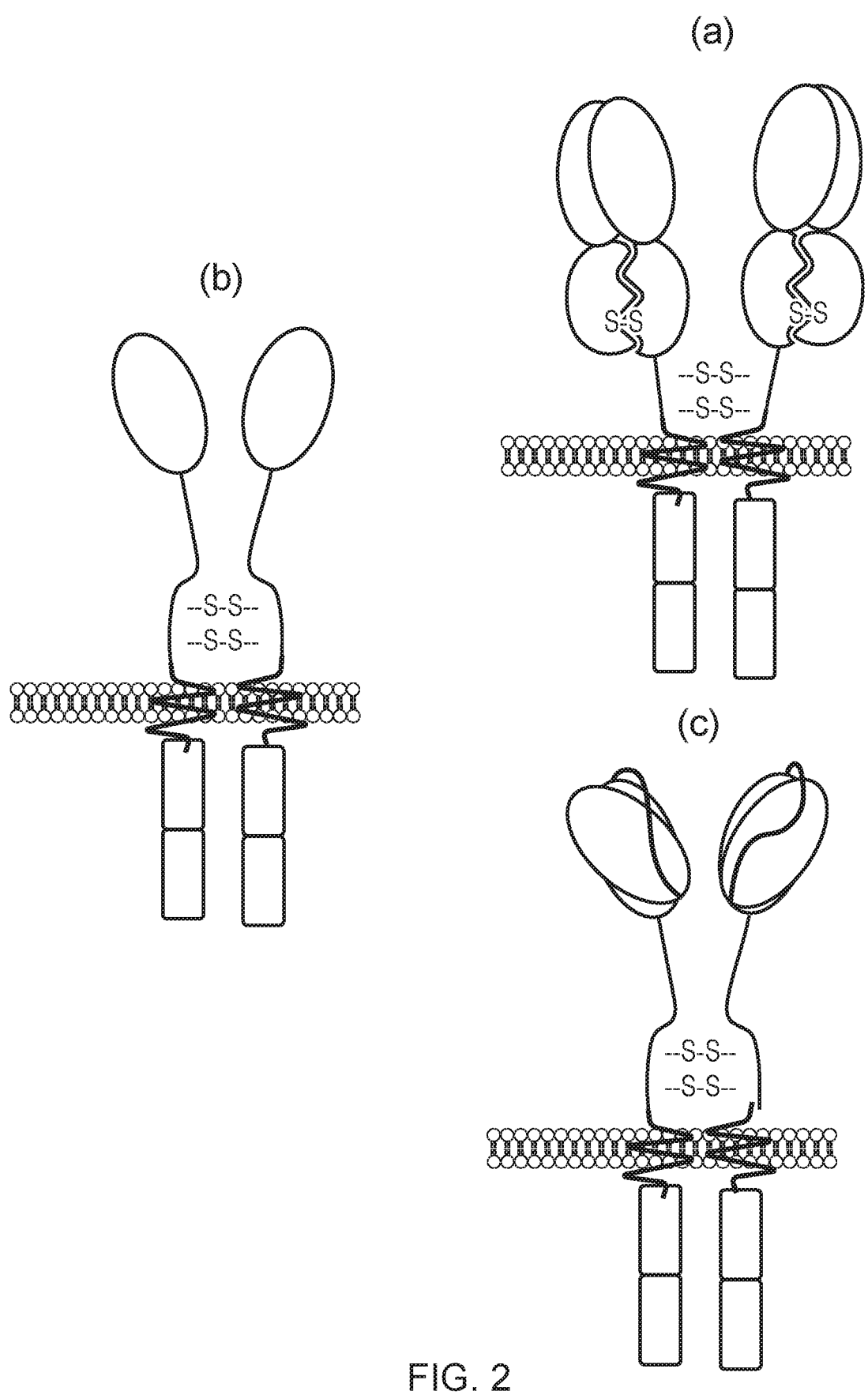
FIG. 2. Different binding domain formats of chimeric antigen receptors
(a) Fab CAR format; (b) dAb CAR format; (c) scFv CAR format.

In a classical CAR, the antigen-binding domain comprises: a single-chain variable fragment (scFv) derived from a monoclonal antibody (see FIG. 2c). CARs may also be produced with a domain antibody (dAb) (see FIG. 2b), or with a Fab (see FIG. 2a).

The CAR of the present invention may comprise an antigen binding domain selected from a scFv, a Fab and a dAb which specifically binds CD79.

A number of anti-CD79 antibodies have been tested in the treatment of B-cell malignancies in a lymphoma xenograft model (Polson et al., 2007, Blood 110:616-23):

| Antibody | Target |
| --- | --- |
| 7H7 | CD79a |
| 15E4 | CD79a |
| 16C11 | CD79a |
| 2F2 | CD79b |
| SN8 | CD79b |

Polson et al., 2007 and Dornan et al., 2009 (Blood 114:2721-9) reported that unconjugated anti-CD79 antibodies are not effective under most circumstances although arming the antibody with drug conjugates proved to be effective in xenograft models.

Antibody 2F2 has been humanised and this humanised version, polatuzumab, is undergoing clinical research as an antibody drug conjugate with monomethyl auristatin E. While limited data are available, Palanca-Wessels et al., 2015 (Lancet Oncol 16:704-15) reported some degree of efficacy in patients with B-cell non-Hodgkin lymphoma (NHL) although grade 3-4 adverse effects were observed in 58% patients treated with polatuzumab vedotin and in 77% patients treated with polatuzumab vedotin combined with rituximab. No objective responses observed in patients with chronic lymphocytic leukaemia (CLL). There is thus a need for improved therapeutic approaches to treat CD79-expressing B-cell malignancies.

There are a number of procedures available in the art for the generation of antigen binding domains, such as scFvs, Fabs and dAbs, with specificity to CD79. Examples include the generation of hybridomas by immunising mice with CD79 or a peptide derived from CD79. Other species may be conveniently immunised for this purpose, including without limitation rats, camelids and sharks. scFvs, Fabs and dAbs are usually generated by PCR cloning of the V-domain and, where Fabs are to be produced, also CH1 and CL repertoire from blood, lymph node, or spleen cDNA obtained from immunised animals. The sequences are cloned into suitable vectors for subsequent protein expression. Animals that may be conveniently immunised for this purpose include, without limitation, mice, rats, rabbits, camelids and sharks. The capacity of the antigen binding domain to bind to CD79 can be determined by a number of assays that are available in the art. Preferably, the binding specificity of monoclonal antibodies produced by a clone of hybridoma cells is determined by immunoprecipitation or by an in vitro binding assay, such as radioimmunoassay (RIA), enzyme-linked immunosorbent assay (ELISA), competitive ELISA, surface plasmon resonance, immunohistochemistry (IHC), or by immunofluorescent techniques such as fluorescence microscopy or flow cytometry.

The person skilled in the art will understand that the amino acid sequences of the antigen binding domains can include one or more amino acid substitutions such that, even though the primary sequence of the polypeptide is altered, the capacity of the antigen binding domain to bind to CD79 is maintained. Said substitution can be a conservative substitution and is generally applied to indicate that the substitution of one amino acid with another amino acid with similar properties (e.g. the substitution of glutamic acid with aspartic acid would be a conservative amino acid substitution).

The CAR of the present invention may comprise a scFv which specifically binds CD79.

A number of anti-CD79 antibodies have been previously described, such as JCB117, SN8, CB3.1, 2F2 (Polatuzumab).

The antigen-binding domain may be the variable regions of each pair of light and heavy chains of an antibody, i.e. the VH and VL domains, respectively, which form its binding site. They are characterised by the same general structure constituted by relatively preserved regions called frameworks (FR) joined by three hyper-variable regions called complementarity determining regions (CDR) (Kabat et al., 1991, Sequences of Proteins of Immunological Interest, 5$^{th}$ Ed., NIH Publication No. 91-3242, Bethesda, MD; Chothia & Lesk, 1987, J Mol Biol 196:901-17). The term "complementarity determining region" or "CDR", as used herein, refers to the region within an antibody that complements an antigen's shape. Thus, CDRs determine the protein's affinity and specificity for specific antigens. The CDRs of the two chains of each pair are aligned by the framework regions, acquiring the function of binding a specific epitope. Consequently, in the case of VH and VL domains both the heavy chain and the light chain are characterised by three CDRs, respectively CDRH1, CDRH2, CDRH3 and CDRL1, CDRL2, CDRL3.

A number of definitions of the CDRs are commonly in use. The Kabat definition is based on sequence variability and is the most commonly used (see www.bioinf.org.uk/abs/). The ImMunoGeneTics information system (IMGT) (see www.imgt.org) can also be used. According to this system, a complementarity determining region (CDR-IMGT) is a loop region of a variable domain, delimited according to the IMGT unique numbering for V domain. There are three CDR-IMGT in a variable domain: CDR1-IMGT (loop BC), CDR2-IMGT (loop C'C"), and CDR3-IMGT (loop FG). Other definitions of the CDRs have also been developed, such as the Chothia, the AbM and the contact definitions (see http://www.imgt.org). The determination of the CDRs according to any of the above definitions can be carried out using a number of methods that are available to the skilled person. Likewise, the skilled person will be able to identify which definition is used for any given set of CDR sequences.

The CDRs may be in the format of a single-chain variable fragment (scFv), which is a fusion protein of the heavy variable region (VH) and light chain variable region (VL) of an antibody, connected with a short linker peptide of ten to about 25 amino acids. The scFvs of the invention may be in the orientation VH-VL, i.e. the VH is at the amino-terminus of the CAR molecule and the VL domain is linked to the spacer and, in turn the transmembrane domain and endodomain, or in the VL-VH orientation.

An anti-CD79 CAR of the present invention may comprise an antigen-binding domain, such as an scFv-type antigen binding domain, derived from one of these anti-CD79 antibodies.

The CD79-binding domain may comprise a) a heavy chain variable region (VH) having complementarity determining regions (CDRs) with the following sequences:

```
CDR1
                                        (SEQ ID NO: 5)
SDYAWN;

CDR2
                                        (SEQ ID NO: 6)
NIWYSGSTTYNPSLKS

CDR3
                                        (SEQ ID NO: 7)
MDF;
``` and b) a light chain variable region (VL) having CDRs with the following sequences:

```
CDR1
                                        (SEQ ID NO: 8)
RASESVDSYGKTFMHWH;

CDR2
                                        (SEQ ID NO: 9)
RVSNLES

CDR3
                                        (SEQ ID NO: 10)
QQSNEDPFT.
```

The anti-CD79 CAR may comprise the following VH sequence:

```
VH sequence from monoclonal antibody
                                        SEQ ID NO: 11
EVQLQESGPGLVKPSQSLSLTCTVTGYSITSDYAWNWI

RQFPGNKLEWMGNIWYSGSTTYNPSLKSRISITRDTSK

NQFFLQLNSVTSEDTATYYCSRMDFWGQGTTLTVSS
```

The anti-CD79 CAR may comprise the following VL sequence:

```
VL sequence from monoclonal antibody
                                        SEQ ID No 12
DIVLTQSPPSLAVSLGQRATISCRASESVDSYGKTFM

HWHQQKPGQPPKLLIYRVSNLESGIPARFSGSGSRTD

FTLTINPVEADDVATYYCQQSNEDPFTFGGGTKLEIK

R
```

The anti-CD79 CAR may comprise the following scFv sequence:

```
(mouse anti-cynomolgus (Macaca fascicularis)
CD79b 10D10 scFv)
                                  SEQ ID NO: 13
DIVLTQSPPSLAVSLGQRATISCRASESVDSYGKTFMH

WHQQKPGQPPKLLIYRVSNLESGIPARFSGSGSRTDF

TLTINPVEADDVATYYCQQSNEDPFTFGGGTKLEIKRS

GGGGSGGGGSGGGGSGGGGSEVQLQESGPGLVKPSQSL

SLTCTVTGYSITSDYAWNWIRQFPGNKLEWMGNIWYSG

STTYNPSLKSRISITRDTSKNQFFLQLNSVTSEDTATY

YCSRMDFWGQGTTLTVSS
```

Alternatively, the anti-CD79 CAR may comprise an antigen-binding domain which comprises a) a heavy chain variable region (VH) having complementarity determining regions (CDRs) with the following sequences:

```
CDR1-
                                  (SEQ ID NO: 14)
SYWIE;

CDR2-
                                  (SEQ ID NO: 15)
EILPGGGDTNYNEIFKG

CDR3-
                                  (SEQ ID NO: 16)
RVPVYFDY;
``` and
b) a light chain variable region (VL) having CDRs with the following sequences:

```
CDR1-
                                  (SEQ ID NO: 17)
KASQSVDYDGDSFLN;

CDR2-
                                  (SEQ ID NO: 18)
AASNLES

CDR3-
                                  (SEQ ID NO: 19)
QQSNEDPLT.
```

The anti-CD79 CAR may comprise the following VH sequence:

```
VH sequence from monoclonal antibody
                                  SEQ ID NO: 20
EVQLVESGGGLVQPGGSLRLSCAASGYTFSSYWIEWVR

QAPGKGLEWIGEILPGGGDTNYNEIFKGRATFSADTSK

NTAYLQMNSLRAEDTAVYYCTRRVPVYFDYWGQGTLVT

VSS
```

The anti-CD79 CAR may comprise the following VL sequence:

```
VL sequence from monoclonal antibody
                                  SEQ ID No 21
DIQLTQSPSSLSASVGDRVTITCKASQSVDYDGDS

FLNWYQQKPGKAPKLLIYAASNLESGVPSRFSGSG

SGTDFTLTISSLQPEDFATYYCQQSNEDPLTFGQG

TKVEIKR
```

The anti-CD79 CAR may comprise the following scFv sequence:

```
(anti-CD79b-v17 scFv)
                                  SEQ ID NO: 22
METDTLLLWVLLLWVPGSTGDIQLTQSPSSLSASV

GDRVTITCKASQSVDYDGDSFLNWYQQKPGKAPKL

LIYAASNLESGVPSRFSGSGSGTDFTLTISSLQPE

DFATYYCQQSNEDPLTFGQGTKVEIKRSGGGGSGG

GGSGGGGSGGGGSEVQLVESGGGLVQPGGSLRLSC

AASGYTFSSYWIEWVRQAPGKGLEWIGEILPGGGD

TNYNEIFKGRATFSADTSKNTAYLQMNSLRAEDTA

VYYCTRRVPVYFDYWGQGTLVTVSS
```

Alternatively, the anti-CD79 CAR may comprise an antigen-binding domain which comprises a) a heavy chain variable region (VH) having complementarity determining regions (CDRs) with the following sequences:

```
CDR1-
                                  (SEQ ID NO: 14)
SYWIE;

CDR2-
                                  (SEQ ID NO: 15)
EILPGGGDTNYNEIFKG

CDR3-
                                  (SEQ ID NO: 23)
RVPIRLDY;
``` and
b) a light chain variable region (VL) having CDRs with the following sequences:

```
CDR1-
                                  (SEQ ID NO: 17)
KASQSVDYDGDSFLN;

CDR2-
                                  (SEQ ID NO: 18)
AASNLES

CDR3-
                                  (SEQ ID NO: 19)
QQSNEDPLT.
```

The anti-CD79 CAR may comprise the following VH sequence:

```
VH sequence from monoclonal antibody
                                 SEQ ID NO: 24
EVQLVESGGGLVQPGGSLRLSCAASGYTFSSYWIE

WVRQAPGKGLEWIGEILPGGGDTNYNEIFKGRATF

SADTSKNTAYLQMNSLRAEDTAVYYCTRRVPIRLD

YWGQGTLVTVSS
```

The anti-CD79 CAR may comprise the following VL sequence:

```
VL sequence from monoclonal antibody
                                 SEQ ID NO: 21
DIQLTQSPSSLSASVGDRVTITCKASQSVDYDGDS

FLNWYQQKPGKAPKLLIYAASNLESGVPSRFSGSG

SGTDFTLTISSLQPEDFATYYCQQSNEDPLTFGQG

TKVEIKR
```

The anti-CD79 CAR may comprise the following scFv sequence:

```
(anti-CD79b v18 scFv)
                                 SEQ ID NO: 25
DIQLTQSPSSLSASVGDRVTITCKASQSVDYDGDS

FLNWYQQKPGKAPKLLIYAASNLESGVPSRFSGSG

SGTDFTLTISSLQPEDFATYYCQQSNEDPLTFGQG

TKVEIKRSGGGGSGGGGSGGGGSGGGGSEVQLVES

GGGLVQPGGSLRLSCAASGYTFSSYWIEWVRQAPG

KGLEWIGEILPGGGDTNYNEIFKGRATFSADTSKN

TAYLQMNSLRAEDTAVYYCTRRVPIRLDYWGQGTL

VTVSS
```

Alternatively, the anti-CD79 CAR may comprise an antigen-binding domain which comprises a) a heavy chain variable region (VH) having complementarity determining regions (CDRs) with the following sequences:

```
CDR1-
                                 (SEQ ID NO: 14)
SYWIE;

CDR2-
                                 (SEQ ID NO: 15)
EILPGGGDTNYNEIFKG

CDR3-
                                 (SEQ ID NO: 23)
RVPIRLDY;
``` and
b) a light chain variable region (VL) having CDRs with the following sequences:

```
CDR1-
                                 (SEQ ID NO: 26)
KASQSVDYEGDSFLN;

CDR2-
                                 (SEQ ID NO: 18)
AASNLES

CDR3-
                                 (SEQ ID NO: 19)
QQSNEDPLT.
```

The anti-CD79 CAR may comprise the following VH sequence:

```
VH sequence from monoclonal antibody
                                 SEQ ID NO: 24
EVQLVESGGGLVQPGGSLRLSCAASGYTFSSYWIE

WVRQAPGKGLEWIGEILPGGGDTNYNEIFKGRATF

SADTSKNTAYLQMNSLRAEDTAVYYCTRRVPIRLD

YWGQGTLVTVSS
```

The anti-CD79 CAR may comprise the following VL sequence:

```
VL sequence from monoclonal antibody
                                 SEQ ID NO: 27
DIQLTQSPSSLSASVGDRVTITCKASQSVDYEGDS

FLNWYQQKPGKAPKLLIYAASNLESGVPSRFSGSG

SGTDFTLTISSLQPEDFATYYCQQSNEDPLTFGQG

TKVEIKR
```

The anti-CD79 CAR may comprise the following scFv sequence:

```
(anti-CD79b v28 scFv)
                                 SEQ ID NO: 28
METDTLLLWVLLLWVPGSTGDIQLTQSPSSLSASV

GDRVTITCKASQSVDYEGDSFLNWYQQKPGKAPKL

LIYAASNLESGVPSRFSGSGSGTDFTLTISSLQPE

DFATYYCQQSNEDPLTFGQGTKVEIKRSGGGGSGG

GGSGGGGSGGGGSEVQLVESGGGLVQPGGSLRLSC

AASGYTFSSYWIEWVRQAPGKGLEWIGEILPGGGD

TNYNEIFKGRATFSADTSKNTAYLQMNSLRAEDTA

VYYCTRRVPIRLDYWGQGTLVTVSS
```

Alternatively, the anti-CD79 CAR may comprise an antigen-binding domain which comprises a) a heavy chain variable region (VH) having complementarity determining regions (CDRs) with the following sequences:

```
CDR1-
                                    (SEQ ID NO: 14)
SYWIE;

CDR2-
                                    (SEQ ID NO: 15)
EILPGGGDTNYNEIFKG

CDR3-
                                    (SEQ ID NO: 23)
RVPIRLDY;
``` and
b) a light chain variable region (VL) having CDRs with the following sequences:

```
CDR1-
                                    (SEQ ID NO: 29)
KASQSVDYSGDSFLN;

CDR2-
                                    (SEQ ID NO: 18)
AASNLES

CDR-
                                    (SEQ ID NO: 19)
QQSNEDPLT
```

The anti-CD79 CAR may comprise the following VH sequence:

```
VH sequence from monoclonal antibody
                                    SEQ ID NO: 24
EVQLVESGGGLVQPGGSLRLSCAASGYTFSSYWIE

WVRQAPGKGLEWIGEILPGGGDTNYNEIFKGRATF

SADTSKNTAYLQMNSLRAEDTAVYYCTRRVPIRLD

YWGQGTLVTVSS
```

The anti-CD79 CAR may comprise the following VL sequence:

```
VL sequence from monoclonal antibody
                                    SEQ ID NO: 30
DIQLTQSPSSLSASVGDRVTITCKASQSVDYSGDS

FLNWYQQKPGKAPKLFIYAASNLESGVPSRFSGSG

SGTDFTLTISSLQPEDFATYYCQQSNEDPLTFGQG

TKVEIKR
```

The anti-CD79 CAR may comprise the following scFv sequence:

```
(anti-CD79b v32 scFv)
                                    SEQ ID NO: 31
METDTLLLWVLLLWVPGSTGDIQLTQSPSSLSASV

GDRVTITCKASQSVDYSGDSFLNWYQQKPGKAPKL

FIYAASNLESGVPSRFSGSGSGTDFTLTISSLQPE

DFATYYCQQSNEDPLTFGQGTKVEIKRSGGGSGG
```

```
-continued
GGSGGGGSGGGGSEVQLVESGGGLVQPGGSLRLSC

AASGYTFSSYWIEWVRQAPGKGLEWIGEILPGGGD

TNYNEIFKGRATFSADTSKNTAYLQMNSLRAEDTA

VYYCTRRVPIRLDYWGQGTLVTVSS
```

Alternatively, the anti-CD79 CAR may comprise an antigen-binding domain which comprises a) a heavy chain variable region (VH) having complementarity determining regions (CDRs) with the following sequences:

```
CDR1-
                                    (SEQ ID NO: 14)
SYWIE;

CDR2-
                                    (SEQ ID NO: 15)
EILPGGGDTNYNEIFKG

CDR3-
                                    (SEQ ID NO: 16)
RVPVYFDY;
``` and
b) a light chain variable region (VL) having CDRs with the following sequences:

```
CDR1-
                                    (SEQ ID NO: 17)
KASQSVDYDGDSFLN;

CDR2-
                                    (SEQ ID NO: 18)
AASNLES

CDR3-
                                    (SEQ ID NO: 19)
QQSNEDPLT.
```

The anti-CD79 CAR may comprise the following VH sequence:

```
VH sequence from monoclonal antibody
                                    SEQ ID NO: 32
EVQLQQSGAELMKPGASVKISCKATGYTFSSYWIE

WVKQRPGHGLEWIGEILPGGGDTNYNEIFKGKATF

TADTSSNTAYMQLSSLTSEDSAVYYCTRRVPVYFD

YWGQGTSVTVSS
```

The anti-CD79 CAR may comprise the following VL sequence:

```
VL sequence from monoclonal antibody
                                    SEQ ID NO: 33
DIVLTQSPASLAVSLGQRATISCKASQSVDYDGDS

FLNWYQQKPGQPPKLFIYAASNLESGIPARFSGSG

SGTDFTLNIHPVEEEDAATYYCQQSNEDPLTFGAG

TELELKR
```

The anti-CD79 CAR may comprise the following scFv sequence:

```
(anti-CD79b SN8 scFv)
                                        SEQ ID NO: 34
METDTLLLWVLLLWVPGSTGDIVLTQSPASLAVSL

GQRATISCKASQSVDYDGDSFLNWYQQKPGQPPKL

FIYAASNLESGIPARFSGSGSGTDFTLNIHPVEEE

DAATYYCQQSNEDPLTFGAGTELELKRSGGGGSGG

GGSGGGGSGGGGSEVQLQQSGAELMKPGASVKISC

KATGYTFSSYWIEWVKQRPGHGLEWIGEILPGGGD

TNYNEIFKGKATFTADTSSNTAYMQLSSLTSEDSA

VYYCTRRVPVYFDYWGQGTSVTVSS
```

Alternatively, the anti-CD79 CAR may comprise an antigen-binding domain which comprises a) a heavy chain variable region (VH) having complementarity determining regions (CDRs) with the following sequences:

```
CDR1-
                                        (SEQ ID NO: 14)
SYWIE;

CDR2-
                                        (SEQ ID NO: 15)
EILPGGGDTNYNEIFKG

CDR3-
                                        (SEQ ID NO: 23)
RVPIRLDY;
``` and
b) a light chain variable region (VL) having CDRs with the following sequences:

```
CDR1-
                                        (SEQ ID NO: 26)
KASQSVDYEGDSFLN;

CDR2-
                                        (SEQ ID NO: 18)
AASNLES

CDR3-
                                        (SEQ ID NO: 19)
QQSNEDPLT.
```

The anti-CD79 CAR may comprise the following VH sequence:

```
VH sequence from monoclonal antibody
                                        SEQ ID NO: 24
EVQLVESGGGLVQPGGSLRLSCAASGYTFSSYWIE

WVRQAPGKGLEWIGEILPGGGDTNYNEIFKGRATF

SADTSKNTAYLQMNSLRAEDTAVYYCTRRVPIRLD

YWGQGTLVTVSS
```

The anti-CD79 CAR may comprise the following VL sequence:

```
VL sequence from monoclonal antibody
                                        SEQ ID NO: 27
DIQLTQSPSSLSASVGDRVTITCKASQSVDYEGDS

FLNWYQQKPGKAPKLLIYAASNLESGVPSRFSGSG

SGTDFTLTISSLQPEDFATYYCQQSNEDPLTFGQG

TKVEIKR
```

The anti-CD79 CAR may comprise the following scFv sequence:

```
(humanised anti-CD79b 2F2 scFv;
polatuzumab)
                                        SEQ ID NO: 28
METDTLLLWVLLLWVPGSTGDIQLTQSPSSLSASV

GDRVTITCKASQSVDYEGDSFLNWYQQKPGKAPKL

LIYAASNLESGVPSRFSGSGSGTDFTLTISSLQPE

DFATYYCQQSNEDPLTFGQGTKVEIKRSGGGGSGG

GGSGGGGSGGGGSEVQLVESGGGLVQPGGSLRLSC

AASGYTFSSYWIEWVRQAPGKGLEWIGEILPGGGD

TNYNEIFKGRATFSADTSKNTAYLQMNSLRAEDTA

VYYCTRRVPIRLDYWGQGTLVTVSS
```

Alternatively, the anti-CD79 CAR may comprise an antigen-binding domain which comprises a) a heavy chain variable region (VH) having complementarity determining regions (CDRs) with the following sequences:

```
CDR1-
                                        (SEQ ID NO: 107)
NYGMN;

CDR2-
                                        (SEQ ID NO: 108)
RIYPGSGSTNYQKFKG

CDR3-
                                        (SEQ ID NO: 35)
YAMDY;
``` and
b) a light chain variable region (VL) having CDRs with the following sequences:

```
CDR1
                                        (SEQ ID NO: 109)
RSSQSIVHSNGNTYLE;

CDR2
                                        (SEQ ID NO: 110)
KVSNRPS

CDR3
                                        (SEQ ID NO: 111)
FQGSHVPWT.
```

The anti-CD79 CAR may comprise the following VH sequence:

```
VH sequence from murine monoclonal
antibody
                                    SEQ ID NO: 36
QVQLQQSGPELVKPGASVKISCKASGYTFTNYGMN

WVKQRPGQGLQWIGRIYPGSGSTNYQKFKGKATLT

VDKSSSTAYMELRSLTSENSAVYYCARYAMDYTGQ

GTSVTVSS
```

The anti-CD79 CAR may comprise the following VL sequence:

```
SEQ ID NO: 37 - VL sequence from murine monoclonal
antibody
DVLMTQTPLSLPVSLGDQASISCRSSQSIVHSNGNTYLEWYLQKPGQSPK

LLIYKVSNRPSGVPNRFSGSGSGTDFTLKISRVQAQNLGVYYCFQGSHVP

WTFGGGTKLEIKR
```

The anti-CD79 CAR may comprise the following scFv sequence:

```
(murine anti-CD79a scFv)
                                    SEQ ID NO: 38
METDTLLLWVLLLWVPGSTGDVLMTQTPLSLPVSLGDQASISCRSSQSIV

HSNGNTYLEWYLQKPGQSPKLLIYKVSNRPSGVPNRFSGSGSGTDFTLKI

SRVQAQNLGVYYCFQGSHVPWTFGGGTKLEIKRSGGGGSGGGGSGGGGSG

GGGSQVQLQQSGPELVKPGASVKISCKASGYTFTNYGMNWVKQRPGQGLQ

WIGRIYPGSGSTNYQKFKGKATLTVDKSSSTAYMELRSLTSENSAVYYCA

RYAMDYTGQGTSVTVSS
```

Alternatively, the anti-CD79 CAR may comprise an antigen-binding domain which comprises a) a heavy chain variable region (VH) having complementarity determining regions (CDRs) with the following sequences:

```
                                    (SEQ ID NO: 113)
        CDR1 - GFTFSNAA;

(SEQ ID NO: 114)
        CDR2 - IRTKPNNYAT (SEQ ID NO: 115)
        CDR3 - TYYDGSSYAMDA;
``` and
b) a light chain variable region (VL) having CDRs with the following sequences:

```
                                    (SEQ ID NO: 116)
        CDR1 - QSLEYSDGYTY;

SEQ ID NO:
        CDR2 - EVS (SEQ ID NO: 117)
        CDR3 - FQATHDPYT.
```

The anti-CD79 CAR may comprise the following VH sequence:

```
SEQ ID NO: - VH sequence from 2E8 antibody
AVQLVESGGGLVQPKESLKISCAASGFTFSNAAMYWVRQAPGKGLEWVAR

IRTKPNNYATNYADSVKGRFTISRDDSKSMVYLQMDNLKTEDTAMYYCTY

YDGSSYAMDAWGQGTSVTVSS
```

The anti-CD79 CAR may comprise the following VL sequence:

```
SEQ ID NO: 119 - VL sequence from 2E8 antibody
DVVLTQTPVSLSVTLGDQASISCRSSQSLEYSDGYTYLDWYLQKPGQSPQ

LLIYEVSNRFSGVPDRFIGSGSGTDFTLKISRVEPEDLGVYYCFQATHDP

YTFGAGTKLEIK
```

The anti-CD79 CAR may comprise the following scFv sequence:

```
(2E8 scFv)
                                    SEQ ID NO: 120
DVVLTQTPVSLSVTLGDQASISCRSSQSLEYSDGYTYLDWYLQKPGQSPQ

LLIYEVSNRFSGVPDRFIGSGSGTDFTLKISRVEPEDLGVYYCFQATHDP

YTFGAGTKLEIKRSGGGGSGGGGSGGGGSAVQLVESGGGLVQPKESLKIS

CAASGFTFSNAAMYWVRQAPGKGLEWVARIRTKPNNYATNYADSVKGRFT

ISRDDSKSMVYLQMDNLKTEDTAMYYCTYYDGSSYAMDAWGQGTSVTVSS
```

Alternatively, the anti-CD79 CAR may comprise an antigen-binding domain which comprises a) a heavy chain variable region (VH) having complementarity determining regions (CDRs) with the following sequences:

```
                                    (SEQ ID NO: 121)
        CDR1 - GFTFSHTA;

(SEQ ID NO: 122)
        CDR2 - IRIQPKNYAT (SEQ ID NO: 123)
        CDR3 - TAAGFGFDY;
``` and
b) a light chain variable region (VL) having CDRs with the following sequences:

```
                                    (SEQ ID NO: 124)
        CDR1 - QSLEYSDGNTY;

SEQ ID NO:
        CDR2 - EVS (SEQ ID NO: 125)
        CDR3 - LQATHDPFT.
```

The anti-CD79 CAR may comprise the following VH sequence:

```
SEQ ID NO: 126 - VH sequence from 3H2 antibody
AVQLVESGGGLVQPKESLKLSCAASGFTFSHTAMYWVRQAPGKGLECVAR

IRIQPKNYATYYADSVKGRFTISRDDSKSMVYLQMDNLKTEDTAMYYCTA

AGFGFDYWGQGVMVTVSS
```

The anti-CD79 CAR may comprise the following VL sequence:

SEQ ID NO: 127 - VL sequence from 3H2 antibody
DVVLTQTPVSLSVTLGDQASISCRSSQSLEYSDGNTYLEWYLQKPGQSPQ
LLIYEVSKRFSGVPDRFIGSGSGTDFTLKISRVEPEDLGIYYCLQATHDP
FTFGSGTKLEIK The anti-CD79 CAR may comprise the following scFv sequence:

(3H2 scFv)
SEQ ID NO: 128
DVVLTQTPVSLSVTLGDQASISCRSSQSLEYSDGNTYLEWYLQKPGQSPQ
LLIYEVSKRFSGVPDRFIGSGSGTDFTLKISRVEPEDLGIYYCLQATHDP
FTFGSGTKLEIKRSGGGGSGGGGSGGGGSAVQLVESGGGLVQPKESLKLS
CAASGFTFSHTAMYWVRQAPGKGLECVARIRIQPKNYATYYADSVKGRFT
ISRDDSKSMVYLQMDNLKTEDTAMYYCTAAGFGFDYWGOGVMVTVSS

Alternatively, the anti-CD79 CAR may comprise an antigen-binding domain which comprises a) a heavy chain variable region (VH) having complementarity determining regions (CDRs) with the following sequences:

(SEQ ID NO: 113)
CDR1 - GFTFSNAA;

(SEQ ID NO: 114)
CDR2 - IRTKPNNYAT (SEQ ID NO: 129)
CDR3 - TADGGYGFDY;

and
b) a light chain variable region (VL) having CDRs with the following sequences:

(SEQ ID NO: 116)
CDR1 - QSLEYSDGYTY;

SEQ ID NO:
CDR2 - EVS (SEQ ID NO: 130)
CDR3 - FQGTHDPYT.

The anti-CD79 CAR may comprise the following VH sequence:

SEQ ID NO: 131 - VH sequence from 4G11 antibody
AVQLVESGGGLVQPEESLKISCAASGFTFSNAAMFWVRQAPGKGLEWIAR
IRTKPNNYATYYVDSVKGRFTISRDDSKSMVYLQMDNLKTEDTAMYYCTA
DGGYGFDYWGQGVMVTVSS The anti-CD79 CAR may comprise the following VL sequence:

SEQ ID NO: 132 - VL sequence from 4G11 antibody
DVVLTQTPVSLSVTLGDQASISCRSSQSLEYSDGYTYLEWYLQKPGQSPQ
LLIYEVSNRFSGVPDRFIGSGSGTDFTLKISRVEPEDLGLYYCFQGTHDP
YTFGAGTKLEIK The anti-CD79 CAR may comprise the following scFv sequence:

(4G11 scFv)
SEQ ID NO: 133
DVVLTQTPVSLSVTLGDQASISCRSSQSLEYSDGYTYLEWYLQKPGQSPQ
LLIYEVSNRFSGVPDRFIGSGSGTDFTLKISRVEPEDLGLYYCFQGTHDP
YTFGAGTKLEIKRSGGGGSGGGGSGGGGSAVQLVESGGGLVQPEESLKIS
CAASGFTFSNAAMFWVRQAPGKGLEWIARIRTKPNNYATYYVDSVKGRFT
ISRDDSKSMVYLQMDNLKTEDTAMYYCTADGGYGFDYWGQGVMVTVSS

Alternatively, the anti-CD79 CAR may comprise an antigen-binding domain which comprises a) a heavy chain variable region (VH) having complementarity determining regions (CDRs) with the following sequences:

(SEQ ID NO: 113)
CDR1 - GFTFSNAA;

(SEQ ID NO: 114)
CDR2 - IRTKPNNYAT (SEQ ID NO: 115)
CDR3 - TYYDGSSYAMDA;

and
b) a light chain variable region (VL) having CDRs with the following sequences:

(SEQ ID NO: 116)
CDR1 - QSLEYSDGYTY;

SEQ ID NO:
CDR2 - EIS (SEQ ID NO: 117)
CDR3 - FQATHDPYT.

The anti-CD79 CAR may comprise the following VH sequence:

SEQ ID NO: 118 - VH sequence from 7G4 antibody
AVQLVESGGGLVQPKESLKISCAASGFTFSNAAMYWVRQAPGKGLEWVAR
IRTKPNNYATNYADSVKGRFTISRDDSKSMVYLQMDNLKTEDTAMYYCTY
YDGSSYAMDAWGQGTSVTVSS The anti-CD79 CAR may comprise the following VL sequence:

SEQ ID NO: 134 - VL sequence from 7G4 antibody
DVVLTQTPVSLSVTLGDQASISCRSSQSLEYSDGYTYLDWYLQKPGQSPQ
LLIYEISNRFSGVPDRFIGSGSGTDFTLKISRVEPEDLGVYYCFQATHDP
YTFGAGTKLEIK The anti-CD79 CAR may comprise the following scFv sequence:

(7G4 scFv)
SEQ ID NO: 135
DVVLTQTPVSLSVTLGDQASISCRSSQSLEYSDGYTYLDWYLQKPGQSPQ
LLIYEISNRFSGVPDRFIGSGSGTDFTLKISRVEPEDLGVYYCFQATHDP

-continued
YTFGAGTKLEIKRSGGGGSGGGGSGGGGSAVQLVESGGGLVQPKESLKIS

CAASGFTFSNAAMYWVRQAPGKGLEWVARIRTKPNNYATNYADSVKGRFT

ISRDDSKSMVYLQMDNLKTEDTAMYYCTYYDGSSYAMDAWGQGTSVTVSS

Alternatively, the anti-CD79 CAR may comprise an antigen-binding domain which comprises a) a heavy chain variable region (VH) having complementarity determining regions (CDRs) with the following sequences:

```
                              (SEQ ID NO: 136)
          CDR1 - GFTFSNTA;

(SEQ ID NO: 122)
          CDR2 - IRIQPKNYAT (SEQ ID NO: 123)
          CDR3 - TAAGFGFDY;
``` and
b) a light chain variable region (VL) having CDRs with the following sequences:

```
                              (SEQ ID NO: 137)
          CDR1 - QRLEYSDGNTY;

SEQ ID NO:
          CDR2 - EVS (SEQ ID NO: 125)
          CDR3 - LQATHDPFT.
```

The anti-CD79 CAR may comprise the following VH sequence:

SEQ ID NO: 138 - VH sequence from 9F1 antibody
AVQLVESGGGLVRPKESLKISCAASGFTFSNTAMYWVRQAPGKGLECVAR

IRIQPKNYATFYADSVKGRFTISRDDSKSMVYLRMDNLKTEDTAMYYCTA

AGFGFDYWGQGVMVTVSS

The anti-CD79 CAR may comprise the following VL sequence:

SEQ ID NO: 139 - VL sequence from 9F1 antibody
DVVLTQTPVSLSVTLGDQASISCRSSQRLEYSDGNTYLEWYLQKPGQSPQ

LLIYEVSERFSGVPDRFIGSGSGTDFTLKISRVEPEDLGVYYCLQATHDP

FTFGSGTKLEIK

The anti-CD79 CAR may comprise the following scFv sequence:

(9F1 scFv)
                                       SEQ ID NO: 140
DVVLTQTPVSLSVTLGDQASISCRSSQRLEYSDGNTYLEWYLQKPGQSPQ

LLIYEVSERFSGVPDRFIGSGSGTDFTLKISRVEPEDLGVYYCLQATHDP

FTFGSGTKLEIKRSGGGGSGGGGSGGGGSAVQLVESGGGLVRPKESLKIS

CAASGFTFSNTAMYWVRQAPGKGLECVARIRIQPKNYATFYADSVKGRFT

ISRDDSKSMVYLRMDNLKTEDTAMYYCTAAGFGFDYWGQGVMVTVSS

Alternatively, the anti-CD79 CAR may comprise an antigen-binding domain which comprises a) a heavy chain variable region (VH) having complementarity determining regions (CDRs) with the following sequences:

```
                              (SEQ ID NO: 141)
          CDR1 - GFTFSSAA;

(SEQ ID NO: 114)
          CDR2 - IRTKPNNYAT (SEQ ID NO: 115)
          CDR3 - TYYDGSSYAMDA;
``` and
b) a light chain variable region (VL) having CDRs with the following sequences:

```
                              (SEQ ID NO: 116)
          CDR1 - QSLEYSDGYTY;

SEQ ID NO:
          CDR2 - EVS (SEQ ID NO: 117)
          CDR3 - FQATHDPYT.
```

The anti-CD79 CAR may comprise the following VH sequence:

SEQ ID NO: 142 - VH sequence from 10C11 antibody
AVQFVESGGGLVQPKESLKISCAASGFTFSSAAMYWVRQAPGKGLEWLAR

IRTKPNNYATNYADSVKGRFTISRDDSKSMVYLQMDNLKTEDSAMYYCTY

YDGSSYAMDAWGQGTSVTVSS

The anti-CD79 CAR may comprise the following VL sequence:

SEQ ID NO: 143
VL sequence from 10C11 antibody
DVVLTQTPVSLSVTLGDQASISCRSSQSLEYSDGYTYLDWYLQKPGQSPQ

LLISEVSNRFSGVPDRFIGSGSGTDFTLKISRVEPEDLGVYYCFQATHDP

YTFGAGTKLEIK

The anti-CD79 CAR may comprise the following scFv sequence:

SEQ ID NO: 144
(10C11 scFv)
DVVLTQTPVSLSVTLGDQASISCRSSQSLEYSDGYTYLDWYLQKPGQSPQ

LLISEVSNRFSGVPDRFIGSGSGTDFTLKISRVEPEDLGVYYCFQATHDP

YTFGAGTKLEIKRSGGGGSGGGGSGGGGSAVQFVESGGGLVQPKESLKIS

CAASGFTFSSAAMYWVRQAPGKGLEWLARIRTKPNNYATNYADSVKGRFT

ISRDDSKSMVYLQMDNLKTEDSAMYYCTYYDGSSYAMDAWGQGTSVTVSS

It may be possible to introduce one or more mutations (substitutions, additions or deletions) into the or each CDR without negatively affecting CD79-binding activity. Each CDR may, for example, have one, two or three amino acid mutations.

The CDRs may be grafted on to the framework of a human antibody or scFv.

The CAR of the present invention may comprise a dAb which specifically binds CD79.

The terms "dAb", "VHH", "domain antibody" and "nanobody" are used indistinctively in the context of the present invention.

The CAR of the present invention may comprise a Fab which specifically binds CD79. The Fab fragment is derived from, for example, a monoclonal antibody (see FIG. 2a). The resulting FabCAR comprises two chains: one having an antibody-like light chain variable region (VL) and constant region (CL); and one having a heavy chain variable region (VH) and constant region (CH). One chain also comprises a transmembrane domain and an intracellular signalling domain. Association between the CL and CH causes assembly of the receptor.

The two chains of a Fab CAR may have the general structure:

VH-CH-spacer-transmembrane domain-intracellular signalling domain; and VL-CL or

VL-CL-spacer-transmembrane domain-intracellular signalling domain; and VH-CH

For the Fab-type chimeric receptors described herein, the antigen binding domain is made up of a VH from one polypeptide chain and a VL from another polypeptide chain.

The polypeptide chains may comprise a linker between the VH/VL domain and the CH/CL domains. The linker may be flexible and serve to spatially separate the VH/VL domain from the CH/CL domain.

Flexible linkers may be composed of small non-polar residues such as glycine, threonine and serine. The linker may comprise one or more repeats of a glycine-serine linker, such as a $(Gly_4Ser)_n$ linker (SEQ ID NO: 112), where n is the number of repeats. The or each linker may be less than 50, 40, 30, 20 or 10 amino acids in length.

There are two types of light chain in humans: kappa (κ) chain and lambda (λ) chain. The lambda class has 4 subtypes: $\lambda_1, \lambda_2, \lambda_3$ and $\lambda_4$ The light chain constant region of a Fab-type chimeric receptor may be derived from any of these light chain types.

The light chain constant domain of a chimeric receptor of the present invention may have the sequence shown as SEQ ID NO: 39 which is a kappa chain constant domain.

```
                                         SEQ ID NO: 39
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC
```

There are five types of mammalian immunoglobulin heavy chain: γ, δ, α, μ and ε which define the classes of immunoglobulin IgG, IgD, IgA, IgM and IgE respectively. Heavy chains γ, δ and α have a constant domain composed of three tandem Ig domain and have a hinge for added flexibility. Heavy chains μ and ε are composed of four domains.

The CH domain of a Fab-type chimeric receptor of the present invention may comprise the sequence shown as SEQ ID NO: 40 which is from a γ immunoglobulin heavy chain.

```
                                         SEQ ID NO: 40
STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKRV
```

The present invention also contemplates using variants of the sequences of the antigen binding domains identified in this description, which fall within the scope of the present invention. As it is used herein, the term "variant" or "functional variant" refers to a substantially similar sequence that substantially maintains its capacity to bind to its cognate antigen, i.e., its affinity and/or the specificity/selectivity. A variant of an antigen binding domain can be a polypeptide sequence derivative identified in this description comprising the addition, deletion or substitution of one or more amino acids. The sites of greatest interest for substitution mutagenesis of antibodies include the hypervariable regions, but framework alterations are also contemplated. According to the invention, variants of a an antigen binding domain comprising the amino acid sequence shown in one of SEQ ID NO: 5 to 38 and 113 to 144 include an antigen binding domain comprising amino acid sequences having at least approximately 80% sequence identity with the corresponding amino acid sequence shown in one of SEQ ID NO: 5 to 38 and 113 to 144, preferably at least 85%, 90%, 91%, 92%, 93%, 94%, 95%, 96%, 97%, 98% or 99% sequence identity with the corresponding amino acid sequences shown in one of SEQ ID NO: 5 to 38 and 113 to 144. It is also contemplated that variants comprise additions consisting of at least 1 amino acid, or at least 2 amino acids, or at least 3 amino acids, or at least 4 amino acids, or at least 5 amino acids, or more amino acids at the N-terminus, or the C-terminus, or both the N-and C-terminus of the an antigen binding domain. Likewise, it is also contemplated that variants comprise deletions consisting of at least 1 amino acid, or at least 2 amino acids, or at least 3 amino acids, or at least 4 amino acids, or at least 5 amino acids, or more amino acids at the N-terminus, or the C-terminus, or both the N-and C-terminus of the antigen binding domain. Functional variants of an antibody according to the invention will preferably have a capacity to bind to its cognate target of at least 50%, at least 60%, at least 70%, at least 80%, at least 90%, at least 91%, at least 92%, at least 93%, at least 94%, at least 95%, at least 96%, at least 97%, at least 98%, or at least 99% the capacity to bind to its cognate target of said antigen binding domain. The percentage identity between two polypeptide sequences may be readily determined by programs such as BLAST which is freely available at blast.ncbi.nlm-.nih.gov.

1.3. Spacer Domain

CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

In the CAR of the present invention, the spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs. The spacer may comprise a coiled-coil domain, for example as described in WO2016/151315.

The CAR of the present invention may comprise a sequence selected from the sequences shown as SEQ ID NOs: 41 to 45 or a variant thereof having at least 80% sequence identity.

SEQ ID NO: 41
(hinge-CH2CH3 of human IgG1)
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD

SEQ ID NO: 42
(human CD8 stalk):
TTTPAPRPPTPAPTIASQPLSLRPEACRPAAGGAVHTRGLDFACDI

SEQ ID NO: 43
(human IgG1 hinge):
AEPKSPDKTHTCPPCPKDPK

SEQ ID NO: 44
(CD2 ectodomain)
KEITNALETWGALGQDINLDIPSFQMSDDIDDIKWEKTSDKKKIAQFRKE

KETFKEKDTYKLFKNGTLKIKHLKTDDQDIYKVSIYDTKGKNVLEKIFDL

KIQERVSKPKISWTCINTTLTCEVMNGTDPELNLYQDGKHLKLSQRVITH

KWTTSLSAKFKCTAGNKVSKESSVEPVSCPEKGLD

SEQ ID NO: 45
(CD34 ectodomain)
SLDNNGTATPELPTQGTFSNVSTNVSYQETTTPSTLGSTSLHPVSQHGNE

ATTNITETTVKFTSTSVITSVYGNTNSSVQSQTSVISTVFTTPANVSTPE

TTLKPSLSPGNVSDLSTTSTSLATSPTKPYTSSSPILSDIKAEIKCSGIR

EVKLTQGICLEQNKTSSCAEFKKDRGEGLARVLCGEEQADADAGAQVCSL

LLAQSEVRPQCLLLVLANRTEISSKLQLMKKHQSDLKKLGILDFTEQDVA

SHQSYSQKT

1.4. Transmembrane Domain

The transmembrane domain is the sequence of the CAR that spans the membrane.

A transmembrane domain may be any protein structure which is thermodynamically stable in a membrane. This is typically an alpha helix comprising of several hydrophobic residues. The transmembrane domain of any transmembrane protein can be used to supply the transmembrane portion of the invention. The presence and span of a transmembrane domain of a protein can be determined by those skilled in the art using the TMHMM algorithm (www.cbs.dtu.dk/services/TMHMM-2.0/). Further, given that the transmembrane domain of a protein is a relatively simple structure, i.e. a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, CD8a or TYRP-1, which give good receptor stability.

In an embodiment, the transmembrane domain is derived from CD8a.

SEQ ID NO: 46: CD8a transmembrane domain
IYIWAPLAGTCGVLLLSLVIT

In another embodiment, the transmembrane domain is derived from TYRP-1.

SEQ ID NO: 47: TYRP-1 transmembrane domain
IIAIAVVGALLLVALIFGTASYLI

1.5. Endodomain

The endodomain is the signal-transmission portion of the CAR. After antigen recognition, receptors cluster, native CD45 and CD148 are excluded from the synapse and a signal is transmitted to the cell. The most commonly used endodomain component is that of CD3ζ which contains 3 ITAMs. This transmits an activation signal to the T cell after antigen is bound. CD3ζ may not provide a fully competent activation signal and additional co-stimulatory signalling may be needed. Examples of co-stimulatory domains include the endodomains from CD28, OX40, 4-1BB, CD27, and ICOS, which can be used with CD3ζ to transmit a proliferative/survival signal.

In an embodiment, at least one co-stimulatory endodomain is used with CD3ζ. In a particular embodiment, the co-stimulatory endodomain is selected from the group consisting of the endodomains from CD28, OX40, 4-1BB, CD27, and ICOS.

In another embodiment, at least two co-stimulatory endodomains are used with CD3ζ. In a particular embodiment, the two co-stimulatory endodomain are selected from the group consisting of the endodomains from CD28, OX40, 4-1BB, CD27, and ICOS, in any combination and order. Particularly suitable combinations include the endodomains from CD28 and CD3ζ, the endodomains of OX40 and CD3ζ, the endodomains of 4-1BB and CD3ζ, the endodomains from CD28, OX40 and CD3ζ, and the endodomains from CD28, 4-1BB and CD3ζ.

The transmembrane and intracellular T-cell signalling domain (endodomain) of a CAR with an activating endodomain may comprise the sequence shown as SEQ ID NO: 48 to 52 or a variant thereof having at least 80% sequence identity.

SEQ ID NO: 48
comprising CD28 transmembrane domain and CD3 endodomain
FWVLVVVGGVLACYSLLVTVAFIIFWVRRVKFSRSADAPAYQQGQNQLYN

ELNLGRREEYDVLDKRRGRDPEMGGKPRRKNPQEGLYNELQKDKMAEAYS

EIGMKGERRRGKGHDGLYQGLSTATKDTYDALHMQALPPR

SEQ ID NO: 49
comprising CD28 transmembrane domain and CD28 and CD3 endodomains
FWVLVVVGGVLACYSLLVTVAFIIFWVRSKRSRLLHSDYMNMTPRRPGPT

RKHYQPYAPPRDFAAYRSRVKFSRSADAPAYQQGQNQLYNELNLGRREEY

DVLDKRRGRDPEMGGKPRRKNPQEGLYNELQKDKMAEAYSEIGMKGERRR

GKGHDGLYQGLSTATKDTYDALHMQALPPR

SEQ ID NO: 50
comprising CD28 transmembrane domain and CD28, OX40 and CD3 endodomains
FWVLVVVGGVLACYSLLVTVAFIIFWVRSKRSRLLHSDYMNMTPRRPGPT

RKHYQPYAPPRDFAAYRSRDQRLPPDAHKPPGGGSFRTPIQEEQADAHST

LAKIRVKFSRSADAPAYQQGQNQLYNELNLGRREEYDVLDKRRGRDPEMG

-continued

GKPRRKNPQEGLYNELQKDKMAEAYSEIGMKGERRRGKGHDGLYQGLSTA

TKDTYDALHMQALPPR

SEQ ID NO: 51
comprising CD8a transmembrane domain and CDζ
endodomain
IYIWAPLAGTCGVLLLSLVITRVLYCKFSRSADAPAYQQGQNQLYNELNL

GRREEYDVLDKRRGRDPEMGGKPRRKNPQEGLYNELQKDKMAEAYSEIGM

KGERRRGKGHDGLYQGLSTATKDTYDALHMQALPPR

SEQ ID NO: 52
comprising CD8a transmembrane domain and 4-1BB and
CD3 endodomain
IYIWAPLAGTCGVLLLSLVITLYCKRGRKKLLYIFKQPFMRPVQTTQEED

GCSCRFPEEEEGGCELRVKFSRSADAPAYQQGQNQLYNELNLGRREEYDV

LDKRRGRDPEMGGKPRRKNPQEGLYNELQKDKMAEAYSEIGMKGERRRGK

GHDGLYQGLSTATKDTYDALHMQALPPR

A variant sequence may have at least 80%, 85%, 90%, 95%, 98% or 99% sequence identity to SEQ ID NO: 48 to 52, provided that the sequence provides an effective transmembrane domain and an effective intracellular T cell signalling domain.

3. Logic Gates

The CAR of the present invention may be used in a combination with one or more other activatory or inhibitory chimeric antigen receptors. For example, they may be used in combination with one or more other CARs in a "logic-gate", a CAR combination which, when expressed by a cell, such as a T cell, are capable of detecting a particular pattern of expression of at least two target antigens. If the at least two target antigens are arbitrarily denoted as antigen A and antigen B, the three possible options are as follows:

"OR GATE"—T cell triggers when either antigen A or antigen B is present on the target cell "AND GATE"—T cell triggers only when both antigens A and B are present on the target cell "AND NOT GATE"—T cell triggers if antigen A is present alone on the target cell, but not if both antigens A and B are present on the target cell Engineered T cells expressing these CAR combinations can be tailored to be exquisitely specific for cancer cells, based on their particular expression (or lack of expression) of two or more markers.

Such "Logic Gates" are described, for example, in WO2015/075469, WO2015/075470 and WO2015/075470.

An "OR Gate" comprises two or more activatory CARs each directed to a distinct target antigen expressed by a target cell. The advantage of an OR gate is that the effective targetable antigen is increased on the target cell, as it is effectively antigen A +antigen B and, optionally, +antigen C and so on. This is especially important for antigens expressed at variable or low density on the target cell, as the level of a single antigen may be below the threshold needed for effective targeting by a CAR-T cell. Also, it prevents the phenomenon of antigen escape. For example, some lymphomas and leukemias become CD19 negative after CD19 targeting: using an OR gate which targets CD19 in combination with another antigen provides a "back-up" antigen, should this occur.

Each of the CARs in the OR gate is independently capable of activating the T cell. The T cell is thus activated by the presence of either antigen alone. The two or more CARs are not "complementary" in the sense that activation of both CARs is necessary to provide activation and co-stimulatory signals.

The CAR which specifically binds CD79 of the present invention may be used in an OR gate in combination with a second CAR against a second target antigen expressed by the target cell.

For an anti-CD79 CAR, the OR gate may comprise a CAR against a second antigen expressed in B cells, such as CD19, CD20 or CD22, preferably CD19 and CD22.

The second CAR may have any suitable antigen binding domain, for example a binding domain based on an scFv, dAb or a Fab.

The second CAR may comprise a spacer to spatially separate the antigen binding domain from the transmembrane domain and provide a degree of flexibility. A variety of sequences are commonly used as spacers for CAR, for example, an IgG1 Fc region, an IgG1 hinge or a human CD8 stalk (as described above). The spacer may comprise a coiled-coil domain, for example as described in WO2016/151315.

The second CAR comprises an activating endodomain. It may, for example comprise the endodomain from CD3. It may comprise one or more co-stimulatory domains as described above. For example, it may comprise the endodomains from CD28, OX-40 or 4-1BB.

The CAR of the present invention may be used in a triple OR gate, which comprises a second CAR against a second antigen and a third CAR against a third antigen expressed by the target cell. The second CAR and third CAR may independently have any suitable antigen binding domain, for example a binding domain based on an scFv, dAb or a Fab.

For an anti-CD79 CAR, a triple OR gate may comprise CARs against second and third antigens expressed in B cells, such as CD19, CD20 or CD22, preferably CD19 and CD22.

Figure 3:
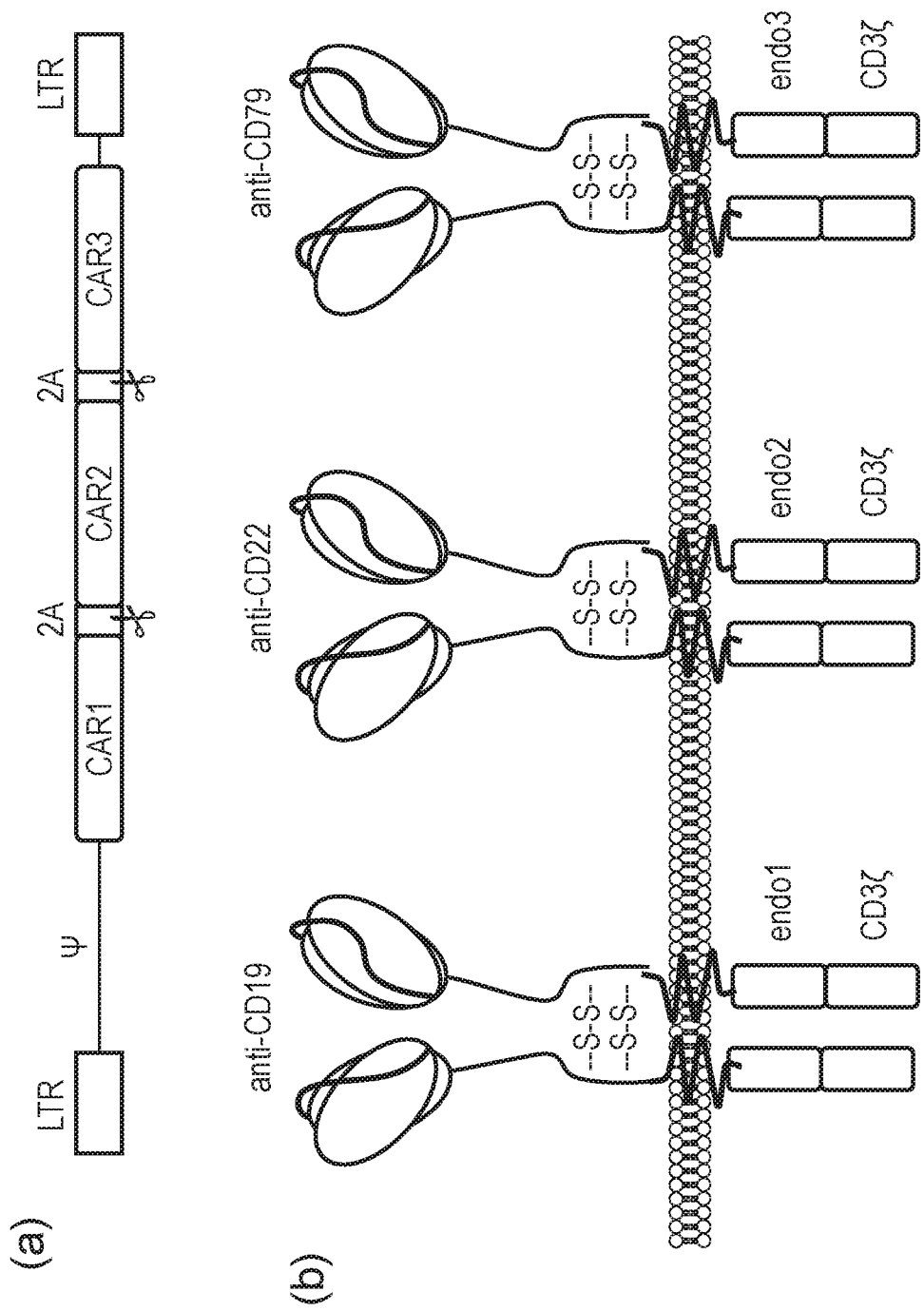
FIG. 3. CAR OR gate targeting CD19, CD22 and CD79
(a) A tricistronic cassette can be generated be separating the coding sequences for the two receptors using two FMD-2A sequences; (b) OR gate where all three receptors are scFv CARs. Each can have different endodomains.

In particular, the present invention provides a triple OR gate which comprises:

(i) an anti-CD79 scFv CAR;

(ii) an anti-CD19 scFv CAR; and (iii) an anti-CD22 scFv CAR (see FIG. 3b).

Figure 4:
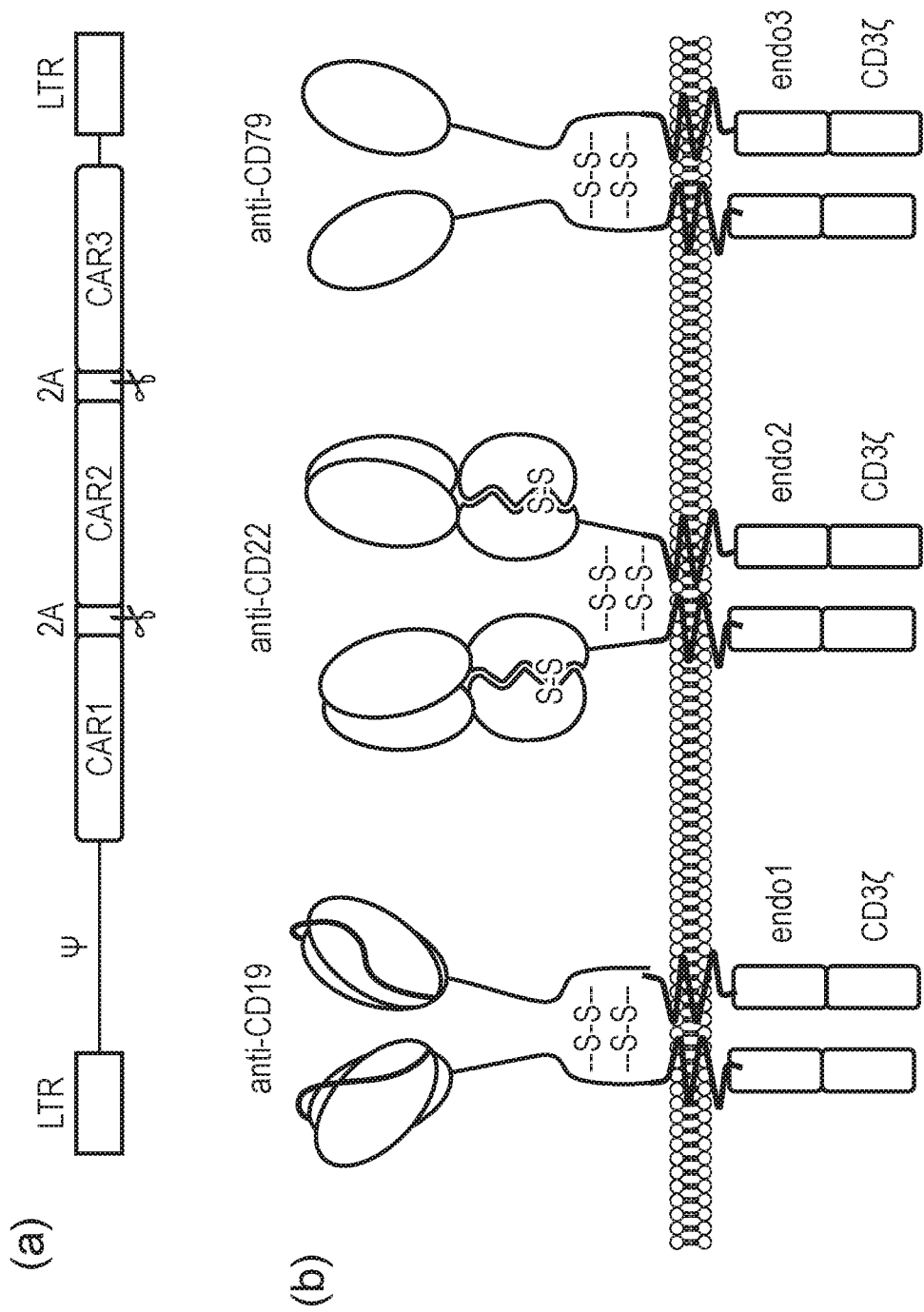
FIG. 4. CAR OR gate targeting CD19, CD22 and CD79 using different format CARs
(a) A tricistronic cassette can be generated be separating the coding sequences for the two receptors using two FMD-2A sequences; (b) OR gate combining three different formats: scFv-CAR for CD19, Fab CAR for CD22 and dAb CAR for CD79.

In particular, the present invention provides a triple OR gate which comprises:

(i) an anti-CD79 dAb CAR;

(ii) an anti-CD19 scFv CAR; and (iii) an anti-CD22 FabCAR (see FIG. 4b).

3.1. CD79 Binders

Binders specific for CD79 are described in the context of the CAR of the invention and their particular and preferred features apply equally in the context of logic gates.

3.2. CD19 Binders

Several anti-CD19 antibodies have been previously described in a CAR format, such as fmc63, 4G7, SJ25C1, CAT19 (as described in WO2016/139487) and CD19ALAb (as described in WO2016/102965)

An anti-CD19 CAR for use in a double or triple OR gate of the present invention may comprise an antigen-binding domain, such as an scFv-type antigen binding domain, derived from one of these anti-CD19 antibodies.

The CD19-binding domain may comprises a) a heavy chain variable region (VH) having complementarity determining regions (CDRs) with the following sequences:

```
                                    (SEQ ID NO: 53)
         CDR1 - GYAFSSS;

(SEQ ID NO: 54)
         CDR2 - YPGDED (SEQ ID NO: 55)
         CDR3 - SLLYGDYLDY;
``` and b) a light chain variable region (VL) having CDRs with the following sequences:

```
                                    (SEQ ID NO: 56)
         CDR1 - SASSSVSYMH;

(SEQ ID NO: 57)
         CDR2 - DTSKLAS (SEQ ID NO: 58)
         CDR3 - QQWNINPLT.
```

It may be possible to introduce one or more mutations (substitutions, additions or deletions) into each CDR without negatively affecting CD19-binding activity. Each CDR may, for example, have one, two or three amino acid mutations.

The CDRs may be in the format of a single-chain variable fragment (scFv), which is a fusion protein of the heavy variable region (VH) and light chain variable region (VL) of an antibody, connected with a short linker peptide of ten to about 25 amino acids. The scFv may be in the orientation VH-VL, i.e. the VH is at the amino-terminus of the CAR molecule and the VL domain is linked to the spacer and, in turn the transmembrane domain and endodomain.

The CDRs may be grafted on to the framework of a human antibody or scFv. For example, the CAR of the present invention may comprise a CD19-binding domain consisting or comprising one of the following sequences The anti-CD19 CAR may comprise the following VH sequence:

```
SEQ ID NO: 59
VH sequence from murine monoclonal antibody
QVQLQQSGPELVKPGASVKISCKASGYAFSSSWMNWVKQRPGKGLEWIGR

IYPGDEDTNYSGKFKDKATLTADKSSTTAYMQLSSLTSEDSAVYFCARSL

LYGDYLDYWGQGTTLTVSS
```

The anti-CD19 CAR may comprise the following VL sequence:

```
SEQ ID No 60
VL sequence from murine monoclonal antibody
QIVLTQSPAIMSASPGEKVTMTCSASSSVSYMHWYQQKSGTSPKRWIYDT

SKLASGVPDRFSGSGSGTSYFLTINNMEAEDAATYYCQQWNINPLTFGAG

TKLELKR
```

The anti-CD19 CAR may comprise the following scFv sequence:

```
                                    SEQ ID No 61
VH-VL scFv sequence from murine monoclonal
antibody
QVQLQQSGPELVKPGASVKISCKASGYAFSSSWMNWVKQRPGKGLEWIGR

IYPGDEDTNYSGKFKDKATLTADKSSTTAYMQLSSLTSEDSAVYFCARSL

LYGDYLDYWGQGTTLTVSSGGGGSGGGGSGGGGSQIVLTQSPAIMSASPG

EKVTMTCSASSSVSYMHWYQQKSGTSPKRWIYDTSKLASGVPDRFSGSGS

GTSYFLTINNMEAEDAATYYCQQWNINPLTFGAGTKLELKR
```

Alternatively, the anti-CD19 CAR may comprise an antigen-binding domain which comprises a) a heavy chain variable region (VH) having complementarity determining regions (CDRs) with the following sequences:

```
                                    (SEQ ID NO: 62)
         CDR1 - SYWMN;

(SEQ ID NO: 63)
         CDR2 - QIWPGDGDTNYNGKFK (SEQ ID NO: 64)
         CDR3 - RETTTVGRYYYAMDY;
``` and b) a light chain variable region (VL) having CDRs with the following sequences:

```
                                    (SEQ ID NO: 65)
         CDR1 - KASQSVDYDGDSYLN;

(SEQ ID NO: 66)
         CDR2 - DASNLVS (SEQ ID NO: 67)
         CDR3 - QQSTEDPWT.
```

It may be possible to introduce one or more mutations (substitutions, additions or deletions) into the or each CDR without negatively affecting CD19-binding activity. Each CDR may, for example, have one, two or three amino acid mutations.

The CAR of the present invention may comprise one of the following amino acid sequences:

```
(Murine CD19ALAb scFv sequence)
                                    SEQ ID NO: 68
QVQLQQSGAELVRPGSSVKISCKASGYAFSSYWMNWVKQRPGQGLEWIGQ

IWPGDGDTNYNGKFKGKATLTADESSSTAYMQLSSLASEDSAVYFCARRE

TTTVGRYYYAMDYWGQGTTVTVSSDIQLTQSPASLAVSLGQRATISCKAS

QSVDYDGDSYLNWYQQIPGQPPKWYDASNLVSGIPPRFSGSGSGTDFTLN

IHPVEKVDAATYHCQQSTEDPWTFGGGTKLEIK (Humanised CD19ALAb scFv sequence - Heavy 19,
Kappa 16)
                                    SEQ ID NO: 69
QVQLVQSGAEVKKPGASVKLSCKASGYAFSSYWMNWVRQAPGQSLEWIGQ

IWPGDGDTNYNGKFKGRATLTADESARTAYMELSSLRSGDTAVYFCARRE

TTTVGRYYYAMDYWGKGTLVTVSSDIQLTQSPDSLAVSLGERATINCKAS
```

QSVDYDGDSYLNWYQQKPGQPPKLLIYDASNLVSGVPDRFSGSGSGTDFT

LTISSLQAADVAVYHCQQSTEDPWTFGQGTKVEIKR (Humanised CD19ALAb scFv sequence - Heavy 19, Kappa 7)
SEQ ID NO: 70
QVQLVQSGAEVKKPGASVKLSCKASGYAFSSYWMNWVRQAPGQSLEWIGQ

IWPGDGDTNYNGKFKGRATLTADESARTAYMELSSLRSGDTAVYFCARRE

TTTVGRYYYAMDYWGKGTLVTVSSDIQLTQSPDSLAVSLGERATINCKAS

QSVDYDGDSYLNWYQQKPGQPPKVLIYDASNLVSGVPDRFSGSGSGTDFT

LTISSLQAADVAVYYCQQSTEDPWTFGQGTKVEIKR

The scFv may be in a VH-VL orientation (as shown in SEQ ID NOs: 68, 69 and 70) or a VL-VH orientation.

The CAR of the present invention may comprise one of the following VH sequences:

(Murine CD19ALAb VH sequence)
SEQ ID NO: 71
QVQLQQSGAELVRPGSSVKISCKASGYAFSSYWMNWVKQRPGQGLEWIGQ

IWPGDGDTNYNGKFKGKATLTADESSSTAYMQLSSLASEDSAVYFCARRE

TTTVGRYYYAMDYWGQGTTVTVSS (Humanised CD19ALAb VH sequence)
SEQ ID NO: 72
QVQLVQSGAEVKKPGASVKLSCKASGYAFSSYWMNWVRQAPGQSLEWIGQ

IWPGDGDTNYNGKFKGRATLTADESARTAYMELSSLRSGDTAVYFCARRE

TTTVGRYYYAMDYWGKGTLVTVSS

An anti-CD19 CAR may comprise one of the following VL sequences:

(Murine CD19ALAb VL sequence)
SEQ ID NO: 73
DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW

TFGGGTKLEIK (Humanised CD19ALAb VL sequence, Kappa 16)
SEQ ID NO: 74
DIQLTQSPDSLAVSLGERATINCKASQSVDYDGDSYLNWYQQKPGQPPKW

YDASNLVSGVPDRFSGSGSGTDFTLTISSLQAADVAVYHCQQSTEDPWTF

GQGTKVEIKR (Humanised CD19ALAb VL sequence, Kappa 7)
SEQ ID NO: 75
DIQLTQSPDSLAVSLGERATINCKASQSVDYDGDSYLNWYQQKPGQPPKV

LIYDASNLVSGVPDRFSGSGSGTDFTLTISSLQAADVAVYYCQQSTEDPW

TFGQGTKVEIKR

The CAR may comprise a variant of the sequence shown as SEQ ID NO: 68 to 75 having at least 80, 85, 90, 95, 98 or 99% sequence identity, provided that the variant sequence retain the capacity to bind CD19 (when in conjunction with a complementary VL or VH domain, if appropriate).

The percentage identity between two polypeptide sequences may be readily determined by programs such as BLAST which is freely available at blast.ncbi.nlm.nih.gov.

3.3. CD22 Binders

CD22 has seven extracellular IgG-like domains, which are commonly identified as Ig domain 1 to Ig domain 7, with Ig domain 7 being most proximal to the B cell membrane and Ig domain 1 being the most distal from the Ig cell membrane.

The positions of the Ig domains in terms of the amino acid sequence of CD22 (uniprot.org/uniprot/P20273) are summarised in the following table:

| Ig domain | Amino acids |
|---|---|
| 7 | 20-138 |
| 6 | 143-235 |
| 5 | 242-326 |
| 4 | 331-416 |
| 3 | 419-500 |
| 2 | 505-582 |
| 1 | 593-676 |

Examples of anti-CD22 CARs with antigen-binding domains derived from m971, HA22 and BL22 scFvs are described by Haso et al. (Blood; 2013; 121(7)). The antibodies HA22 and BL22 bind to an epitope on Ig domain 5 of CD22.

Other anti-CD22 antibodies are known, such as the mouse anti-human CD22 antibodies 1D9-3, 3B4-13, 7G6-6, 6C4-6, 4D9-12, 5H4-9, 10C1-D9, 15G7-2, 2B12-8, 2C4-4 and 3E10-7; and the humanised anti-human CD22 antibodies LT22 and Inotuzumab (G5_44). Table 1 summarises the, VH, VL and CDR sequences (in bold and underlined) and the position of the target epitope on CD22 for each antibody.

TABLE 1

| Antibody | VH | VL | Position of epitope on CD22 |
|---|---|---|---|
| 1D9-3 | EVQLVESGGGLVQPKGSL<br>KLSCAASGFTFNTYAMH<br>WVRQAPGKGLEWVARIR<br>SKSSNYATYYADSVKDR<br>FTISRDDSQSMLYLQMNN<br>LKTEDTAMYYCVDYLY<br>AMDYWGQGTSVTVSS<br>(SEQ ID NO: 76) | DIVMTQSQKFMSTSVG<br>DRVSITCKASQNVRTA<br>VAWYQQKPGQSPKALI<br>YLASNRHTGVPDRFTG<br>SGSGTDFTLTISNVQSE<br>DLADYFCLQHWNYPF<br>TFGSGTKLEIK<br>(SEQ ID NO: 77) | Domain 1 and 2 |

TABLE 1-continued

| Antibody | VH | VL | Position of epitope on CD22 |
|---|---|---|---|
| 3B4-13 | QVQLQQSGAELVRPGAS VTLSCKASGYTFTDYEM HWVKQTPVHGLEWIGAI DPETGATAYNQKFKK AILTADKSSTAYMDLRS LTSEDSAVYYCTRYDYGS SPWFAYWGQGTLVTVSA (SEQ ID NO: 78) | QAVVTQESALTTSPGE TVTLTCRSSAGAVTTS NYANWVQEKPDHLFT GLIGGTNNRAPGVPAR FSGSLIGDKAALTITGA QTEDEAIYFCALWNSN HWVFGGGTKLTVL (SEQ ID NO: 79) | Domain 1 and 2 |
| 7G6-6 | QVQLQQPGAELVMPGAS VKLSCKASGYTFTSYWM HWVKQRPGQGLEWIGEI DPSDSYTNYNQKFKGKA TLTVDKSSTAYMQLSSL TSEDSAVYYCARGYYGS SSFDYWGQGTTLTVSS (SEQ ID NO: 80) | DIVMSQSPSSLAVSVGE KVTMSCKSSQSLLYSS NQKNYLAWYQQKPG QSPKLLIYWASTRESG VPDRFTGSGSGTDFTLT ISSVKAEDLAVYYCQQ YYSYTFGGGTKLEIK (SEQ ID NO: 81) | Domain 1 and 2 |
| 6C4-6 | QVQLKESGPGLVAPSQSL SITCTVSGFSLTSYGVHW VRQPPGKGLEWLVVIWS DGSTTYNSALKSRLSISK DNSKSQVFLKMNSLQTD DTAMYYCARHADDYGF AWFAYWGQGTLVTVSA (SEQ ID NO: 82) | DIQMTQSPASLSASVGE TVTITCRASENIYSYLA WYQQKQGKSPQLLVY NAKTLAEGVPSRFSGS GSGTQFSLKINSLQPED FGSYYCQHHYGTPPTF GGGTKLEIK (SEQ ID NO: 83) | Domain 3 |
| 4D9-12 | EFQLQQSGPELVKPGASV KISCKASGYSFTDYNMN WVKQSNGKSLEWIGVINP NYGTTSYNQKFKGKATL TVDQSSSTAYMQLNSLTS EDSAVYYCARSTTVVD WYFDVWGTGTTVTVSS (SEQ ID NO: 84) | DIQMTQSPSSLSASLGE RVSLTCRASQEISGYL SWLQQKPDGTIKRLIY AASTLDSGVPKRFSGS RSGSDYSLTISSLESEDF ADYYCLQYASYPFTFG SGTKLEIK (SEQ ID NO: 85) | Domain 4 |
| 5H4-9 | QVQVQQPGAELVRPGTS VKLSCKASGYTFTRYWM YWVKQRPGQGLEWIGVI DPSNDFTYYNQKFKGKA TLTVDTSSTAYMQLSSL TSEDSAVYYCARGYGSS YVGYWGQGTTLTVSS (SEQ ID NO: 86) | DVVMTQTPLSLPVSLG DQASISCRSSQSLVHSN GNTYLHWYLQKPGQS PKLLIYKVSNRFSGVP DRFSGSGSGTDFTLKIS RVEAEDLGVYFCSQST HVPPWTFGGGTKLEIK (SEQ ID NO: 87) | Domain 4 |
| 10C1-D9 | QVTLKESGPGILQSSQTLS LTCSFSGFSLSTSDMGVS WIRQPSGKGLEWLAHIY WDDDKRYNPSLKSRLTIS KDASRNQVFLKIATVDTA DTATYYCARSPWIYYGH YWCFDVWGTGTTVTVSS (SEQ ID NO: 88) | DIQMTQTTSSLSASLGD RVTISCRASQDISNYLN WYQQKPDGTVKLLIYY TSRLHSGVPSRFSGSGS GTDYSLTISNLEQEDIA TYFCQQGNTLPFTFGS GTKLEIK (SEQ ID NO: 89) | Domain 4 |
| 15G7-2 | QVQLQQSGAELVKPGAS VKLSCKASGYTFTEYTIH WVKQRSGQGLEWIGWFY PGSGSIKYNEKFKDKAT LTADKSSTVYMELSRLT SEDSAVYFCARHGDGYY LPPYYYFDYWGQGTTLTV SS (SEQ ID NO: 90) | QIVLTQSPAIMSASPGE KVTMTCSASSSVSYMY WYQQKPGSSPRLLIYD TSNLASGVPVRFSGSG SGTSYSLTISRMEADA ATYYCQQWSSYPLTF GAGTKLELK (SEQ ID NO: 91) | Domain 4 |
| 2B12-8 | QVQLQQSGAELARPGAS VKLSCKASGYIFTSYGIS WVKQRTGQGLEWIGEIY PRSGNTYYNEKFKGKAT LTADKSSTAYMELRSLT SEDSAVYFCARPIYYGSR EGFDYWGQGTTLTVSS (SEQ ID NO: 92) | DIVLTQSPATLSVTPGD SVSLSCRASQSISTNLH WYQQKSHASPRLLIKY ASQSVSGIPSRFSGSGS GTDFTLSINSVETEDFGI FFCQQSYSWPYTFGGG TKLEIK (SEQ ID NO: 93) | Domain 4 |

TABLE 1-continued

| Antibody | VH | VL | Position of epitope on CD22 |
|---|---|---|---|
| 2C4-4 | QVQLQQPGAELVMPGAS VKLSCKASGYTFTSYWM HWVKQRPGQGLEWIGEI DPSDSYTNYNQKFKGKS TLTVDKSSTAYIQLSSLT SEDSAVYYCARWASYRG YAMDYWGQGTSVTVSS (SEQ ID NO: 94) | DVLMTQTPLSLPVSLG DQASISCRSSQSIVHSN GNTYLEWYLQKPGQS PKLLIYKVSNRFSGVP DRFSGSESGTDFTLKIS RVEAEDLGVYYCFQG SHVPWTFGGGTKLEIK (SEQ ID NO: 95) | Domain 5-7 |
| 3E10-7 | EFQLQQSGPELVKPGASV KISCKASGYSFTDYNMN WVKQSNGKSLEWIGVINP NYGTTSYNQRFKGKATL TVDQSSSTAYMQLNSLTS EDSAVYYCARSGLRYWY FDVWGTGTTVTVSS (SEQ ID NO: 96) | DIQMTQSPSSLSASLGE RVSLTCRASQEISGYL SWLQQKPDGTIKRLIY AASTLDSGVPKRFSGS RSGSDYSLTISSLESEDF ADYYCLQYASYPFTFG SGTKLEIK (SEQ ID NO: 97) | Domain 5-7 |
| LT22 | EVQLVESGAEVKKPGSSV KVSCKASGYTFTNYWIN WVRQAPGQGLEWMGNI YPSDSFTNYNQKFKDRV TITADKSTSTVYLELRNLR SDDTAVYYCTRDTQERS WYFDVWGQGTLVTVSS (SEQ ID NO: 98) | DIVMTQSPATLSVSPGE RATLSCRSSQSLVHSN GNTYLHWYQQKPGQA PRLLIYKVSNRFSGVPA RFSGSGSGAEFTLTISSL QSEDFAVYYCSQSTHV PWTFGQGTRLEIKR (SEQ ID NO: 99) | Domain 5 |
| Inotuzumab G5_44 | EVQLVQSGAEVKKPGAS VKVSCKASGYRFTNYWI HWVRQAPGQGLEWIGGI NPGNNYATYRRKFQGR VTMTADTSTSTVYMELSS LRSEDTAVYYCTREGYG NYGAWFAYWGQGTLVT VSS (SEQ ID NO: 100) | DVQVTQSPSSLSASVG DRVTITCRSSQSLANSY GNTFLSWYLHKPGKA PQLLIYGISNRFSGVPD RFSGSGSGTDFTLTISSL QPEDFATYYCLQGTH QPYTFGQGTKVEIKR (SEQ ID NO: 101) | Domain 7 |
| 9A8-1 | EVQLVESGGGLVQPGRSL KLSCAASGFTFSNFAMA WVRQPPTKGLEWVASIST GGGNTYYRDSVKGRFTI SRDDAKNTQYLQMDSLR SEDTATYYCARQRNYYD GSYDYEGYTMDAWGQG TSVTVSS (SEQ ID NO: 102) | DIQMTQSPSSLSASLGD RVTITCRSSQDIGNYLT WFQQKVGRSPRRMIY GAIKLEDGVPSRFSGS RSGSDYSLTISSLESED VADYQCLQSIQYPFTF GSGTKLEIK (SEQ ID NO: 103) | Domains 1 and 2 |
| 1G3-4 | QVTLKESGPGILQPSQTLSL TCTFSGFSLSTSGMGVGWI RQPSGKGLEWLTNIWWDD DKNYNPSLKNRLTISKDTSI NQAFLKITNVDTADTATYYC ARIAHYFDGYYYVMDVWG QGTSVTVSS (SEQ ID NO: 99) | DIQMTQSPASLSASLGET VSIECLASGGISNDLAWY QQKSGKSPQLLIYAASR LQDGVPSRFSGSGSGTR YSLKISGMQSEDEADYF CQQSYKYPYTFGGGTKL ELK (SEQ ID NO: 100) | Domain 4 |

An antigen binding domain of a FabCAR which binds to CD22 may comprise the VH and/or VL sequence from any of the CD22 antibodies listed in table 1, or a variant thereof which has at least 70, 80, 90 or 90% sequence identity, which variant retains the capacity to bind CD22.

4. Nucleic Acid

The present invention also provides a nucleic acid sequence which encodes the CAR of the invention.

Where the CAR of the invention has, for example, an scFv or dAb antigen binding domain, the nucleic acid sequence which encodes the CAR of the invention may comprise the sequence:

AgB1-spacer1-TM1-endo1 wherein
- AgB is a nucleic acid sequence encoding the antigen-binding domain of the CAR;
- spacer is a nucleic acid sequence encoding the spacer of the CAR;
- TM is a nucleic acid sequence encoding the transmembrane domain of the CAR;
- endo is a nucleic acid sequence encoding the intracellular T cell signalling domain of the CAR.

4b. Nucleic Acid Construct

The present invention also provides a nucleic acid construct which encodes the CAR of the invention optionally together with another polypeptide, such as another CAR.

For example, where the CAR of the invention has a Fab antigen binding domain, a nucleic acid construct encoding the CAR may have the structure:

VH-CH-spacer-TM-endo-coexpr-VL-CL or
VL-CL-spacer-TM-endo-coexpr-VH-CH wherein:
- VH is a nucleic acid sequence encoding a heavy chain variable region;
- CH is a nucleic acid sequence encoding a heavy chain constant region
- spacer is a nucleic acid encoding a spacer;
- TM is a nucleic acid sequence encoding a transmembrane domain;
- endo is a nucleic acid sequence encoding an endodomain;
- coexpr is a nucleic acid sequence enabling co-expression of the first and second polypeptides;
- VL is a nucleic acid sequence encoding a light chain variable region; and
- CL is a nucleic acid sequence encoding a light chain constant region.

For both structures mentioned above, nucleic acid sequences encoding the two polypeptides may be in either order in the construct.

The particulars of the antigen binding domain, the spacer, the transmembrane domain and the intracellular T-cell signalling domain of the CAR were described in the context of the CAR of the invention and apply equally to the nucleic acid sequence which encodes the CAR of the invention.

There is also provided a nucleic acid construct encoding an OR gate, which comprises two of more CARs, at least one of which is a CAR according to the present invention.

A nucleic acid construct encoding a double OR gate may have the structure:

AgB1-spacer1-TM1-endo1-coexpr-AbB2-spacer2-TM2-endo2 wherein:
- AgB1 is a nucleic acid sequence encoding the antigen-binding domain of the first CAR, wherein the first CAR is the CAR according to the invention;
- spacer 1 is a nucleic acid sequence encoding the spacer of the first CAR;
- TM1 is a nucleic acid sequence encoding the transmembrane domain of the first CAR;
- endo1 is a nucleic acid sequence encoding the intracellular T cell signalling domain of the first CAR;
- coexpr is a nucleic acid sequence enabling co-expression of both CARs
- AgB2 is a nucleic acid sequence encoding the antigen-binding domain of the second CAR;
- spacer2 is a nucleic acid sequence encoding the spacer of the second CAR;
- TM2 is a nucleic acid sequence encoding the transmembrane domain of the second CAR;
- endo2 is a nucleic acid sequence encoding the intracellular T cell signalling domain of the second CAR.

The antigen binding domain AgB1 may be a Fab and the nucleic acid construct encoding the CAR may have the structure:

VH-CH-spacer1-TM1-endo1-coexpr1-VL-CL-coexpr2-AgB2-spacer2-TM2-endo2; or
VL-CL-spacer-TM1-endo1-coexpr1-VH-CH-coexpr2-AgB2-spacer2-TM2-endo2 wherein:
- VH is a nucleic acid sequence encoding a heavy chain variable region of the first CAR;
- CH is a nucleic acid sequence encoding a heavy chain constant region of the first CAR;
- Spacer 1 is a nucleic acid sequence encoding a spacer of the first CAR;
- TM1 is a nucleic acid sequence encoding a transmembrane domain of the first CAR;
- Endo1 is a nucleic acid sequence encoding an endodomain of the first CAR;
- Coexpr1and coexpr2, which may be the same or different, are nucleic acid sequences enabling co-expression of the first and second polypeptides of the first CAR; and the first and second CARs;
- VL is a nucleic acid sequence encoding a light chain variable region of the first CAR;
- CL is a nucleic acid sequence encoding a light chain constant region of the first CAR;
- AgB2 is a nucleic acid sequence encoding an antigen binding domain of the second CAR;
- Spacer2 is a nucleic acid sequence encoding a spacer of the second CAR;
- TM2 is a nucleic acid sequence encoding a transmembrane domain of the second CAR; and
- Endo2 is a nucleic acid sequence encoding an endodomain of the second CAR.

The antigen-binding domain of the second CAR may, for example, be an scFv or a dAb.

Alternatively, the antigen binding domain AgB2 of the second CAR may be a Fab. The antigen binding domain of the first CAR may, for example, be an scFv or a dAb. The nucleic acid construct encoding the CAR may have the structure:

AgB1-spacer1-TM1-endo1-coexpr1-VH-CH-spacer2-TM2-endo2-coexpr2-VL-CL; or
AgB1-spacer1-TM1-endo1-coexpr1-VL-CL-spacer2-TM2-endo2-coexpr2-VH-CH wherein:
- AgB1 is a nucleic acid sequence encoding an antigen binding domain of the first CAR;
- Spacer 1 is a nucleic acid sequence encoding a spacer of the first CAR;
- TM1 is a nucleic acid sequence encoding a transmembrane domain of the first CAR;

Endo1 is a nucleic acid sequence encoding an endodomain of the first CAR;

Coexpr1 and coexpr2, which may be the same or different, are nucleic acid sequences enabling co-expression of the first and second polypeptides of the first CAR; and the first and second CARs;

VL is a nucleic acid sequence encoding a light chain variable region of the second CAR;

CL is a nucleic acid sequence encoding a light chain constant region of the second CAR;

VH is a nucleic acid sequence encoding a heavy chain variable region of the second CAR;

CH is a nucleic acid sequence encoding a heavy chain constant region of the second CAR;

Spacer2 is a nucleic acid sequence encoding a spacer of the second CAR;

TM2 is a nucleic acid sequence encoding a transmembrane domain of the second CAR; and Endo2 is a nucleic acid sequence encoding an endodomain of the second CAR.

For the four structures mentioned above, nucleic acid sequences encoding the two polypeptides of the first CAR; and the nucleic acid sequences encoding the first and second CARs may be in any order in the construct.

There is also provided a nucleic acid construct encoding a triple OR gate, which comprises three CARs, one of which is a CAR according to the present invention.

A nucleic acid construct encoding a triple OR gate may have the structure:

AgB1-spacer1-TM1-endo1-coexpr1-VH-CH-spacer2-TM2-endo2-coexpr2-VL-CL-coexpr3-AgB3-spacer3-TM3-endo3; or AgB1-spacer1-TM1-endo1-coexpr1-VL-CL-spacer2-TM2-endo2-coexpr2-VH-CH-coexpr3-AgB3-spacer3-TM3 wherein:

AgB1 is a nucleic acid sequence encoding an antigen binding domain of the first CAR;

Spacer 1 is a nucleic acid sequence encoding a spacer of the first CAR;

TM1 is a nucleic acid sequence encoding a transmembrane domain of the first CAR;

Endo1 is a nucleic acid sequence encoding an endodomain of the first CAR;

Coexpr1, coexpr2 and coexpr3, which may be the same or different, are nucleic acid sequences enabling co-expression of the first and second polypeptides of the second CAR; and the first and third CARs;

VL is a nucleic acid sequence encoding a light chain variable region of the second CAR;

CL is a nucleic acid sequence encoding a light chain constant region of the second CAR;

VH is a nucleic acid sequence encoding a heavy chain variable region of the second CAR;

CH is a nucleic acid sequence encoding a heavy chain constant region of the second CAR;

Spacer2 is a nucleic acid sequence encoding a spacer of the second CAR;

TM2 is a nucleic acid sequence encoding a transmembrane domain of the second CAR;

Endo2 is a nucleic acid sequence encoding an endodomain of the second CAR;

AgB3 is a nucleic acid sequence encoding an antigen binding domain of the third CAR;

Spacer3 is a nucleic acid sequence encoding a spacer of the third CAR;

TM3 is a nucleic acid sequence encoding a transmembrane domain of the third CAR; and Endo3 is a nucleic acid sequence encoding an endodomain of the third CAR.

The antigen-binding domain of the first and third CARs may, for example, be an scFv or a dAb. In particular, one CAR may have a dAb antigen-binding domain and the other may have an scFv antigen binding domain.

Alternatively, the antigen binding domain AgB3 of the third CAR may be a Fab. The antigen binding domain of the first and second CARs may, for example, be an scFv or a dAb. The nucleic acid construct encoding the CAR may have the structure:

AgB1-spacer1-TM1-endo1-coexpr1-AgB2-spacer2-TM2-endo2-coexpr2-VH-CH-spacer3-TM2-endo3-coexpr3-VL-CL; or AgB1-spacer1-TM1-endo1-coexpr1-AgB2-spacer2-TM2-endo2-coexpr2-VL-CL-spacer3-TM2-endo3-coexpr3-VH-CH;

wherein:

AgB1 is a nucleic acid sequence encoding an antigen binding domain of the first CAR;

Spacer 1 is a nucleic acid sequence encoding a spacer of the first CAR;

TM1 is a nucleic acid sequence encoding a transmembrane domain of the first CAR;

Endo 1 is a nucleic acid sequence encoding an endodomain of the first CAR;

Coexpr1, coexpr2 and coexpr3, which may be the same or different, are nucleic acid sequences enabling co-expression of the first and second polypeptides of the third CAR; and the first and second CARs;

AgB2 is a nucleic acid sequence encoding an antigen binding domain of the second CAR;

Spacer2 is a nucleic acid sequence encoding a spacer of the second CAR;

TM2 is a nucleic acid sequence encoding a transmembrane domain of the second CAR;

Endo2 is a nucleic acid sequence encoding an endodomain of the second CAR;

VL is a nucleic acid sequence encoding a light chain variable region of the third CAR;

CL is a nucleic acid sequence encoding a light chain constant region of the third CAR;

VH is a nucleic acid sequence encoding a heavy chain variable region of the third CAR;

CH is a nucleic acid sequence encoding a heavy chain constant region of the third CAR;

Spacer3 is a nucleic acid sequence encoding a spacer of the third CAR;

TM3 is a nucleic acid sequence encoding a transmembrane domain of the third CAR; and Endo3 is a nucleic acid sequence encoding an endodomain of the third CAR;

In particular, the construct may be as illustrated in FIG. 4a. The construct may encode three CARs as illustrated in FIG. 4b, namely a dAb CAR against CD79, an scFv CAR against CD19 and a FabCAR against CD22.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

The nucleic acid sequences and constructs of the invention may contain alternative codons in regions of sequence encoding the same or similar amino acid sequences, in order to avoid homologous recombination.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

In the structure above, "coexpr" is a nucleic acid sequence enabling co-expression of two polypeptides as separate entities. It may be a sequence encoding a cleavage site, such that the nucleic acid construct produces both polypeptides, joined by a cleavage site(s). The cleavage site may be self-cleaving, such that when the polypeptide is produced, it is immediately cleaved into individual peptides without the need for any external cleavage activity.

The cleavage site may be any sequence which enables the two polypeptides to become separated.

The term "cleavage" is used herein for convenience, but the cleavage site may cause the peptides to separate into individual entities by a mechanism other than classical cleavage.

For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may, for example be a furin cleavage site, a Tobacco Etch Virus (TEV) cleavage site or encode a self-cleaving peptide.

A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within Trypanosoma spp and a bacterial sequence (Donnelly et al (2001) as above).

The cleavage site may comprise the 2A-like sequence shown as SEQ ID NO:104 (RAEGRGSLLTCGDVEENPGP).

5. Kit

The present invention also provides a kit, or kit of nucleic acid sequences or constructs, which comprises one or more nucleic acid sequences or constructs encoding a CAR according to the invention, a second CAR and, optionally, a third CAR as described in the context of the logic gates.

A kit according to the invention may comprise:
(i) a first nucleic acid sequence or construct which encodes the first CAR; and
(ii) a second nucleic acid sequence or construct encoding the second CAR as defined in the context of the logic gates;
and, optionally
(iii) a third nucleic acid sequence or construct encoding the third CAR as defined in the context of the logic gates.

The kit may contain alternative codons in regions of sequence encoding the same or similar amino acid sequences, in order to avoid homologous recombination.

6. Vector

The present invention also provides a vector, or kit of vectors, which comprises one or more nucleic acid sequence (s) encoding a CAR according to the invention. Such a vector may be used to introduce the nucleic acid sequence(s) into a host cell so that it expresses a chimeric polypeptide according to the first aspect of the invention.

The vector may, for example, be a plasmid or a viral vector, such as a retroviral vector or a lentiviral vector, or a transposon-based vector or synthetic mRNA.

The vector may be capable of transfecting or transducing a T cell or a NK cell.

7. Cell

The present invention provides a cell which comprises a chimeric antigen receptor of the invention. The cell may comprise two of more CARs, for example it may comprise a double or triple OR gate as described above.

The cell may comprise a nucleic acid or a vector of the present invention.

The cell may be a cytolytic immune cell such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumour cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+Treg cells have been described—naturally occurring Treg cells and adaptive Treg cells.

Naturally occurring Treg cells (also known as CD4+ CD25+FoxP3+Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr 1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The cells of the invention may be any of the cell types mentioned above.

T or NK cells according to the first aspect of the invention may either be created ex vivo either from a patient's own peripheral blood ($1^{st}$ party), or in the setting of a haematopoietic stem cell transplant from donor peripheral blood ($2^{nd}$ party), or peripheral blood from an unconnected donor ($3^{rd}$ party).

Alternatively, T or NK cells according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, chimeric polypeptide-expressing cells are generated by introducing DNA or RNA coding for the chimeric polypeptide by one of many means including transduction with a viral vector, transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the chimeric polypeptide according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding a chimeric polypeptide.

The T or NK cells may then by purified, for example, selected on the basis of expression of the antigen-binding domain of the antigen-binding polypeptide.

8. Pharmaceutical Composition

The present invention also relates to a pharmaceutical composition containing a plurality of cells according to the invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

9. Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The T or NK cell-containing sample may be isolated from a subject or from other sources, for example as described above. The T or NK cells may be isolated from a subject's own peripheral blood ($1^{st}$ party), or in the setting of a haematopoietic stem cell transplant from donor peripheral blood ($2^{nd}$ party), or peripheral blood from an unconnected donor ($3^{rd}$ party).

The present invention provides a cell comprising a CAR, a nucleic acid, a kit or a vector of the present invention for use in treating and/or preventing a disease. The cell may comprise two of more CARs, for example it may comprise a double or triple OR gate as described above.

The invention also relates to the use of a cell comprising a CAR, a nucleic acid, a kit or a vector of the present invention in the manufacture of a medicament for the treatment and/or prevention of a disease. The cell may comprise two of more CARs, for example it may comprise a double or triple OR gate as described above.

The disease to be treated and/or prevented by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The disease may be Multiple Myeloma (MM), B-cell Acute Lymphoblastic Leukaemia (B-ALL), Chronic Lymphocytic Leukaemia (CLL), Neuroblastoma, T-cell acute Lymphoblastic Leukaema (T-ALL) or diffuse large B-cell lymphoma (DLBCL).

The cells of the present invention may be capable of killing target cells, such as cancer cells. The target cell may be characterised by the presence of a tumour secreted ligand or chemokine ligand in the vicinity of the target cell. The target cell may be characterised by the presence of a soluble ligand together with the expression of a tumour-associated antigen (TAA) at the target cell surface.

The cells and pharmaceutical compositions of present invention may be for use in the treatment and/or prevention of the diseases described above.

This application claims the benefit of United Kingdom application No. 1807870.9 filed on 15 May 2018. This application is incorporated herein by reference in its entirety.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention will now be further described by way of Examples, which are meant to serve to assist one of ordinary skill in the art in carrying out the invention and are not intended in any way to limit the scope of the invention.

EXAMPLES

Example 1: Generation of Single Domain Antibodies Specific to CD79a or CD79b

In order to generate single domain antibodies (dAbs) specific to CD79a or CD79b, llamas are immunised with a combination of either CD79a- or CD79b-derived peptides and DNA.

Serum from immunised animals is isolated prior to and after each immunization to follow the immune response against the immunogen.

Blood samples of about 200 ml are taken from immunised llamas and enriched lymphocyte populations obtained via Ficoll discontinuous gradient centrifugation. From these cells, total RNA is isolated by acid guanidinium thiocyanate extraction. After first strand cDNA synthesis, DNA fragments encoding heavy chain variable fragments and part of the long or short hinge region are amplified by PCR. The amplified pool of single domain antibody sequences is digested using the restriction enzymes PstI and NotI, and ligated into the phagemid vector pSOS11.

Following construction of the single domain antibody phagemid library, antibodies are expressed on phage after infection with M13K07. The phage library is panned for the presence of binders respectively on solid-phase conjugated to CD79a or CD79b, or in solution with 100 nM biotinylated CD79a or biotinylated CD79b.

Following panning the whole phage library is assessed for enrichment against CD79a or CD79b by whole-phage ELISA. Individual phage clones are further screened for specificity and analysed to determine specific single domain antibody sequences.

Example 2: Generation of dAb CARs Specific to CD79a or CD79b

A second generation CAR is designed having a 41BB and CD3 zeta endodomain and an antigen binding domain comprising an anti-CD79a or anti-CD79b dAb, as described in Example 1. Primary human T-cells from normal donors are transduced with retroviral vectors expressing the anti-CD79 CAR or an irrelevant EGFRvIII CAR as a negative control. The capacity of the cells to kill either CD79-expressing target cells is investigated using flow cytometry.

T cell proliferation is measured after 72 hours of co-culture and release of cytokines such as IFNγ and IL-2 is measured after 24 hours of co-culture with CD79-expressing target cells.

Example 3: Investigation of Antigen-Negative Escape with CD79 CARs

NALM6 cells, i.e. a B-ALL cell line, are engineered by means of retroviral transduction and CrispR/CAS9 editing into different clones to obtain the following phenotypes:
CD19+CD22+CD79+, or
CD19+CD22-CD79+, or
CD19-CD22+CD179+, or
CD19-CD22-CD79+.

These clones are also engineered to express firefly Luciferase.

NSG mice are engrafted via tail vein injection with wild type NALM6 cells, the clones described above or mixtures thereof. Human T-cells transduced to express CD19 CAR, CD22 CAR, CD19 OR CD22 CAR, or CD19 OR CD22 OR CD79 CAR are administered to the mice via tail vein injection. Response of xenografts to CAR T-cells is initially determined by bioluminescence imaging. At fixed time-points, mice are sacrificed and residual NALM6 populations studied by flow-cytometry.

Example 4: Generation of Monoclonal Antibodies Specific to CD79a or CD79b

The nucleic acid sequences of CD79a and CD79b were cloned in the vector pVAC2 separated by a 2a self-cleaving peptide. 3× Wistar rats were immunized with plasmid DNA encoding CD79a/b heterodimer adsorbed to gold nanoparticles. A Gene-Gun™ (Biorad) system was used to deliver the coated gold nanoparticles intramuscularly. Rats were boosted 3 times over the course of 28 days. Test bleeds from the rats were screened for titres of anti-CD79b antibodies by ELISA and flow cytometry.

Rats with CD79b positive sera were selected for a final immunisation boost before the spleens were harvested for B cell isolation and hybridoma production. Hybridoma fusions of 10×96-well plates with lymphocytes from the selected rats were performed. Hybridoma supernatants were screened for reactive anti-CD79b antibodies by ELISA against recombinant human purified protein and a peptide representing the target region of interest. ELISA positive hybridoma supernatants were tested by flow cytometry on Daudi cells, which endogenously express CD79b. Candidate hybridomas were expanded.

Hybridomas expressing the strongest anti-CD79b response by flow cytometry were identified, expanded, and stocks cloned to generate monoclonal antibody secreting hybridomas. Hybridoma clones were obtained by limiting dilution.

Total RNA was isolated from monoclonal hybridoma cells using illustra RNAspin Mini kit (GE Healthcare, product number 25050071) according to the manufacturer's instructions. The total RNA was analysed by agarose gel electrophoresis and the concentration assessed using a NanoDrop2000C. Total RNA was reverse-transcribed into cDNA using Oligo(dT)20 and SuperScript™ II Reverse Transcriptase (ThermoFisher Scientific, product number 18064022) in the presence of template-switch oligo according to manufacturer's instructions. The antibody fragments of VH and VL were amplified using the 5'RACE PCR method. DNA fragments were cloned blunt-ended into vectors using CloneJET PCR Cloning Kit (ThermoFisher Scientific, product number K1231) according to manufacturer's instructions. Five colonies for each of the heavy and light chains were sequenced and a consensus sequence was obtained.

Example 5: Soluble Antibody Expression and Purification of anti-CD79b Antibodies Anti-CD79b antibodies were formatted into murine IgG2a Fc. Reformatted antibodies were expressed by transient expression on ExpiCHO cell lines following co-transfection of the relevant plasmid construct. The selected anti-CD79b antibodies that were expressed are Polatuzumab, and clones 2E8, 3H2, 4G11, 7G4, 9F1, and 10C11 that were obtained in Example 4.

Supernatant from transfected ExpiCHO cells was purified using protein A affinity chromatography. Briefly, a HiTrap MabSelect SuRE 1 ml column was equilibrated with 5 column volumes of PBS pH 7.4. Supernatant was applied to the column using Akta™ Pure system at a flow rate of 1 mL/min. Following application of supernatant, the column was washed with 20 column volumes of PBS. Bound protein was then eluted from the column with 3 ml of IgG elution buffer (Pierce, Cat. No. 21004) at 1 mL/min and directly loaded onto 2 HiTrap 5 ml desalting columns, previously equilibrated in PBS, and collected on a 96-well plate using a fraction collector unit. Purity of antibody product was determined via SDS-PAGE.

Example 6: Determination of the Binding Affinity for CD79b

Recombinant anti-CD79b antibodies Polatuzumab and newly generated antibodies 2E8, 3H2, and 7G4 were immobilised on individual flow cells on a Series S CM5 sensor chip (GE Healthcare) to a density of 150-280 RU using a Biacore 8K instrument. HBS-P+buffer was used as running buffer under all experimental conditions. Recombinant purified CD79b (R&D systems) at known concentrations was used as the 'analyte' and injected over the respective flow cells with 150s contact time and 300s dissociation, at 30 μl/minute of flow rate and a constant temperature of 25° C. In each experiment, flow cell 1 was unmodified and used for reference subtraction. A '0 concentration' sensorgram of buffer alone was used as a double reference subtraction to factor for drift. Data were fit to a 1:1 Langmuir binding model.

Results shown in Table 1 revealed that newly generated antibodies 2E8, 3H2, and 7G4 bound to CD79b with an affinity comparable to that of polatuzumab.

TABLE 1

Kinetics of the binding of anti-CD79b antibodies for CD79b.

| Antibody Clone | Quality Kinetics Chi$^2$ (RU$^2$) | 1:1 binding ka (1/Ms) | kd (1/s) | KD (M) |
| --- | --- | --- | --- | --- |
| Polatuzumab | 1.62e0 | $1.17 \times 10^6$ | $8.06 \times 10^{-3}$ | $6.88 \times 10^{-9}$ |
| 2E8 | 7.01e−2 | $1.13 \times 10^7$ | $8.05 \times 10^{-2}$ | $7.11 \times 10^{-9}$ |
| 7G4 | 1.62e0 | $2.12 \times 10^{10}$ | $6.56 \times 10^1$ | $3.10 \times 10^{-9}$ |
| 3H2 | 1.24e−1 | $1.64 \times 10^6$ | $4.31 \times 10^{-3}$ | $2.62 \times 10^{-9}$ |

Example 7: Assessment of Endogenous CD79b Expression on Cell Lines

Cell surface expression of CD79b on Raji, Daudi and MM1.s cell lines was determined via flow cytometry. Briefly, cells were stained with 5 μg/ml of anti-CD79b antibody polatuzumab and detected via anti-murine Fc secondary antibody conjugated to APC. Stained cells were acquired on a MACS quant X instrument.

Figure 5:
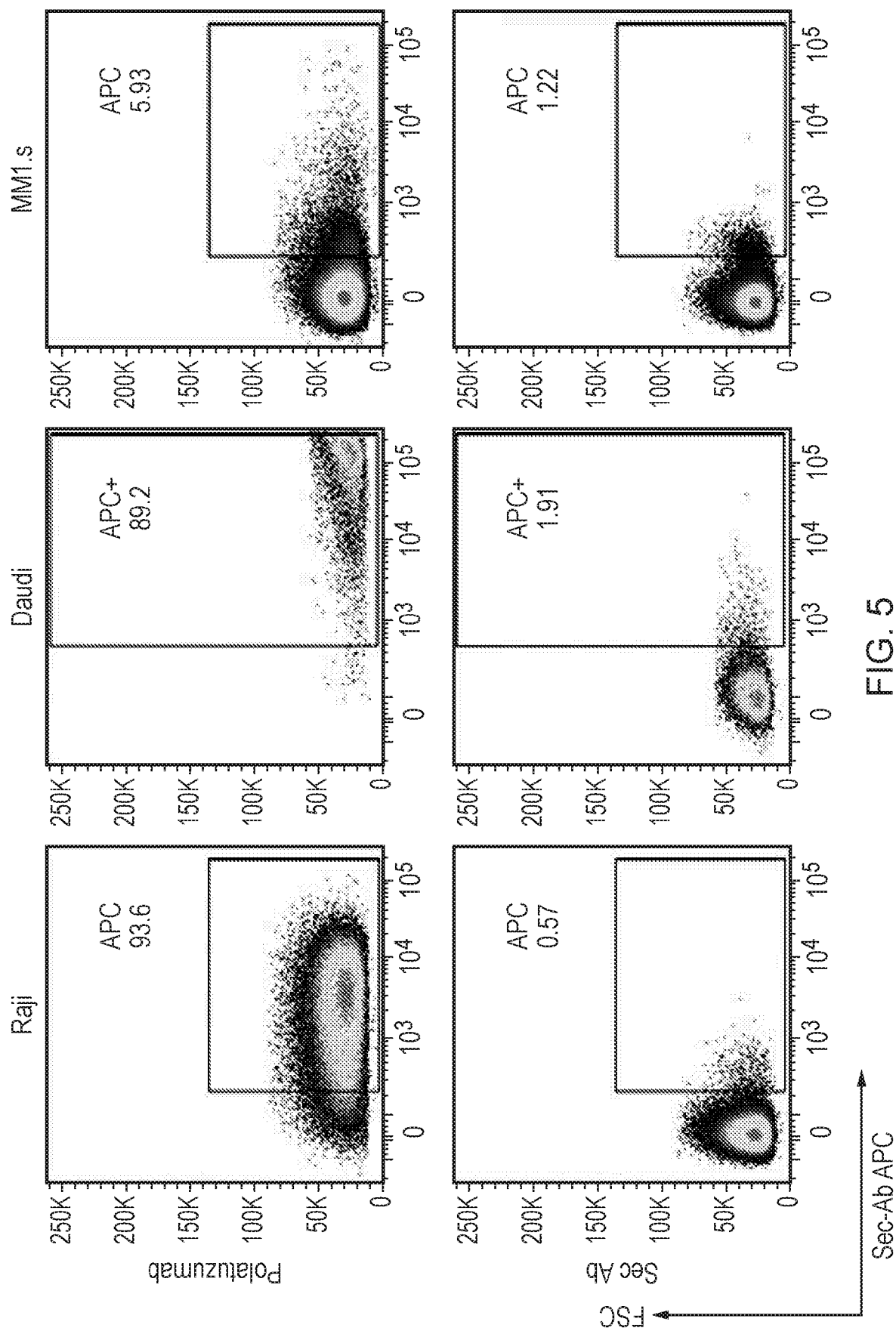
FIG. 5. Flow cytometry analysis of cell surface expression of CD79b on Raji, Daudi and MM1.s cell lines. Sec Ab: secondary antibody.

Results revealed that Raji cells expressed medium levels of CD79b antigen compared to Daudi or MM1.s cell lines, which expressed high and low levels of CD79b, respectively (FIG. 5).

Example 8: Generation of Anti-CD79b CAR

Second generation CAR constructs were generated based on anti-CD79b antibodies polatuzumab, 3H2 and 10C11 (FIG. 2c). CAR constructs were designed to include a scFv anti-CD79b extracellular binding domain linked to a human CD8 stalk spacer, CD8 transmembrane domain and 41BB-CD3z endodomains. These CAR constructs were cloned into a retroviral vector and used to transduce activated PBMCs obtained from four healthy donors.

Example 9: Functional Characterisation of Anti-CD79b CARs: Cytokine Production To assess the functional capacity of the anti-CD79b CAR-T cells towards CD79b, target cells (MM1.s or Raji cells) were co-incubated with antiCD79b CAR-T cells obtained from Example 8 at a 1:1 effector to target ratio. After 72 h, culture supernatants were collected and IFN-γ production measured by ELISA.

Figure 6:
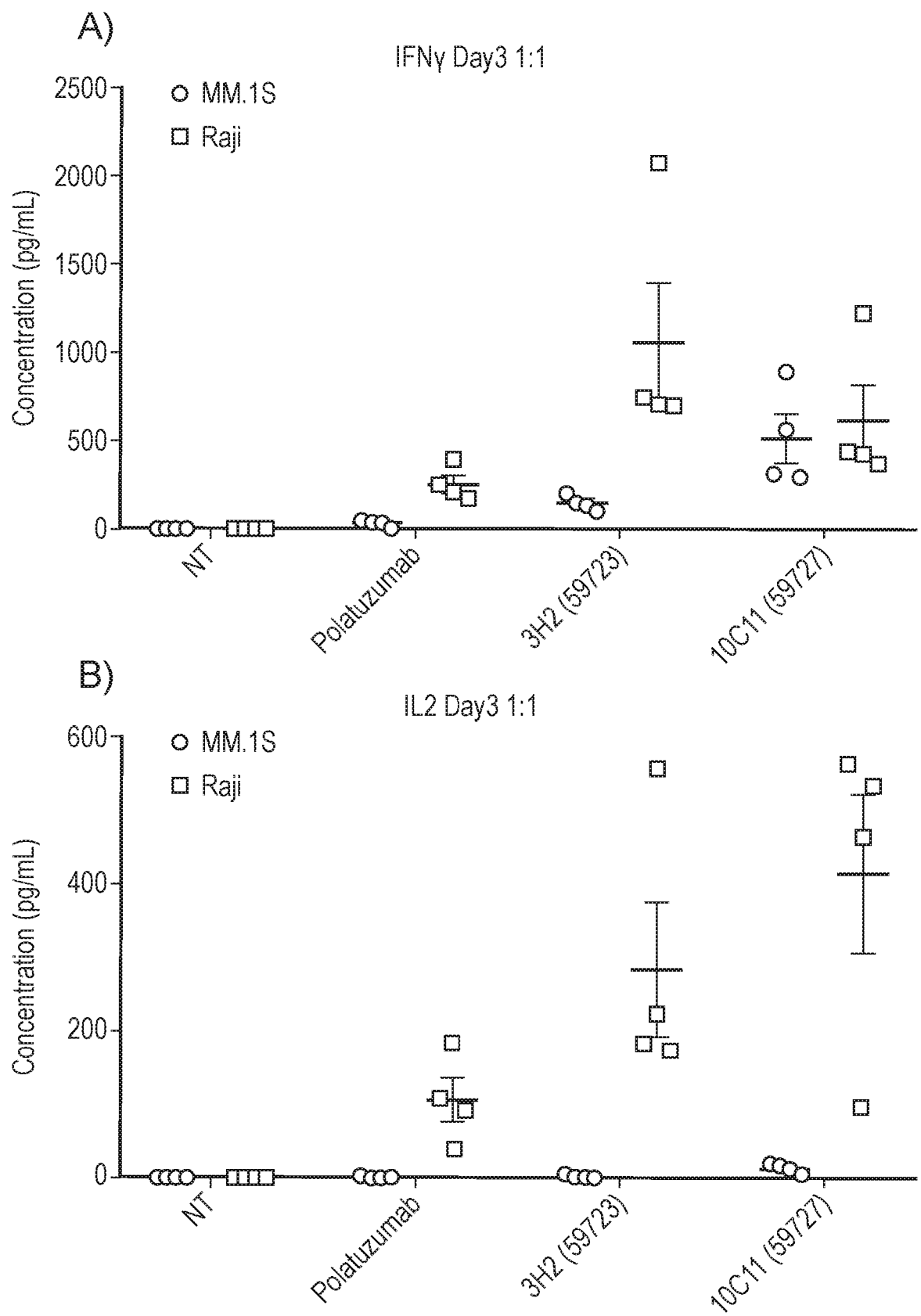
FIG. 6. Functional characterisation of anti-CD79b CARs. Production of (A) IFN-γ and (B) IL-2 by the anti-CD79b 3H2 and 10C11-based CAR-T cells incubated in the presence of MM1.s or Raji cells. A polatuzumab-based CAR was used as control.

In FIG. 6a, anti-CD79b 3H2 and 10C11-based CAR-T cells showed greater IFN-γ release compared to the polatuzumab-based CAR in both the low and medium CD79b expressing cells (MM1.s and Raji cells, respectively). Similarly, IL-2 production was higher for both 3H2 and 10C11-based CAR-T cells compared to the polatuzumab-based CAR, although this effect was more evident on the medium-expressing CD79b cells, i.e. Raji cells (FIG. 6b).

Example 10: Functional Characterisation of Anti-CD79b CARs: Killing Assay on Raji Cells To determine ability of the anti-CD79b CARs to kill CD79b-expressing cells, cytotoxicity assays were set up using Raji cells co-cultured with anti-CD79b 3H2 and 10C11-based CAR-T cells, using the polatuzumab-based CAR as control. CAR-T cells were cultured in a 1:1 (E:T) ratio with Raji cells. Target cell recovery was measured 72 hours post culture by flow cytometry and used to establish cytotoxic capacity of CAR-T cells.

Figure 7:
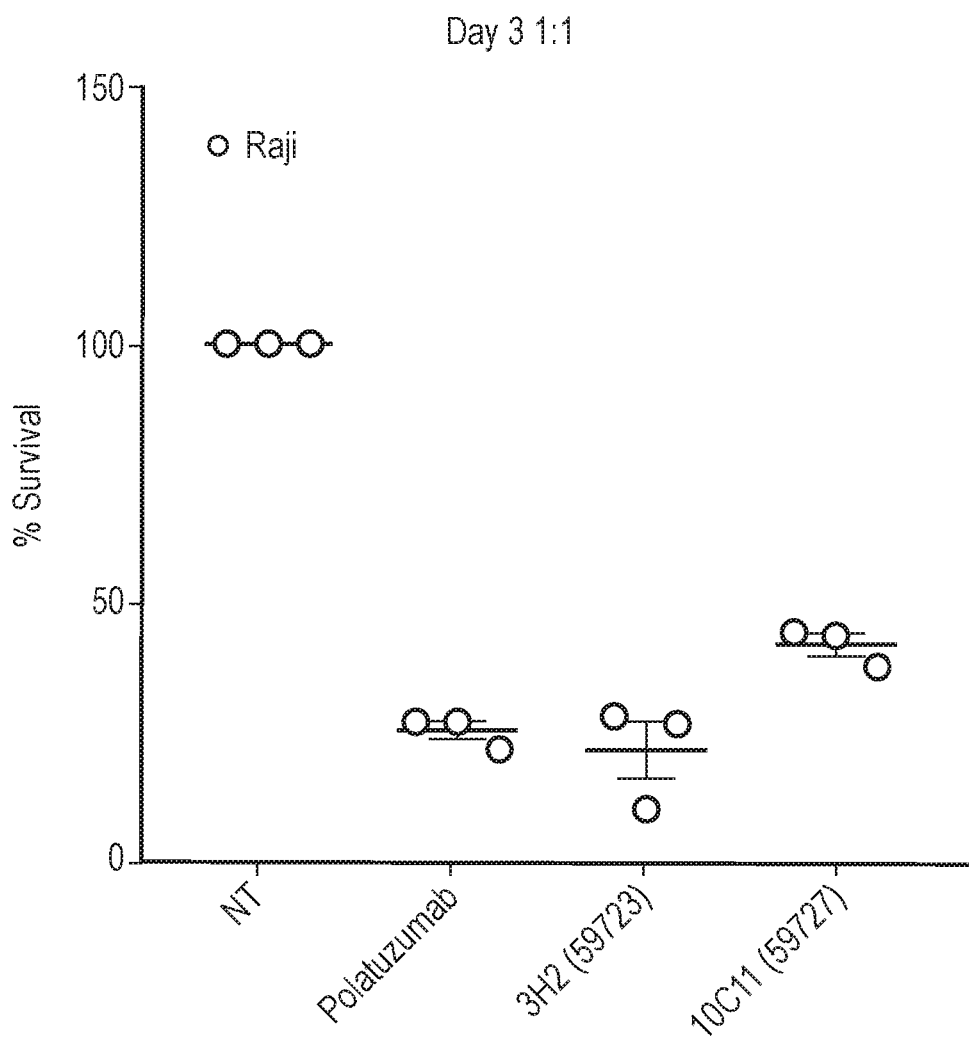
FIG. 7. Cytotoxic activity of the anti-CD79b 3H2 and 10C11-based CAR-T cells co-incubated with Raji cells. A polatuzumab-based CAR was used as control.

Cultures containing 3H2 or 10C11-based CAR-T cells showed a survival of Raji target cells that is comparable to that shown by cultures containing the control polatuzumab CAR-T cells (FIG. 7).

The invention claimed is:

1. A chimeric antigen receptor (CAR) which specifically binds the unspliced portion of the CD79B ectodomain shown as SEQ ID NO: 146 and which comprises an antigen-binding domain comprising:

a) a heavy chain variable region (VH) having complementarity determining regions (CDRs) with the following sequences:

```
                               (SEQ ID NO: 113)
        CDR1 - GFTFSNAA;

(SEQ ID NO: 114)
        CDR2 - IRTKPNNYAT;

(SEQ ID NO: 115)
        CDR3 - TYYDGSSYAMDA;
``` and
a light chain variable region (VL) having CDRs with the following sequences:

```
                               (SEQ ID NO: 116)
        CDR1 - QSLEYSDGYTY;

CDR2 - EVS;

(SEQ ID NO: 117)
        CDR3 - FQATHDPYT;
``` or
b) a VH having CDRs with the following sequences:

```
                               (SEQ ID NO: 121)
        CDR1 - GFTFSHTA;

(SEQ ID NO: 122)
        CDR2 - IRIQPKNYAT;

(SEQ ID NO: 123)
        CDR3 - TAAGFGFDY;
``` and
a VL having CDRs with the following sequences:

```
                               (SEQ ID NO: 124)
        CDR1 - QSLEYSDGNTY;

CDR2 - EVS;

(SEQ ID NO: 125)
        CDR3 - LQATHDPFT;
``` or
c) a VH having CDRs with the following sequences:

```
                               (SEQ ID NO: 113)
        CDR1 - GFTFSNAA;

(SEQ ID NO: 114)
        CDR2 - IRTKPNNYAT;

(SEQ ID NO: 129)
        CDR3 - TADGGYGFDY;
``` and
a VL having CDRs with the following sequences:

```
                               (SEQ ID NO: 116)
        CDR1 - QSLEYSDGYTY;

CDR2 - EVS;

(SEQ ID NO: 130)
        CDR3 - FQGTHDPYT;
``` or
d) a VH having CDRs with the following sequences:

```
                               (SEQ ID NO: 113)
        CDR1 - GFTFSNAA;

(SEQ ID NO: 114)
        CDR2 - IRTKPNNYAT;

(SEQ ID NO: 115)
        CDR3 - TYYDGSSYAMDA;
``` and
a VL having CDRs with the following sequences:

```
                               (SEQ ID NO: 116)
        CDR1 - QSLEYSDGYTY;

CDR2 - EIS;

(SEQ ID NO: 117)
        CDR3 - FQATHDPYT;
``` or
e) a VH having CDRs with the following sequences:

```
                               (SEQ ID NO: 136)
        CDR1 - GFTFSNTA;

(SEQ ID NO: 122)
        CDR2 - IRIQPKNYAT;

(SEQ ID NO: 123)
        CDR3 - TAAGFGFDY;
``` and
a VL having CDRs with the following sequences:

```
                               (SEQ ID NO: 137)
        CDR1 - QRLEYSDGNTY;

CDR2 - EVS;

(SEQ ID NO: 125)
        CDR3 - LQATHDPFT;
``` or
f) a VH having CDRs with the following sequences:

```
                               (SEQ ID NO: 141)
        CDR1 - GFTFSSAA;

(SEQ ID NO: 114)
        CDR2 - IRTKPNNYAT;

(SEQ ID NO: 115)
        CDR3 - TYYDGSSYAMDA;
``` and
a VL having CDRs with the following sequences:

CDR1-
QSLEYSDGYTY; (SEQ ID NO: 116)

CDR2-
EVS;

CDR3-
FQATHDPYT. (SEQ ID NO: 117)

2. The CAR according to claim 1, which comprises an antigen binding domain selected from a scFv and, a Fab.

3. The CAR according to claim 1, wherein the antigen-binding domain comprises a sequence selected from SEQ ID NO: 120, 128, 133, 135, 140 and 144.

* * * * *

SEQUENCE LISTING

```
<160> NUMBER OF SEQ ID NOS: 148

<210> SEQ ID NO 1
<211> LENGTH: 21
<212> TYPE: PRT
<213> ORGANISM: Artificial Sequence
<220> FEATURE:
<223> OTHER INFORMATION: signal peptide

<400> SEQUENCE: 1

Met Gly Thr Ser Leu Leu Cys Trp Met Ala Leu Cys Leu Leu Gly Ala
1               5                   10                  15

Asp His Ala Asp Gly
            20

<210> SEQ ID NO 2
<211> LENGTH: 21
<212> TYPE: PRT
<213> ORGANISM: Artificial Sequence
<220> FEATURE:
<223> OTHER INFORMATION: signal peptide

<400> SEQUENCE: 2

Met Ser Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 20
<212> TYPE: PRT
<213> ORGANISM: Artificial Sequence
<220> FEATURE:
<223> OTHER INFORMATION: signal peptide

<400> SEQUENCE: 3

Met Ala Val Pro Thr Gln Val Leu Gly Leu Leu Leu Leu Trp Leu Thr
1               5                   10                  15

Asp Ala Arg Cys
            20

<210> SEQ ID NO 4
<211> LENGTH: 20
<212> TYPE: PRT
<213> ORGANISM: Artificial Sequence
<220> FEATURE:
```

<223> OTHER INFORMATION: signal peptide

<400> SEQUENCE: 4

Met Glu Thr Asp Thr Leu Leu Leu Trp Val Leu Leu Leu Trp Val Pro
1               5                   10                  15

Gly Ser Thr Gly
            20

<210> SEQ ID NO 5
<211> LENGTH: 6
<212> TYPE: PRT
<213> ORGANISM: Artificial Sequence
<220> FEATURE:
<223> OTHER INFORMATION: heavy chain variable region (VH)
      complementarity determining region (CDR), CDR1

<400> SEQUENCE: 5

Ser Asp Tyr Ala Trp Asn
1               5

<210> SEQ ID NO 6
<211> LENGTH: 16
<212> TYPE: PRT
<213> ORGANISM: Artificial Sequence
<220> FEATURE:
<223> OTHER INFORMATION: VH CDR sequence, CDR2

<400> SEQUENCE: 6

Asn Ile Trp Tyr Ser Gly Ser Thr Thr Tyr Asn Pro Ser Leu Lys Ser
1               5                   10                  15

<210> SEQ ID NO 7
<211> LENGTH: 3
<212> TYPE: PRT
<213> ORGANISM: Artificial Sequence
<220> FEATURE:
<223> OTHER INFORMATION: VH CDR sequence, CDR3

<400> SEQUENCE: 7

Met Asp Phe
1

<210> SEQ ID NO 8
<211> LENGTH: 17
<212> TYPE: PRT
<213> ORGANISM: Artificial Sequence
<220> FEATURE:
<223> OTHER INFORMATION: light chain variable region (VL) CDR sequence,
      CDR1

<400> SEQUENCE: 8

Arg Ala Ser Glu Ser Val Asp Ser Tyr Gly Lys Thr Phe Met His Trp
1               5                   10                  15

His

<210> SEQ ID NO 9
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 9

Arg Val Ser Asn Leu Glu Ser
1               5

```
<210> SEQ ID NO 10
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 10

Gln Gln Ser Asn Glu Asp Pro Phe Thr
1               5

<210> SEQ ID NO 11
<211> LENGTH: 112
<212> TYPE: PRT
<213> ORGANISM: Artificial Sequence
<220> FEATURE:
<223> OTHER INFORMATION: VH sequence from murine monoclonal antibody

<400> SEQUENCE: 11

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Asn Ile Trp Tyr Ser Gly Ser Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ser Glu Asp Thr Ala Thr Tyr Tyr Cys
                85                  90                  95

Ser Arg Met Asp Phe Trp Gly Gln Gly Thr Thr Leu Thr Val Ser Ser
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: VL sequence from murine monoclonal antibody

<400> SEQUENCE: 12

Asp Ile Val Leu Thr Gln Ser Pro Pro Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Lys Thr Phe Met His Trp His Gln Gln Lys Pro Gly Gln Pro Pro
        35                  40                  45

Lys Leu Leu Ile Tyr Arg Val Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Phe Thr Phe Gly Gly Gly Thr Lys Leu Glu Ile Lys Arg
            100                 105                 110

<210> SEQ ID NO 13
<211> LENGTH: 245
<212> TYPE: PRT
```

<213> ORGANISM: Artificial Sequence
<220> FEATURE:
<223> OTHER INFORMATION: mouse anti-cynomolgus (Macaca fascicularis)
    CD79b 10D10 scFv sequence

<400> SEQUENCE: 13

Asp Ile Val Leu Thr Gln Ser Pro Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Lys Thr Phe Met His Trp His Gln Gln Lys Pro Gly Gln Pro Pro
        35                  40                  45

Lys Leu Leu Ile Tyr Arg Val Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Phe Thr Phe Gly Gly Gly Thr Lys Leu Glu Ile Lys Arg
            100                 105                 110

Ser Gly Gly Gly Gly Ser Gly Gly Gly Gly Ser Gly Gly Gly Gly Ser
        115                 120                 125

Gly Gly Gly Gly Ser Glu Val Gln Leu Gln Glu Ser Gly Pro Gly Leu
    130                 135                 140

Val Lys Pro Ser Gln Ser Leu Ser Leu Thr Cys Thr Val Thr Gly Tyr
145                 150                 155                 160

Ser Ile Thr Ser Asp Tyr Ala Trp Asn Trp Ile Arg Gln Phe Pro Gly
                165                 170                 175

Asn Lys Leu Glu Trp Met Gly Asn Ile Trp Tyr Ser Gly Ser Thr Thr
            180                 185                 190

Tyr Asn Pro Ser Leu Lys Ser Arg Ile Ser Ile Thr Arg Asp Thr Ser
        195                 200                 205

Lys Asn Gln Phe Phe Leu Gln Leu Asn Ser Val Thr Ser Glu Asp Thr
    210                 215                 220

Ala Thr Tyr Tyr Cys Ser Arg Met Asp Phe Trp Gly Gln Gly Thr Thr
225                 230                 235                 240

Leu Thr Val Ser Ser
                245

<210> SEQ ID NO 14
<211> LENGTH: 5
<212> TYPE: PRT
<213> ORGANISM: Artificial Sequence
<220> FEATURE:
<223> OTHER INFORMATION: VH CDR sequence, CDR1

<400> SEQUENCE: 14

Ser Tyr Trp Ile Glu
1               5

<210> SEQ ID NO 15
<211> LENGTH: 17
<212> TYPE: PRT
<213> ORGANISM: Artificial Sequence
<220> FEATURE:
<223> OTHER INFORMATION: VH CDR sequence, CDR2

<400> SEQUENCE: 15

Glu Ile Leu Pro Gly Gly Gly Asp Thr Asn Tyr Asn Glu Ile Phe Lys

-continued

```
1               5                   10                  15

Gly

<210> SEQ ID NO 16
<211> LENGTH: 8
<212> TYPE: PRT
<213> ORGANISM: Artificial Sequence
<220> FEATURE:
<223> OTHER INFORMATION: VH CDR sequence, CDR3

<400> SEQUENCE: 16

Arg Val Pro Val Tyr Phe Asp Tyr
1               5

<210> SEQ ID NO 17
<211> LENGTH: 15
<212> TYPE: PRT
<213> ORGANISM: Artificial Sequence
<220> FEATURE:
<223> OTHER INFORMATION: VL CDR sequence, CDR1

<400> SEQUENCE: 17

Lys Ala Ser Gln Ser Val Asp Tyr Asp Gly Asp Ser Phe Leu Asn
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 18

Ala Ala Ser Asn Leu Glu Ser
1               5

<210> SEQ ID NO 19
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 19

Gln Gln Ser Asn Glu Asp Pro Leu Thr
1               5

<210> SEQ ID NO 20
<211> LENGTH: 117
<212> TYPE: PRT
<213> ORGANISM: Artificial Sequence
<220> FEATURE:
<223> OTHER INFORMATION: VH sequence from murine monoclonal antibody

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
                20                  25                  30

Trp Ile Glu Trp Val Arg Gln Ala Pro Gly Lys Gly Leu Glu Trp Ile
            35                  40                  45

Gly Glu Ile Leu Pro Gly Gly Gly Asp Thr Asn Tyr Asn Glu Ile Phe
        50                  55                  60

Lys Gly Arg Ala Thr Phe Ser Ala Asp Thr Ser Lys Asn Thr Ala Tyr
```

```
                65                  70                  75                  80
Leu Gln Met Asn Ser Leu Arg Ala Glu Asp Thr Ala Val Tyr Tyr Cys
                        85                  90                  95

Thr Arg Arg Val Pro Val Tyr Phe Asp Tyr Trp Gly Gln Gly Thr Leu
                        100                 105                 110

Val Thr Val Ser Ser
            115

<210> SEQ ID NO 21
<211> LENGTH: 112
<212> TYPE: PRT
<213> ORGANISM: Artificial Sequence
<220> FEATURE:
<223> OTHER INFORMATION: VL sequence from murine monoclonal antibody

<400> SEQUENCE: 21

Asp Ile Gln Leu Thr Gln Ser Pro Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Phe Leu Asn Trp Tyr Gln Gln Lys Pro Gly Lys Ala Pro
                35                  40                  45

Lys Leu Leu Ile Tyr Ala Ala Ser Asn Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
                100                 105                 110

<210> SEQ ID NO 22
<211> LENGTH: 270
<212> TYPE: PRT
<213> ORGANISM: Artificial Sequence
<220> FEATURE:
<223> OTHER INFORMATION: humanised anti-CD79b-v17 scFv sequence

<400> SEQUENCE: 22

Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Ser Leu Ser
                20                  25                  30

Ala Ser Val Gly Asp Arg Val Thr Ile Thr Cys Lys Ala Ser Gln Ser
                35                  40                  45

Val Asp Tyr Asp Gly Asp Ser Phe Leu Asn Trp Tyr Gln Gln Lys Pro
        50                  55                  60

Gly Lys Ala Pro Lys Leu Leu Ile Tyr Ala Ala Ser Asn Leu Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
                100                 105                 110

Gln Gln Ser Asn Glu Asp Pro Leu Thr Phe Gly Gln Gly Thr Lys Val
            115                 120                 125

Glu Ile Lys Arg Ser Gly Gly Gly Gly Ser Gly Gly Gly Gly Ser Gly
        130                 135                 140
```

```
Gly Gly Gly Ser Gly Gly Gly Ser Glu Val Gln Leu Val Glu Ser
            145             150             155             160

Gly Gly Gly Leu Val Gln Pro Gly Gly Ser Leu Arg Leu Ser Cys Ala
                    165             170             175

Ala Ser Gly Tyr Thr Phe Ser Ser Tyr Trp Ile Glu Trp Val Arg Gln
            180             185             190

Ala Pro Gly Lys Gly Leu Glu Trp Ile Gly Glu Ile Leu Pro Gly Gly
                195             200             205

Gly Asp Thr Asn Tyr Asn Glu Ile Phe Lys Gly Arg Ala Thr Phe Ser
            210             215             220

Ala Asp Thr Ser Lys Asn Thr Ala Tyr Leu Gln Met Asn Ser Leu Arg
225             230             235             240

Ala Glu Asp Thr Ala Val Tyr Tyr Cys Thr Arg Arg Val Pro Val Tyr
                    245             250             255

Phe Asp Tyr Trp Gly Gln Gly Thr Leu Val Thr Val Ser Ser
            260             265             270

<210> SEQ ID NO 23
<211> LENGTH: 8
<212> TYPE: PRT
<213> ORGANISM: Artificial Sequence
<220> FEATURE:
<223> OTHER INFORMATION: VH CDR sequence, CDR3

<400> SEQUENCE: 23

Arg Val Pro Ile Arg Leu Asp Tyr
1               5

<210> SEQ ID NO 24
<211> LENGTH: 117
<212> TYPE: PRT
<213> ORGANISM: Artificial Sequence
<220> FEATURE:
<223> OTHER INFORMATION: VH sequence from murine monoclonal antibody

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
                20                  25                  30

Trp Ile Glu Trp Val Arg Gln Ala Pro Gly Lys Gly Leu Glu Trp Ile
            35                  40                  45

Gly Glu Ile Leu Pro Gly Gly Gly Asp Thr Asn Tyr Asn Glu Ile Phe
        50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                    85                  90                  95

Thr Arg Arg Val Pro Ile Arg Leu Asp Tyr Trp Gly Gln Gly Thr Leu
                100                 105                 110

Val Thr Val Ser Ser
            115

<210> SEQ ID NO 25
<211> LENGTH: 250
<212> TYPE: PRT
<213> ORGANISM: Artificial Sequence
<220> FEATURE:
<223> OTHER INFORMATION: humanised anti-CD79b v18 scFv sequence
```

-continued

<400> SEQUENCE: 25

Asp Ile Gln Leu Thr Gln Ser Pro Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Phe Leu Asn Trp Tyr Gln Gln Lys Pro Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Ser Gly Gly Gly Gly Ser Gly Gly Gly Ser Gly Gly Gly Gly Ser
            115                 120                 125

Gly Gly Gly Gly Ser Glu Val Gln Leu Val Glu Ser Gly Gly Gly Leu
    130                 135                 140

Val Gln Pro Gly Gly Ser Leu Arg Leu Ser Cys Ala Ala Ser Gly Tyr
145                 150                 155                 160

Thr Phe Ser Ser Tyr Trp Ile Glu Trp Val Arg Gln Ala Pro Gly Lys
                165                 170                 175

Gly Leu Glu Trp Ile Gly Glu Ile Leu Pro Gly Gly Gly Asp Thr Asn
            180                 185                 190

Tyr Asn Glu Ile Phe Lys Gly Arg Ala Thr Phe Ser Ala Asp Thr Ser
        195                 200                 205

Lys Asn Thr Ala Tyr Leu Gln Met Asn Ser Leu Arg Ala Glu Asp Thr
    210                 215                 220

Ala Val Tyr Tyr Cys Thr Arg Arg Val Pro Ile Arg Leu Asp Tyr Trp
225                 230                 235                 240

Gly Gln Gly Thr Leu Val Thr Val Ser Ser
                245                 250

<210> SEQ ID NO 26
<211> LENGTH: 15
<212> TYPE: PRT
<213> ORGANISM: Artificial Sequence
<220> FEATURE:
<223> OTHER INFORMATION: VL CDR sequence, CDR1

<400> SEQUENCE: 26

Lys Ala Ser Gln Ser Val Asp Tyr Glu Gly Asp Ser Phe Leu Asn
1               5                   10                  15

<210> SEQ ID NO 27
<211> LENGTH: 112
<212> TYPE: PRT
<213> ORGANISM: Artificial Sequence
<220> FEATURE:
<223> OTHER INFORMATION: VL sequence from murine monoclonal antibody

<400> SEQUENCE: 27

Asp Ile Gln Leu Thr Gln Ser Pro Ser Leu Ser Ala Ser Val Gly
1               5                   10                  15

Asp Arg Val Thr Ile Thr Cys Lys Ala Ser Gln Ser Val Asp Tyr Glu
            20                  25                  30

```
Gly Asp Ser Phe Leu Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
 50                      55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Leu Thr Phe Gly Gln Gly Thr Lys Val Glu Ile Lys Arg
                100                 105                 110
```

<210> SEQ ID NO 28
<211> LENGTH: 270
<212> TYPE: PRT
<213> ORGANISM: Artificial Sequence
<220> FEATURE:
<223> OTHER INFORMATION: humanised anti-CD79b v28 scFv sequence

<400> SEQUENCE: 28

```
Met Glu Thr Asp Thr Leu Leu Leu Trp Val Leu Leu Leu Trp Val Pro
 1               5                  10                  15

Gly Ser Thr Gly Asp Ile Gln Leu Thr Gln Ser Pro Ser Ser Leu Ser
                20                  25                  30

Ala Ser Val Gly Asp Arg Val Thr Ile Thr Cys Lys Ala Ser Gln Ser
            35                  40                  45

Val Asp Tyr Glu Gly Asp Ser Phe Leu Asn Trp Tyr Gln Gln Lys Pro
 50                      55                  60

Gly Lys Ala Pro Lys Leu Leu Ile Tyr Ala Ala Ser Asn Leu Glu Ser
 65                  70                  75                  80

Gly Val Pro Ser Arg Phe Ser Gly Ser Gly Ser Gly Thr Asp Phe Thr
                 85                  90                  95

Leu Thr Ile Ser Ser Leu Gln Pro Glu Asp Phe Ala Thr Tyr Tyr Cys
                100                 105                 110

Gln Gln Ser Asn Glu Asp Pro Leu Thr Phe Gly Gln Gly Thr Lys Val
            115                 120                 125

Glu Ile Lys Arg Ser Gly Gly Gly Gly Ser Gly Gly Gly Gly Ser Gly
130                 135                 140

Gly Gly Ser Gly Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Tyr Thr Phe Ser Ser Tyr Trp Ile Glu Trp Val Arg Gln
            180                 185                 190

Ala Pro Gly Lys Gly Leu Glu Trp Ile Gly Glu Ile Leu Pro Gly Gly
        195                 200                 205

Gly Asp Thr Asn Tyr Asn Glu Ile Phe Lys Gly Arg Ala Thr Phe Ser
210                 215                 220

Ala Asp Thr Ser Lys Asn Thr Ala Tyr Leu Gln Met Asn Ser Leu Arg
225                 230                 235                 240

Ala Glu Asp Thr Ala Val Tyr Tyr Cys Thr Arg Arg Val Pro Ile Arg
                245                 250                 255

Leu Asp Tyr Trp Gly Gln Gly Thr Leu Val Thr Val Ser Ser
            260                 265                 270
```

<210> SEQ ID NO 29
<211> LENGTH: 15

```
<212> TYPE: PRT
<213> ORGANISM: Artificial Sequence
<220> FEATURE:
<223> OTHER INFORMATION: VL CDR sequence, CDR1

<400> SEQUENCE: 29

Lys Ala Ser Gln Ser Val Asp Tyr Ser Gly Asp Ser Phe Leu Asn
1               5                   10                  15

<210> SEQ ID NO 30
<211> LENGTH: 112
<212> TYPE: PRT
<213> ORGANISM: Artificial Sequence
<220> FEATURE:
<223> OTHER INFORMATION: VL sequence from murine monoclonal antibody

<400> SEQUENCE: 30

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ser
            20                  25                  30

Gly Asp Ser Phe Leu Asn Trp Tyr Gln Gln Lys Pro Gly Lys Ala Pro
        35                  40                  45

Lys Leu Phe Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

<210> SEQ ID NO 31
<211> LENGTH: 270
<212> TYPE: PRT
<213> ORGANISM: Artificial Sequence
<220> FEATURE:
<223> OTHER INFORMATION: humanised anti-CD79b v32 scFv sequence

<400> SEQUENCE: 31

Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Ser Leu Ser
            20                  25                  30

Ala Ser Val Gly Asp Arg Val Thr Ile Thr Cys Lys Ala Ser Gln Ser
        35                  40                  45

Val Asp Tyr Ser Gly Asp Ser Phe Leu Asn Trp Tyr Gln Gln Lys Pro
    50                  55                  60

Gly Lys Ala Pro Lys Leu Phe Ile Tyr Ala Ala Ser Asn Leu Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln Ser Asn Glu Asp Pro Leu Thr Phe Gly Gln Gly Thr Lys Val
        115                 120                 125

Glu Ile Lys Arg Ser Gly Gly Gly Gly Ser Gly Gly Gly Gly Ser Gly
    130                 135                 140

Gly Gly Ser Gly Gly Gly Gly Ser Glu Val Gln Leu Val Glu Ser
```

-continued

```
            145                 150                 155                 160
Gly Gly Gly Leu Val Gln Pro Gly Gly Ser Leu Arg Leu Ser Cys Ala
                    165                 170                 175
Ala Ser Gly Tyr Thr Phe Ser Ser Tyr Trp Ile Glu Trp Val Arg Gln
                    180                 185                 190
Ala Pro Gly Lys Gly Leu Glu Trp Ile Gly Glu Ile Leu Pro Gly Gly
                    195                 200                 205
Gly Asp Thr Asn Tyr Asn Glu Ile Phe Lys Gly Arg Ala Thr Phe Ser
                    210                 215                 220
Ala Asp Thr Ser Lys Asn Thr Ala Tyr Leu Gln Met Asn Ser Leu Arg
225                 230                 235                 240
Ala Glu Asp Thr Ala Val Tyr Tyr Cys Thr Arg Arg Val Pro Ile Arg
                    245                 250                 255
Leu Asp Tyr Trp Gly Gln Gly Thr Leu Val Thr Val Ser Ser
                    260                 265                 270

<210> SEQ ID NO 32
<211> LENGTH: 117
<212> TYPE: PRT
<213> ORGANISM: Artificial Sequence
<220> FEATURE:
<223> OTHER INFORMATION: VH sequence from murine monoclonal antibody

<400> SEQUENCE: 32

Glu Val Gln Leu Gln Gln Ser Gly Ala Glu Leu Met Lys Pro Gly Ala
1               5                   10                  15
Ser Val Lys Ile Ser Cys Lys Ala Thr Gly Tyr Thr Phe Ser Ser Tyr
                20                  25                  30
Trp Ile Glu Trp Val Lys Gln Arg Pro Gly His Gly Leu Glu Trp Ile
            35                  40                  45
Gly Glu Ile Leu Pro Gly Gly Gly Asp Thr Asn Tyr Asn Glu Ile Phe
        50                  55                  60
Lys Gly Lys Ala Thr Phe Thr Ala Asp Thr Ser Ser Asn Thr Ala Tyr
65                  70                  75                  80
Met Gln Leu Ser Ser Leu Thr Ser Glu Asp Ser Ala Val Tyr Tyr Cys
                85                  90                  95
Thr Arg Arg Val Pro Val Tyr Phe Asp Tyr Trp Gly Gln Gly Thr Ser
                100                 105                 110
Val Thr Val Ser Ser
        115

<210> SEQ ID NO 33
<211> LENGTH: 112
<212> TYPE: PRT
<213> ORGANISM: Artificial Sequence
<220> FEATURE:
<223> OTHER INFORMATION: VL sequence from murine monoclonal antibody

<400> SEQUENCE: 33

Asp Ile Val Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
                20                  25                  30
Gly Asp Ser Phe Leu Asn Trp Tyr Gln Gln Lys Pro Gly Gln Pro Pro
            35                  40                  45
Lys Leu Phe Ile Tyr Ala Ala Ser Asn Leu Glu Ser Gly Ile Pro Ala
        50                  55                  60
```

```
Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                 85                  90                  95

Glu Asp Pro Leu Thr Phe Gly Ala Gly Thr Glu Leu Glu Leu Lys Arg
            100                 105                 110

<210> SEQ ID NO 34
<211> LENGTH: 270
<212> TYPE: PRT
<213> ORGANISM: Artificial Sequence
<220> FEATURE:
<223> OTHER INFORMATION: murine anti-CD79b SN8 scFv sequence

<400> SEQUENCE: 34

Met Glu Thr Asp Thr Leu Leu Leu Trp Val Leu Leu Leu Trp Val Pro
  1               5                  10                  15

Gly Ser Thr Gly Asp Ile Val Leu Thr Gln Ser Pro Ala Ser Leu Ala
                 20                  25                  30

Val Ser Leu Gly Gln Arg Ala Thr Ile Ser Cys Lys Ala Ser Gln Ser
             35                  40                  45

Val Asp Tyr Asp Gly Asp Ser Phe Leu Asn Trp Tyr Gln Gln Lys Pro
 50                  55                  60

Gly Gln Pro Pro Lys Leu Phe Ile Tyr Ala Ala Ser Asn Leu Glu Ser
 65                  70                  75                  80

Gly Ile Pro Ala Arg Phe Ser Gly Ser Gly Ser Gly Thr Asp Phe Thr
                 85                  90                  95

Leu Asn Ile His Pro Val Glu Glu Glu Asp Ala Ala Thr Tyr Tyr Cys
            100                 105                 110

Gln Gln Ser Asn Glu Asp Pro Leu Thr Phe Gly Ala Gly Thr Glu Leu
        115                 120                 125

Glu Leu Lys Arg Ser Gly Gly Gly Gly Ser Gly Gly Gly Gly Ser Gly
130                 135                 140

Gly Gly Ser Gly Gly Gly Gly Ser Glu Val Gln Leu Gln Gln Ser
145                 150                 155                 160

Gly Ala Glu Leu Met Lys Pro Gly Ala Ser Val Lys Ile Ser Cys Lys
                165                 170                 175

Ala Thr Gly Tyr Thr Phe Ser Ser Tyr Trp Ile Glu Trp Val Lys Gln
            180                 185                 190

Arg Pro Gly His Gly Leu Glu Trp Ile Gly Glu Ile Leu Pro Gly Gly
        195                 200                 205

Gly Asp Thr Asn Tyr Asn Glu Ile Phe Lys Gly Lys Ala Thr Phe Thr
    210                 215                 220

Ala Asp Thr Ser Ser Asn Thr Ala Tyr Met Gln Leu Ser Ser Leu Thr
225                 230                 235                 240

Ser Glu Asp Ser Ala Val Tyr Tyr Cys Thr Arg Arg Val Pro Val Tyr
                245                 250                 255

Phe Asp Tyr Trp Gly Gln Gly Thr Ser Val Thr Val Ser Ser
            260                 265                 270

<210> SEQ ID NO 35
<211> LENGTH: 5
<212> TYPE: PRT
<213> ORGANISM: Artificial Sequence
<220> FEATURE:
<223> OTHER INFORMATION: VH CDR sequence, CDR3

<400> SEQUENCE: 35
```

Tyr Ala Met Asp Tyr
1               5

<210> SEQ ID NO 36
<211> LENGTH: 113
<212> TYPE: PRT
<213> ORGANISM: Artificial Sequence
<220> FEATURE:
<223> OTHER INFORMATION: VH sequence from murine monoclonal antibody

<400> SEQUENCE: 36

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Lys Gln Arg Pro Gly Gln Gly Leu Gln Trp Ile
            35                  40                  45

Gly Arg Ile Tyr Pro Gly Ser Gly Ser Thr Asn Tyr Gln Lys Phe Lys
        50                  55                  60

Gly Lys Ala Thr Leu Thr Val Asp Lys Ser Ser Thr Ala Tyr Met
65                  70                  75                  80

Glu Leu Arg Ser Leu Thr Ser Glu Asn Ser Ala Val Tyr Tyr Cys Ala
                85                  90                  95

Arg Tyr Ala Met Asp Tyr Thr Gly Gln Gly Thr Ser Val Thr Val Ser
            100                 105                 110

Ser

<210> SEQ ID NO 37
<211> LENGTH: 113
<212> TYPE: PRT
<213> ORGANISM: Artificial Sequence
<220> FEATURE:
<223> OTHER INFORMATION: VL sequence from murine monoclonal antibody

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Pro Ser Gly Val Pro
        50                  55                  60

Asn Arg Phe Ser Gly Ser Gly Ser Gly Thr Asp Phe Thr Leu Lys Ile
65                  70                  75                  80

Ser Arg Val Gln Ala Glu Asn Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg

<210> SEQ ID NO 38
<211> LENGTH: 267
<212> TYPE: PRT
<213> ORGANISM: Artificial Sequence
<220> FEATURE:
<223> OTHER INFORMATION: murine anti-CD79a scFv sequence

<400> SEQUENCE: 38

Met Glu Thr Asp Thr Leu Leu Leu Trp Val Leu Leu Leu Trp Val Pro
1               5                   10                  15

Gly Ser Thr Gly Asp Val Leu Met Thr Gln Thr Pro Leu Ser Leu Pro
                20                  25                  30

Val Ser Leu Gly Asp Gln Ala Ser Ile Ser Cys Arg Ser Ser Gln Ser
            35                  40                  45

Ile Val His Ser Asn Gly Asn Thr Tyr Leu Glu Trp Tyr Leu Gln Lys
        50                  55                  60

Pro Gly Gln Ser Pro Lys Leu Leu Ile Tyr Lys Val Ser Asn Arg Pro
65                  70                  75                  80

Ser Gly Val Pro Asn Arg Phe Ser Gly Ser Gly Ser Gly Thr Asp Phe
                85                  90                  95

Thr Leu Lys Ile Ser Arg Val Gln Ala Gln Asn Leu Gly Val Tyr Tyr
            100                 105                 110

Cys Phe Gln Gly Ser His Val Pro Trp Thr Phe Gly Gly Gly Thr Lys
            115                 120                 125

Leu Glu Ile Lys Arg Ser Gly Gly Gly Ser Gly Gly Gly Gly Gly Ser
        130                 135                 140

Gly Gly Gly Gly Ser Gly Gly Gly Ser Gln Val Gln Leu Gln Gln
145                 150                 155                 160

Ser Gly Pro Glu Leu Val Lys Pro Gly Ala Ser Val Lys Ile Ser Cys
                165                 170                 175

Lys Ala Ser Gly Tyr Thr Phe Thr Asn Tyr Gly Met Asn Trp Val Lys
            180                 185                 190

Gln Arg Pro Gly Gln Gly Leu Gln Trp Ile Gly Arg Ile Tyr Pro Gly
        195                 200                 205

Ser Gly Ser Thr Asn Tyr Gln Lys Phe Lys Gly Lys Ala Thr Leu Thr
        210                 215                 220

Val Asp Lys Ser Ser Ser Thr Ala Tyr Met Glu Leu Arg Ser Leu Thr
225                 230                 235                 240

Ser Glu Asn Ser Ala Val Tyr Tyr Cys Ala Arg Tyr Ala Met Asp Tyr
                245                 250                 255

Thr Gly Gln Gly Thr Ser Val Thr Val Ser Ser
            260                 265

<210> SEQ ID NO 39
<211> LENGTH: 106
<212> TYPE: PRT
<213> ORGANISM: Artificial Sequence
<220> FEATURE:
<223> OTHER INFORMATION: kappa chain constant domain

<400> SEQUENCE: 39

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 40
<211> LENGTH: 97
<212> TYPE: PRT
<213> ORGANISM: Artificial Sequence
<220> FEATURE:
<223> OTHER INFORMATION: sequence from a gamma immunoglobulin heavy
      chain

<400> SEQUENCE: 40

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val

<210> SEQ ID NO 41
<211> LENGTH: 234
<212> TYPE: PRT
<213> ORGANISM: Artificial Sequence
<220> FEATURE:
<223> OTHER INFORMATION: spacer sequence, hinge-CH2CH3 of human IgG1

<400> SEQUENCE: 41

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr

```
                    180                 185                 190
Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys Lys Asp
225                 230

<210> SEQ ID NO 42
<211> LENGTH: 46
<212> TYPE: PRT
<213> ORGANISM: Artificial Sequence
<220> FEATURE:
<223> OTHER INFORMATION: spacer sequence, human CD8 stalk

<400> SEQUENCE: 42

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 43
<211> LENGTH: 20
<212> TYPE: PRT
<213> ORGANISM: Artificial Sequence
<220> FEATURE:
<223> OTHER INFORMATION: spacer sequence, human IgG1 hinge

<400> SEQUENCE: 43

Ala Glu Pro Lys Ser Pro Asp Lys Thr His Thr Cys Pro Pro Cys Pro
1               5                   10                  15

Lys Asp Pro Lys
            20

<210> SEQ ID NO 44
<211> LENGTH: 185
<212> TYPE: PRT
<213> ORGANISM: Artificial Sequence
<220> FEATURE:
<223> OTHER INFORMATION: spacer sequence, CD2 ectodomain

<400> SEQUENCE: 44

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
            35                  40                  45

Lys Glu Lys Glu Thr Phe Lys Glu Lys Asp Thr Tyr Lys Leu Phe Lys
        50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
            115                 120                 125
```

```
Asp Pro Glu Leu Asn Leu Tyr Gln Asp Gly Lys His Leu Lys Leu Ser
    130                 135                 140
Gln Arg Val Ile Thr His Lys Trp Thr Thr Ser Leu Ser Ala Lys Phe
145                 150                 155                 160
Lys Cys Thr Ala Gly Asn Lys Val Ser Lys Glu Ser Ser Val Glu Pro
                165                 170                 175
Val Ser Cys Pro Glu Lys Gly Leu Asp
            180                 185
```

<210> SEQ ID NO 45
<211> LENGTH: 259
<212> TYPE: PRT
<213> ORGANISM: Artificial Sequence
<220> FEATURE:
<223> OTHER INFORMATION: spacer sequence, CD34 ectodomain

<400> SEQUENCE: 45

```
Ser Leu Asp Asn Asn Gly Thr Ala Thr Pro Glu Leu Pro Thr Gln Gly
1               5                   10                  15
Thr Phe Ser Asn Val Ser Thr Asn Val Ser Tyr Gln Glu Thr Thr Thr
                20                  25                  30
Pro Ser Thr Leu Gly Ser Thr Ser Leu His Pro Val Ser Gln His Gly
            35                  40                  45
Asn Glu Ala Thr Thr Asn Ile Thr Glu Thr Thr Val Lys Phe Thr Ser
50                  55                  60
Thr Ser Val Ile Thr Ser Val Tyr Gly Asn Thr Asn Ser Ser Val Gln
65                  70                  75                  80
Ser Gln Thr Ser Val Ile Ser Thr Val Phe Thr Thr Pro Ala Asn Val
                85                  90                  95
Ser Thr Pro Glu Thr Thr Leu Lys Pro Ser Leu Ser Pro Gly Asn Val
            100                 105                 110
Ser Asp Leu Ser Thr Thr Ser Thr Ser Leu Ala Thr Ser Pro Thr Lys
        115                 120                 125
Pro Tyr Thr Ser Ser Ser Pro Ile Leu Ser Asp Ile Lys Ala Glu Ile
    130                 135                 140
Lys Cys Ser Gly Ile Arg Glu Val Lys Leu Thr Gln Gly Ile Cys Leu
145                 150                 155                 160
Glu Gln Asn Lys Thr Ser Ser Cys Ala Glu Phe Lys Lys Asp Arg Gly
                165                 170                 175
Glu Gly Leu Ala Arg Val Leu Cys Gly Glu Glu Gln Ala Asp Ala Asp
            180                 185                 190
Ala Gly Ala Gln Val Cys Ser Leu Leu Leu Ala Gln Ser Glu Val Arg
        195                 200                 205
Pro Gln Cys Leu Leu Leu Val Leu Ala Asn Arg Thr Glu Ile Ser Ser
    210                 215                 220
Lys Leu Gln Leu Met Lys Lys His Gln Ser Asp Leu Lys Lys Leu Gly
225                 230                 235                 240
Ile Leu Asp Phe Thr Glu Gln Asp Val Ala Ser His Gln Ser Tyr Ser
                245                 250                 255
Gln Lys Thr
```

<210> SEQ ID NO 46
<211> LENGTH: 21
<212> TYPE: PRT
<213> ORGANISM: Artificial Sequence
<220> FEATURE:

<223> OTHER INFORMATION: transmembrane domain

<400> SEQUENCE: 46

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 47
<211> LENGTH: 24
<212> TYPE: PRT
<213> ORGANISM: Artificial Sequence
<220> FEATURE:
<223> OTHER INFORMATION: TYRP-1 transmembrane domain

<400> SEQUENCE: 47

Ile Ile Ala Ile Ala Val Val Gly Ala Leu Leu Leu Val Ala Leu Ile
1               5                   10                  15

Phe Gly Thr Ala Ser Tyr Leu Ile
            20

<210> SEQ ID NO 48
<211> LENGTH: 140
<212> TYPE: PRT
<213> ORGANISM: Artificial Sequence
<220> FEATURE:
<223> OTHER INFORMATION: sequence comprising CD28 transmembrane domain
      and CD3zeta endodomain

<400> SEQUENCE: 48

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Arg Val Lys Phe
            20                  25                  30

Ser Arg Ser Ala Asp Ala Pro Ala Tyr Gln Gln Gly Gln Asn Gln Leu
        35                  40                  45

Tyr Asn Glu Leu Asn Leu Gly Arg Arg Glu Glu Tyr Asp Val Leu Asp
    50                  55                  60

Lys Arg Arg Gly Arg Asp Pro Glu Met Gly Gly Lys Pro Arg Arg Lys
65                  70                  75                  80

Asn Pro Gln Glu Gly Leu Tyr Asn Glu Leu Gln Lys Asp Lys Met Ala
                85                  90                  95

Glu Ala Tyr Ser Glu Ile Gly Met Lys Gly Glu Arg Arg Arg Gly Lys
            100                 105                 110

Gly His Asp Gly Leu Tyr Gln Gly Leu Ser Thr Ala Thr Lys Asp Thr
        115                 120                 125

Tyr Asp Ala Leu His Met Gln Ala Leu Pro Pro Arg
    130                 135                 140

<210> SEQ ID NO 49
<211> LENGTH: 180
<212> TYPE: PRT
<213> ORGANISM: Artificial Sequence
<220> FEATURE:
<223> OTHER INFORMATION: sequence comprising CD28 transmembrane domain
      and CD28 and CD3zeta endodomains

<400> SEQUENCE: 49

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser

```
                    20                  25                  30
Arg Leu Leu His Ser Asp Tyr Met Asn Met Thr Pro Arg Arg Pro Gly
            35                  40                  45
Pro Thr Arg Lys His Tyr Gln Pro Tyr Ala Pro Pro Arg Asp Phe Ala
        50                  55                  60
Ala Tyr Arg Ser Arg Val Lys Phe Ser Arg Ser Ala Asp Ala Pro Ala
 65                  70                  75                  80
Tyr Gln Gln Gly Gln Asn Gln Leu Tyr Asn Glu Leu Asn Leu Gly Arg
                85                  90                  95
Arg Glu Glu Tyr Asp Val Leu Asp Lys Arg Arg Gly Arg Asp Pro Glu
            100                 105                 110
Met Gly Gly Lys Pro Arg Arg Lys Asn Pro Gln Glu Gly Leu Tyr Asn
        115                 120                 125
Glu Leu Gln Lys Asp Lys Met Ala Glu Ala Tyr Ser Glu Ile Gly Met
        130                 135                 140
Lys Gly Glu Arg Arg Arg Gly Lys Gly His Asp Gly Leu Tyr Gln Gly
145                 150                 155                 160
Leu Ser Thr Ala Thr Lys Asp Thr Tyr Asp Ala Leu His Met Gln Ala
                165                 170                 175
Leu Pro Pro Arg
            180

<210> SEQ ID NO 50
<211> LENGTH: 216
<212> TYPE: PRT
<213> ORGANISM: Artificial Sequence
<220> FEATURE:
<223> OTHER INFORMATION: sequence comprising CD28 transmembrane domain
      and CD28, OX40 and CD3zeta endodomains

<400> SEQUENCE: 50

Phe Trp Val Leu Val Val Val Gly Gly Val Leu Ala Cys Tyr Ser Leu
 1               5                  10                  15
Leu Val Thr Val Ala Phe Ile Ile Phe Trp Val Arg Ser Lys Arg Ser
            20                  25                  30
Arg Leu Leu His Ser Asp Tyr Met Asn Met Thr Pro Arg Arg Pro Gly
        35                  40                  45
Pro Thr Arg Lys His Tyr Gln Pro Tyr Ala Pro Pro Arg Asp Phe Ala
    50                  55                  60
Ala Tyr Arg Ser Arg Asp Gln Arg Leu Pro Pro Asp Ala His Lys Pro
 65                  70                  75                  80
Pro Gly Gly Gly Ser Phe Arg Thr Pro Ile Gln Glu Glu Gln Ala Asp
                85                  90                  95
Ala His Ser Thr Leu Ala Lys Ile Arg Val Lys Phe Ser Arg Ser Ala
            100                 105                 110
Asp Ala Pro Ala Tyr Gln Gln Gly Gln Asn Gln Leu Tyr Asn Glu Leu
        115                 120                 125
Asn Leu Gly Arg Arg Glu Glu Tyr Asp Val Leu Asp Lys Arg Arg Gly
        130                 135                 140
Arg Asp Pro Glu Met Gly Gly Lys Pro Arg Arg Lys Asn Pro Gln Glu
145                 150                 155                 160
Gly Leu Tyr Asn Glu Leu Gln Lys Asp Lys Met Ala Glu Ala Tyr Ser
                165                 170                 175
Glu Ile Gly Met Lys Gly Glu Arg Arg Arg Gly Lys Gly His Asp Gly
            180                 185                 190
```

```
Leu Tyr Gln Gly Leu Ser Thr Ala Thr Lys Asp Thr Tyr Asp Ala Leu
            195                 200                 205

His Met Gln Ala Leu Pro Pro Arg
            210                 215
```

<210> SEQ ID NO 51
<211> LENGTH: 136
<212> TYPE: PRT
<213> ORGANISM: Artificial Sequence
<220> FEATURE:
<223> OTHER INFORMATION: sequence comprising CD8a transmembrane domain
      and CD3zeta endodomain

<400> SEQUENCE: 51

```
Ile Tyr Ile Trp Ala Pro Leu Ala Gly Thr Cys Gly Val Leu Leu Leu
1               5                   10                  15

Ser Leu Val Ile Thr Arg Val Leu Tyr Cys Lys Phe Ser Arg Ser Ala
            20                  25                  30

Asp Ala Pro Ala Tyr Gln Gln Gly Gln Asn Gln Leu Tyr Asn Glu Leu
        35                  40                  45

Asn Leu Gly Arg Arg Glu Glu Tyr Asp Val Leu Asp Lys Arg Arg Gly
    50                  55                  60

Arg Asp Pro Glu Met Gly Gly Lys Pro Arg Arg Lys Asn Pro Gln Glu
65                  70                  75                  80

Gly Leu Tyr Asn Glu Leu Gln Lys Asp Lys Met Ala Glu Ala Tyr Ser
                85                  90                  95

Glu Ile Gly Met Lys Gly Glu Arg Arg Arg Gly Lys Gly His Asp Gly
            100                 105                 110

Leu Tyr Gln Gly Leu Ser Thr Ala Thr Lys Asp Thr Tyr Asp Ala Leu
        115                 120                 125

His Met Gln Ala Leu Pro Pro Arg
    130                 135
```

<210> SEQ ID NO 52
<211> LENGTH: 178
<212> TYPE: PRT
<213> ORGANISM: Artificial Sequence
<220> FEATURE:
<223> OTHER INFORMATION: sequence comprising CD8a transmembrane domain
      and 4-1BB and CD3zeta endodomain

<400> SEQUENCE: 52

```
Ile Tyr Ile Trp Ala Pro Leu Ala Gly Thr Cys Gly Val Leu Leu Leu
1               5                   10                  15

Ser Leu Val Ile Thr Leu Tyr Cys Lys Arg Gly Arg Lys Lys Leu Leu
            20                  25                  30

Tyr Ile Phe Lys Gln Pro Phe Met Arg Pro Val Gln Thr Thr Gln Glu
        35                  40                  45

Glu Asp Gly Cys Ser Cys Arg Phe Pro Glu Glu Glu Glu Gly Gly Cys
    50                  55                  60

Glu Leu Arg Val Lys Phe Ser Arg Ser Ala Asp Ala Pro Ala Tyr Gln
65                  70                  75                  80

Gln Gly Gln Asn Gln Leu Tyr Asn Glu Leu Asn Leu Gly Arg Arg Glu
                85                  90                  95

Glu Tyr Asp Val Leu Asp Lys Arg Arg Gly Arg Asp Pro Glu Met Gly
            100                 105                 110

Gly Lys Pro Arg Arg Lys Asn Pro Gln Glu Gly Leu Tyr Asn Glu Leu
        115                 120                 125
```

```
Gln Lys Asp Lys Met Ala Glu Ala Tyr Ser Glu Ile Gly Met Lys Gly
    130                 135                 140

Glu Arg Arg Gly Lys Gly His Asp Gly Leu Tyr Gln Gly Leu Ser
145                 150                 155                 160

Thr Ala Thr Lys Asp Thr Tyr Asp Ala Leu His Met Gln Ala Leu Pro
                165                 170                 175

Pro Arg

<210> SEQ ID NO 53
<211> LENGTH: 7
<212> TYPE: PRT
<213> ORGANISM: Artificial Sequence
<220> FEATURE:
<223> OTHER INFORMATION: VH CDR sequence, CDR1

<400> SEQUENCE: 53

Gly Tyr Ala Phe Ser Ser Ser
1               5

<210> SEQ ID NO 54
<211> LENGTH: 6
<212> TYPE: PRT
<213> ORGANISM: Artificial Sequence
<220> FEATURE:
<223> OTHER INFORMATION: VH CDR sequence, CDR2

<400> SEQUENCE: 54

Tyr Pro Gly Asp Glu Asp
1               5

<210> SEQ ID NO 55
<211> LENGTH: 10
<212> TYPE: PRT
<213> ORGANISM: Artificial Sequence
<220> FEATURE:
<223> OTHER INFORMATION: VH CDR sequence, CDR3

<400> SEQUENCE: 55

Ser Leu Leu Tyr Gly Asp Tyr Leu Asp Tyr
1               5                   10

<210> SEQ ID NO 56
<211> LENGTH: 10
<212> TYPE: PRT
<213> ORGANISM: Artificial Sequence
<220> FEATURE:
<223> OTHER INFORMATION: VL CDR sequence, CDR1

<400> SEQUENCE: 56

Ser Ala Ser Ser Ser Val Ser Tyr Met His
1               5                   10

<210> SEQ ID NO 57
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 57

Asp Thr Ser Lys Leu Ala Ser
1               5

<210> SEQ ID NO 58
<211> LENGTH: 9
```

```
<212> TYPE: PRT
<213> ORGANISM: Artificial Sequence
<220> FEATURE:
<223> OTHER INFORMATION: VL CDR sequence, CDR3

<400> SEQUENCE: 58

Gln Gln Trp Asn Ile Asn Pro Leu Thr
1               5

<210> SEQ ID NO 59
<211> LENGTH: 119
<212> TYPE: PRT
<213> ORGANISM: Artificial Sequence
<220> FEATURE:
<223> OTHER INFORMATION: VH sequence from murine monoclonal antibody

<400> SEQUENCE: 59

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Glu Asp Thr Asn Tyr Ser Gly Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Ser Leu Leu Tyr Gly Asp Tyr Leu Asp Tyr Trp Gly Gln Gly
            100                 105                 110

Thr Thr Leu Thr Val Ser Ser
        115

<210> SEQ ID NO 60
<211> LENGTH: 107
<212> TYPE: PRT
<213> ORGANISM: Artificial Sequence
<220> FEATURE:
<223> OTHER INFORMATION: VL sequence from murine monoclonal antibody

<400> SEQUENCE: 60

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Phe Leu Thr Ile Asn Asn Met Glu Ala Glu
65                  70                  75                  80

Asp Ala Ala Thr Tyr Tyr Cys Gln Gln Trp Asn Ile Asn Pro Leu Thr
                85                  90                  95

Phe Gly Ala Gly Thr Lys Leu Glu Leu Lys Arg
            100                 105

<210> SEQ ID NO 61
<211> LENGTH: 241
<212> TYPE: PRT
```

<213> ORGANISM: Artificial Sequence
<220> FEATURE:
<223> OTHER INFORMATION: VH-VL scFv sequence from murine monoclonal
     antibody

<400> SEQUENCE: 61

```
Gln Val Gln Leu Gln Gln Ser Gly Pro Glu Leu Val Lys Pro Gly Ala
1               5                   10                  15
Ser Val Lys Ile Ser Cys Lys Ala Ser Gly Tyr Ala Phe Ser Ser Ser
            20                  25                  30
Trp Met Asn Trp Val Lys Gln Arg Pro Gly Lys Gly Leu Glu Trp Ile
        35                  40                  45
Gly Arg Ile Tyr Pro Gly Asp Glu Asp Thr Asn Tyr Ser Gly Lys Phe
    50                  55                  60
Lys Asp Lys Ala Thr Leu Thr Ala Asp Lys Ser Ser Thr Thr Ala Tyr
65                  70                  75                  80
Met Gln Leu Ser Ser Leu Thr Ser Glu Asp Ser Ala Val Tyr Phe Cys
                85                  90                  95
Ala Arg Ser Leu Leu Tyr Gly Asp Tyr Leu Asp Tyr Trp Gly Gln Gly
            100                 105                 110
Thr Thr Leu Thr Val Ser Ser Gly Gly Gly Gly Ser Gly Gly Gly Gly
        115                 120                 125
Ser Gly Gly Gly Gly Ser Gln Ile Val Leu Thr Gln Ser Pro Ala Ile
    130                 135                 140
Met Ser Ala Ser Pro Gly Glu Lys Val Thr Met Thr Cys Ser Ala Ser
145                 150                 155                 160
Ser Ser Val Ser Tyr Met His Trp Tyr Gln Gln Lys Ser Gly Thr Ser
                165                 170                 175
Pro Lys Arg Trp Ile Tyr Asp Thr Ser Lys Leu Ala Ser Gly Val Pro
            180                 185                 190
Asp Arg Phe Ser Gly Ser Gly Ser Gly Thr Ser Tyr Phe Leu Thr Ile
        195                 200                 205
Asn Asn Met Glu Ala Glu Asp Ala Ala Thr Tyr Tyr Cys Gln Gln Trp
    210                 215                 220
Asn Ile Asn Pro Leu Thr Phe Gly Ala Gly Thr Lys Leu Glu Leu Lys
225                 230                 235                 240
Arg
```

<210> SEQ ID NO 62
<211> LENGTH: 5
<212> TYPE: PRT
<213> ORGANISM: Artificial Sequence
<220> FEATURE:
<223> OTHER INFORMATION: VH CDR sequence, CDR1

<400> SEQUENCE: 62

```
Ser Tyr Trp Met Asn
1               5
```

<210> SEQ ID NO 63
<211> LENGTH: 16
<212> TYPE: PRT
<213> ORGANISM: Artificial Sequence
<220> FEATURE:
<223> OTHER INFORMATION: VH CDR sequence, CDR2

<400> SEQUENCE: 63

```
Gln Ile Trp Pro Gly Asp Gly Asp Thr Asn Tyr Asn Gly Lys Phe Lys
1               5                   10                  15
```

```
<210> SEQ ID NO 64
<211> LENGTH: 15
<212> TYPE: PRT
<213> ORGANISM: Artificial Sequence
<220> FEATURE:
<223> OTHER INFORMATION: VH CDR sequence, CDR3

<400> SEQUENCE: 64

Arg Glu Thr Thr Thr Val Gly Arg Tyr Tyr Tyr Ala Met Asp Tyr
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: VL CDR sequence, CDR1

<400> SEQUENCE: 65

Lys Ala Ser Gln Ser Val Asp Tyr Asp Gly Asp Ser Tyr Leu Asn
1               5                   10                  15

<210> SEQ ID NO 66
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 66

Asp Ala Ser Asn Leu Val Ser
1               5

<210> SEQ ID NO 67
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 67

Gln Gln Ser Thr Glu Asp Pro Trp Thr
1               5

<210> SEQ ID NO 68
<211> LENGTH: 235
<212> TYPE: PRT
<213> ORGANISM: Artificial Sequence
<220> FEATURE:
<223> OTHER INFORMATION: murine CD19ALAb scFv sequence

<400> SEQUENCE: 68

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
```

```
                    85                  90                  95
Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser Asp Ile Gln Leu
                115                 120                 125

Thr Gln Ser Pro Ala Ser Leu Ala Val Ser Leu Gly Gln Arg Ala Thr
            130                 135                 140

Ile Ser Cys Lys Ala Ser Gln Ser Val Asp Tyr Asp Gly Asp Ser Tyr
145                 150                 155                 160

Leu Asn Trp Tyr Gln Gln Ile Pro Gly Gln Pro Pro Lys Leu Leu Ile
                165                 170                 175

Tyr Asp Ala Ser Asn Leu Val Ser Gly Ile Pro Pro Arg Phe Ser Gly
                180                 185                 190

Ser Gly Ser Gly Thr Asp Phe Thr Leu Asn Ile His Pro Val Glu Lys
            195                 200                 205

Val Asp Ala Ala Thr Tyr His Cys Gln Gln Ser Thr Glu Asp Pro Trp
210                 215                 220

Thr Phe Gly Gly Gly Thr Lys Leu Glu Ile Lys
225                 230                 235

<210> SEQ ID NO 69
<211> LENGTH: 236
<212> TYPE: PRT
<213> ORGANISM: Artificial Sequence
<220> FEATURE:
<223> OTHER INFORMATION: Humanised CD19ALAb scFv sequence - Heavy 19,
      Kappa 16

<400> SEQUENCE: 69

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ala Phe Ser Ser Tyr
            20                  25                  30

Trp Met Asn Trp Val Arg Gln Ala Pro Gly Gln Ser Leu Glu Trp Ile
        35                  40                  45

Gly Gln Ile Trp Pro Gly Asp Gly Asp Thr Asn Tyr Asn Gly Lys Phe
    50                  55                  60

Lys Gly Arg Ala Thr Leu Thr Ala Asp Glu Ser Ala Arg Thr Ala Tyr
65                  70                  75                  80

Met Glu Leu Ser Ser Leu Arg Ser Gly Asp Thr Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Lys Gly Thr Leu Val Thr Val Ser Ser Asp Ile Gln Leu
                115                 120                 125

Thr Gln Ser Pro Asp Ser Leu Ala Val Ser Leu Gly Glu Arg Ala Thr
            130                 135                 140

Ile Asn Cys Lys Ala Ser Gln Ser Val Asp Tyr Asp Gly Asp Ser Tyr
145                 150                 155                 160

Leu Asn Trp Tyr Gln Gln Lys Pro Gly Gln Pro Pro Lys Leu Leu Ile
                165                 170                 175

Tyr Asp Ala Ser Asn Leu Val Ser Gly Val Pro Asp Arg Phe Ser Gly
                180                 185                 190

Ser Gly Ser Gly Thr Asp Phe Thr Leu Thr Ile Ser Ser Leu Gln Ala
            195                 200                 205
```

Ala Asp Val Ala Val Tyr His Cys Gln Gln Ser Thr Glu Asp Pro Trp
    210                 215                 220

Thr Phe Gly Gln Gly Thr Lys Val Glu Ile Lys Arg
225                 230                 235

<210> SEQ ID NO 70
<211> LENGTH: 236
<212> TYPE: PRT
<213> ORGANISM: Artificial Sequence
<220> FEATURE:
<223> OTHER INFORMATION: Humanised CD19ALAb scFv sequence - Heavy 19,
      Kappa 7

<400> SEQUENCE: 70

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ala Phe Ser Ser Tyr
                20                  25                  30

Trp Met Asn Trp Val Arg Gln Ala Pro Gly Gln Ser Leu Glu Trp Ile
            35                  40                  45

Gly Gln Ile Trp Pro Gly Asp Gly Asp Thr Asn Tyr Asn Gly Lys Phe
        50                  55                  60

Lys Gly Arg Ala Thr Leu Thr Ala Asp Glu Ser Ala Arg Thr Ala Tyr
65                  70                  75                  80

Met Glu Leu Ser Ser Leu Arg Ser Gly Asp Thr Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Lys Gly Thr Leu Val Thr Val Ser Ser Asp Ile Gln Leu
            115                 120                 125

Thr Gln Ser Pro Asp Ser Leu Ala Val Ser Leu Gly Glu Arg Ala Thr
        130                 135                 140

Ile Asn Cys Lys Ala Ser Gln Ser Val Asp Tyr Asp Gly Asp Ser Tyr
145                 150                 155                 160

Leu Asn Trp Tyr Gln Gln Lys Pro Gly Gln Pro Pro Lys Val Leu Ile
                165                 170                 175

Tyr Asp Ala Ser Asn Leu Val Ser Gly Val Pro Asp Arg Phe Ser Gly
                180                 185                 190

Ser Gly Ser Gly Thr Asp Phe Thr Leu Thr Ile Ser Ser Leu Gln Ala
            195                 200                 205

Ala Asp Val Ala Val Tyr Tyr Cys Gln Gln Ser Thr Glu Asp Pro Trp
        210                 215                 220

Thr Phe Gly Gln Gly Thr Lys Val Glu Ile Lys Arg
225                 230                 235

<210> SEQ ID NO 71
<211> LENGTH: 124
<212> TYPE: PRT
<213> ORGANISM: Artificial Sequence
<220> FEATURE:
<223> OTHER INFORMATION: murine CD19ALAb VH sequence

<400> SEQUENCE: 71

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile

```
                35                  40                  45
Gly Gln Ile Trp Pro Gly Asp Gly Asp Thr Asn Tyr Asn Gly Lys Phe
        50                  55                  60
Lys Gly Lys Ala Thr Leu Thr Ala Asp Glu Ser Ser Ser Thr Ala Tyr
 65                 70                  75                  80
Met Gln Leu Ser Ser Leu Ala Ser Glu Asp Ser Ala Val Tyr Phe Cys
                85                  90                  95
Ala Arg Arg Glu Thr Thr Thr Val Gly Arg Tyr Tyr Tyr Ala Met Asp
            100                 105                 110
Tyr Trp Gly Gln Gly Thr Thr Val Thr Val Ser Ser
            115                 120

<210> SEQ ID NO 72
<211> LENGTH: 124
<212> TYPE: PRT
<213> ORGANISM: Artificial Sequence
<220> FEATURE:
<223> OTHER INFORMATION: humanised CD19ALAb VH sequence

<400> SEQUENCE: 72

Gln Val Gln Leu Val Gln Ser Gly Ala Glu Val Lys Lys Pro Gly Ala
 1               5                  10                  15
Ser Val Lys Leu Ser Cys Lys Ala Ser Gly Tyr Ala Phe Ser Ser Tyr
            20                  25                  30
Trp Met Asn Trp Val Arg Gln Ala Pro Gly Gln Ser Leu Glu Trp Ile
            35                  40                  45
Gly Gln Ile Trp Pro Gly Asp Gly Asp Thr Asn Tyr Asn Gly Lys Phe
        50                  55                  60
Lys Gly Arg Ala Thr Leu Thr Ala Asp Glu Ser Ala Arg Thr Ala Tyr
 65                 70                  75                  80
Met Glu Leu Ser Ser Leu Arg Ser Gly Asp Thr Ala Val Tyr Phe Cys
                85                  90                  95
Ala Arg Arg Glu Thr Thr Thr Val Gly Arg Tyr Tyr Tyr Ala Met Asp
            100                 105                 110
Tyr Trp Gly Lys Gly Thr Leu Val Thr Val Ser Ser
            115                 120

<210> SEQ ID NO 73
<211> LENGTH: 111
<212> TYPE: PRT
<213> ORGANISM: Artificial Sequence
<220> FEATURE:
<223> OTHER INFORMATION: murine CD19ALAb VL sequence

<400> SEQUENCE: 73

Asp Ile Gln Leu Thr Gln Ser Pro Ala Ser Leu Ala Val Ser Leu Gly
 1               5                  10                  15
Gln Arg Ala Thr Ile Ser Cys Lys Ala Ser Gln Ser Val Asp Tyr Asp
            20                  25                  30
Gly Asp Ser Tyr Leu Asn Trp Tyr Gln Gln Ile Pro Gly Gln Pro Pro
            35                  40                  45
Lys Leu Leu Ile Tyr Asp Ala Ser Asn Leu Val Ser Gly Ile Pro Pro
        50                  55                  60
Arg Phe Ser Gly Ser Gly Ser Gly Thr Asp Phe Thr Leu Asn Ile His
 65                 70                  75                  80
Pro Val Glu Lys Val Asp Ala Ala Thr Tyr His Cys Gln Gln Ser Thr
                85                  90                  95
```

```
Glu Asp Pro Trp Thr Phe Gly Gly Gly Thr Lys Leu Glu Ile Lys
                100                 105                 110
```

<210> SEQ ID NO 74
<211> LENGTH: 112
<212> TYPE: PRT
<213> ORGANISM: Artificial Sequence
<220> FEATURE:
<223> OTHER INFORMATION: humanised CD19ALAb VL sequence, Kappa 16

<400> SEQUENCE: 74

```
Asp Ile Gln Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
                20                  25                  30

Gly Asp Ser Tyr Leu Asn Trp Tyr Gln Gln Lys Pro Gly Gln Pro Pro
            35                  40                  45

Lys Leu Leu Ile Tyr Asp Ala Ser Asn Leu Val Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Ala Asp Val Ala Val Tyr His Cys Gln Gln Ser Thr
                85                  90                  95

Glu Asp Pro Trp Thr Phe Gly Gln Gly Thr Lys Val Glu Ile Lys Arg
                100                 105                 110
```

<210> SEQ ID NO 75
<211> LENGTH: 112
<212> TYPE: PRT
<213> ORGANISM: Artificial Sequence
<220> FEATURE:
<223> OTHER INFORMATION: humanised CD19ALAb VL sequence, Kappa 7

<400> SEQUENCE: 75

```
Asp Ile Gln Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
                20                  25                  30

Gly Asp Ser Tyr Leu Asn Trp Tyr Gln Gln Lys Pro Gly Gln Pro Pro
            35                  40                  45

Lys Val Leu Ile Tyr Asp Ala Ser Asn Leu Val Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Ala Asp Val Ala Val Tyr Tyr Cys Gln Gln Ser Thr
                85                  90                  95

Glu Asp Pro Trp Thr Phe Gly Gln Gly Thr Lys Val Glu Ile Lys Arg
                100                 105                 110
```

<210> SEQ ID NO 76
<211> LENGTH: 119
<212> TYPE: PRT
<213> ORGANISM: Artificial Sequence
<220> FEATURE:
<223> OTHER INFORMATION: VH sequence from 1D9-3 antibody

<400> SEQUENCE: 76

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
```

```
            20                  25                  30
Ala Met His Trp Val Arg Gln Ala Pro Gly Lys Gly Leu Glu Trp Val
        35                  40                  45

Ala Arg Ile Arg Ser Lys Ser Ser Asn Tyr Ala Thr Tyr Tyr Ala Asp
        50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Val Asp Tyr Leu Tyr Ala Met Asp Tyr Trp Gly Gln Gly
                100                 105                 110

Thr Ser Val Thr Val Ser Ser
            115

<210> SEQ ID NO 77
<211> LENGTH: 107
<212> TYPE: PRT
<213> ORGANISM: Artificial Sequence
<220> FEATURE:
<223> OTHER INFORMATION: VL sequence from 1D9-3 antibody

<400> SEQUENCE: 77

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Phe
                85                  90                  95

Thr Phe Gly Ser Gly Thr Lys Leu Glu Ile Lys
                100                 105

<210> SEQ ID NO 78
<211> LENGTH: 120
<212> TYPE: PRT
<213> ORGANISM: Artificial Sequence
<220> FEATURE:
<223> OTHER INFORMATION: VH sequence from 3B4-13 antibody

<400> SEQUENCE: 78

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Ala Thr Ala Tyr Asn Gln Lys Phe
        50                  55                  60

Lys Gly Lys Ala Ile Leu Thr Ala Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95
```

Thr Arg Tyr Asp Tyr Gly Ser Ser Pro Trp Phe Ala Tyr Trp Gly Gln
            100                 105                 110

Gly Thr Leu Val Thr Val Ser Ala
        115                 120

<210> SEQ ID NO 79
<211> LENGTH: 109
<212> TYPE: PRT
<213> ORGANISM: Artificial Sequence
<220> FEATURE:
<223> OTHER INFORMATION: VL sequence from 3B4-13 antibody

<400> SEQUENCE: 79

Gln Ala Val Val Thr Gln Glu Ser Ala Leu Thr Thr Ser Pro Gly Glu
1               5                   10                  15

Thr Val Thr Leu Thr Cys Arg Ser Ser Ala Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Asn Ser Asn
                85                  90                  95

His Trp Val Phe Gly Gly Gly Thr Lys Leu Thr Val Leu
            100                 105

<210> SEQ ID NO 80
<211> LENGTH: 119
<212> TYPE: PRT
<213> ORGANISM: Artificial Sequence
<220> FEATURE:
<223> OTHER INFORMATION: VH sequence from 7G6-6 antibody

<400> SEQUENCE: 80

Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Tyr Gly Ser Ser Phe Asp Tyr Trp Gly Gln Gly
            100                 105                 110

Thr Thr Leu Thr Val Ser Ser
        115

<210> SEQ ID NO 81
<211> LENGTH: 111
<212> TYPE: PRT
<213> ORGANISM: Artificial Sequence
<220> FEATURE:
<223> OTHER INFORMATION: VL sequence from 7G6-6 antibody

```
<400> SEQUENCE: 81

Asp Ile Val Met Ser Gln Ser Pro Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Thr Phe Gly Gly Gly Thr Lys Leu Glu Ile Lys
            100                 105                 110

<210> SEQ ID NO 82
<211> LENGTH: 120
<212> TYPE: PRT
<213> ORGANISM: Artificial Sequence
<220> FEATURE:
<223> OTHER INFORMATION: VH sequence from 6C4-6 antibody

<400> SEQUENCE: 82

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg His Ala Asp Asp Tyr Gly Phe Ala Trp Phe Ala Tyr Trp Gly Gln
            100                 105                 110

Gly Thr Leu Val Thr Val Ser Ala
        115                 120

<210> SEQ ID NO 83
<211> LENGTH: 107
<212> TYPE: PRT
<213> ORGANISM: Artificial Sequence
<220> FEATURE:
<223> OTHER INFORMATION: VL sequence from 6C4-6 antibody

<400> SEQUENCE: 83

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60
```

```
Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Pro
                 85                  90                  95

Thr Phe Gly Gly Gly Thr Lys Leu Glu Ile Lys
                100                 105

<210> SEQ ID NO 84
<211> LENGTH: 121
<212> TYPE: PRT
<213> ORGANISM: Artificial Sequence
<220> FEATURE:
<223> OTHER INFORMATION: VH sequence from 4D9-12 antibody

<400> SEQUENCE: 84

Glu Phe Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Asp Tyr
                 20                  25                  30

Asn Met Asn Trp Val Lys Gln Ser Asn Gly Lys Ser Leu Glu Trp Ile
             35                  40                  45

Gly Val Ile Asn Pro Asn Tyr Gly Thr Thr Ser Tyr Asn Gln Lys Phe
 50                  55                  60

Lys Gly Lys Ala Thr Leu Thr Val Asp Gln Ser Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Ser Ser Thr Thr Val Val Asp Trp Tyr Phe Asp Val Trp Gly
                100                 105                 110

Thr Gly Thr Thr Val Thr Val Ser Ser
            115                 120

<210> SEQ ID NO 85
<211> LENGTH: 107
<212> TYPE: PRT
<213> ORGANISM: Artificial Sequence
<220> FEATURE:
<223> OTHER INFORMATION: VL sequence from 4D9-12 antibody

<400> SEQUENCE: 85

Asp Ile Gln Met Thr Gln Ser Pro Ser Ser Leu Ser Ala Ser Leu Gly
 1               5                  10                  15

Glu Arg Val Ser Leu Thr Cys Arg Ala Ser Gln Glu Ile Ser Gly Tyr
                 20                  25                  30

Leu Ser Trp Leu Gln Gln Lys Pro Asp Gly Thr Ile Lys Arg Leu Ile
             35                  40                  45

Tyr Ala Ala Ser Thr Leu Asp Ser Gly Val Pro Lys Arg Phe Ser Gly
     50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ser Tyr Pro Phe
                 85                  90                  95

Thr Phe Gly Ser Gly Thr Lys Leu Glu Ile Lys
                100                 105

<210> SEQ ID NO 86
<211> LENGTH: 118
<212> TYPE: PRT
<213> ORGANISM: Artificial Sequence
```

```
<220> FEATURE:
<223> OTHER INFORMATION: VH sequence from 5H4-9 antibody

<400> SEQUENCE: 86

Gln Val Gln Val Gln Gln Pro Gly Ala Glu Leu Val Arg Pro Gly Thr
1               5                   10                  15

Ser Val Lys Leu Ser Cys Lys Ala Ser Gly Tyr Thr Phe Thr Arg Tyr
            20                  25                  30

Trp Met Tyr Trp Val Lys Gln Arg Pro Gly Gln Gly Leu Glu Trp Ile
        35                  40                  45

Gly Val Ile Asp Pro Ser Asp Asn Phe Thr Tyr Tyr Asn Gln Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Gly Ser Ser Tyr Val Gly Tyr Trp Gly Gln Gly Thr
            100                 105                 110

Thr Leu Thr Val Ser Ser
        115

<210> SEQ ID NO 87
<211> LENGTH: 113
<212> TYPE: PRT
<213> ORGANISM: Artificial Sequence
<220> FEATURE:
<223> OTHER INFORMATION: VL sequence from 5H4-9 antibody

<400> SEQUENCE: 87

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys

<210> SEQ ID NO 88
<211> LENGTH: 124
<212> TYPE: PRT
<213> ORGANISM: Artificial Sequence
<220> FEATURE:
<223> OTHER INFORMATION: VH sequence from 10C1-D9 antibody

<400> SEQUENCE: 88

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Asp Met Gly Val Ser Trp Ile Arg Gln Pro Ser Gly Lys Gly Leu Glu
```

```
                35                  40                  45
Trp Leu Ala His Ile Tyr Trp Asp Asp Lys Arg Tyr Asn Pro Ser
            50                  55                  60
Leu Lys Ser Arg Leu Thr Ile Ser Lys Asp Ala Ser Arg Asn Gln Val
 65                  70                  75                  80
Phe Leu Lys Ile Ala Thr Val Asp Thr Ala Asp Thr Ala Thr Tyr Tyr
                 85                  90                  95
Cys Ala Arg Ser Pro Trp Ile Tyr Tyr Gly His Tyr Trp Cys Phe Asp
                100                 105                 110
Val Trp Gly Thr Gly Thr Thr Val Thr Val Ser Ser
            115                 120

<210> SEQ ID NO 89
<211> LENGTH: 107
<212> TYPE: PRT
<213> ORGANISM: Artificial Sequence
<220> FEATURE:
<223> OTHER INFORMATION: VL sequence from 10C1-D9 antibody

<400> SEQUENCE: 89

Asp Ile Gln Met Thr Gln Thr Thr Ser Ser Leu Ser Ala Ser Leu Gly
  1               5                  10                  15
Asp Arg Val Thr Ile Ser Cys Arg Ala Ser Gln Asp Ile Ser Asn Tyr
             20                  25                  30
Leu Asn Trp Tyr Gln Gln Lys Pro Asp Gly Thr Val Lys Leu Leu Ile
             35                  40                  45
Tyr Tyr Thr Ser Arg Leu His Ser Gly Val Pro Ser Arg Phe Ser Gly
 50                  55                  60
Ser Gly Ser Gly Thr Asp Tyr Ser Leu Thr Ile Ser Asn Leu Glu Gln
 65                  70                  75                  80
Glu Asp Ile Ala Thr Tyr Phe Cys Gln Gln Gly Asn Thr Leu Pro Phe
                 85                  90                  95
Thr Phe Gly Ser Gly Thr Lys Leu Glu Ile Lys
            100                 105

<210> SEQ ID NO 90
<211> LENGTH: 123
<212> TYPE: PRT
<213> ORGANISM: Artificial Sequence
<220> FEATURE:
<223> OTHER INFORMATION: VH sequence from 15G7-2 antibody

<400> SEQUENCE: 90

Gln Val Gln Leu Gln Gln Ser Gly Ala Glu Leu Val Lys Pro Gly Ala
  1               5                  10                  15
Ser Val Lys Leu Ser Cys Lys Ala Ser Gly Tyr Thr Phe Thr Glu Tyr
             20                  25                  30
Thr Ile His Trp Val Lys Gln Arg Ser Gly Gln Gly Leu Glu Trp Ile
             35                  40                  45
Gly Trp Phe Tyr Pro Gly Ser Gly Ser Ile Lys Tyr Asn Glu Lys Phe
 50                  55                  60
Lys Asp Lys Ala Thr Leu Thr Ala Asp Lys Ser Ser Thr Val Tyr
 65                  70                  75                  80
Met Glu Leu Ser Arg Leu Thr Ser Glu Asp Ser Ala Val Tyr Phe Cys
                 85                  90                  95
Ala Arg His Gly Asp Gly Tyr Tyr Leu Pro Pro Tyr Tyr Phe Asp Tyr
                100                 105                 110
```

```
Trp Gly Gln Gly Thr Thr Leu Thr Val Ser Ser
        115                 120

<210> SEQ ID NO 91
<211> LENGTH: 106
<212> TYPE: PRT
<213> ORGANISM: Artificial Sequence
<220> FEATURE:
<223> OTHER INFORMATION: VL sequence from 15G7-2 antibody

<400> SEQUENCE: 91

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys
            100                 105

<210> SEQ ID NO 92
<211> LENGTH: 121
<212> TYPE: PRT
<213> ORGANISM: Artificial Sequence
<220> FEATURE:
<223> OTHER INFORMATION: VH sequence from 2B12-8 antibody

<400> SEQUENCE: 92

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ile Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Ile Tyr Tyr Gly Ser Arg Glu Gly Phe Asp Tyr Trp Gly
            100                 105                 110

Gln Gly Thr Thr Leu Thr Val Ser Ser
        115                 120

<210> SEQ ID NO 93
<211> LENGTH: 107
<212> TYPE: PRT
<213> ORGANISM: Artificial Sequence
<220> FEATURE:
<223> OTHER INFORMATION: VL sequence from 2B12-8 antibody

<400> SEQUENCE: 93

Asp Ile Val Leu Thr Gln Ser Pro Ala Thr Leu Ser Val Thr Pro Gly
```

```
                1               5                  10                 15
Asp Ser Val Ser Leu Ser Cys Arg Ala Ser Gln Ser Ile Ser Thr Asn
                    20                 25                 30

Leu His Trp Tyr Gln Gln Lys Ser His Ala Ser Pro Arg Leu Leu Ile
            35                 40                 45

Lys Tyr Ala Ser Gln Ser Val Ser Gly Ile Pro Ser Arg Phe Ser Gly
        50                 55                 60

Ser Gly Ser Gly Thr Asp Phe Thr Leu Ser Ile Asn Ser Val Glu Thr
65                  70                 75                 80

Glu Asp Phe Gly Ile Phe Phe Cys Gln Gln Ser Tyr Ser Trp Pro Tyr
                85                 90                 95

Thr Phe Gly Gly Gly Thr Lys Leu Glu Ile Lys
                100                105
```

<210> SEQ ID NO 94
<211> LENGTH: 120
<212> TYPE: PRT
<213> ORGANISM: Artificial Sequence
<220> FEATURE:
<223> OTHER INFORMATION: VH sequence from 2C4-4 antibody

<400> SEQUENCE: 94

```
Gln Val Gln Leu Gln Gln Pro Gly Ala Glu Leu Val Met Pro Gly Ala
1               5                  10                 15

Ser Val Lys Leu Ser Cys Lys Ala Ser Gly Tyr Thr Phe Thr Ser Tyr
                20                 25                 30

Trp Met His Trp Val Lys Gln Arg Pro Gly Gln Gly Leu Glu Trp Ile
            35                 40                 45

Gly Glu Ile Asp Pro Ser Asp Ser Tyr Thr Asn Tyr Asn Gln Lys Phe
        50                 55                 60

Lys Gly Lys Ser Thr Leu Thr Val Asp Lys Ser Ser Ser Thr Ala Tyr
65                  70                 75                 80

Ile Gln Leu Ser Ser Leu Thr Ser Glu Asp Ser Ala Val Tyr Tyr Cys
                85                 90                 95

Ala Arg Trp Ala Ser Tyr Arg Gly Tyr Ala Met Asp Tyr Trp Gly Gln
                100                105                110

Gly Thr Ser Val Thr Val Ser Ser
            115                120
```

<210> SEQ ID NO 95
<211> LENGTH: 112
<212> TYPE: PRT
<213> ORGANISM: Artificial Sequence
<220> FEATURE:
<223> OTHER INFORMATION: VL sequence from 2C4-4 antibody

<400> SEQUENCE: 95

```
Asp Val Leu Met Thr Gln Thr Pro Leu Ser Leu Pro Val Ser Leu Gly
1               5                  10                 15

Asp Gln Ala Ser Ile Ser Cys Arg Ser Ser Gln Ser Ile Val His Ser
                20                 25                 30

Asn Gly Asn Thr Tyr Leu Glu Trp Tyr Leu Gln Lys Pro Gly Gln Ser
            35                 40                 45

Pro Lys Leu Leu Ile Tyr Lys Val Ser Asn Arg Phe Ser Gly Val Pro
        50                 55                 60

Asp Arg Phe Ser Gly Ser Glu Ser Gly Thr Asp Phe Thr Leu Lys Ile
65                  70                 75                 80
```

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 96
<211> LENGTH: 119
<212> TYPE: PRT
<213> ORGANISM: Artificial Sequence
<220> FEATURE:
<223> OTHER INFORMATION: VH sequence from 3E10-7 antibody

<400> SEQUENCE: 96

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Lys Gln Ser Asn Gly Lys Ser Leu Glu Trp Ile
        35                  40                  45

Gly Val Ile Asn Pro Asn Tyr Gly Thr Thr Ser Tyr Asn Gln Arg Phe
    50                  55                  60

Lys Gly Lys Ala Thr Leu Thr Val Asp Gln Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Gly Leu Arg Tyr Trp Tyr Phe Asp Val Trp Gly Thr Gly
            100                 105                 110

Thr Thr Val Thr Val Ser Ser
            115

<210> SEQ ID NO 97
<211> LENGTH: 107
<212> TYPE: PRT
<213> ORGANISM: Artificial Sequence
<220> FEATURE:
<223> OTHER INFORMATION: VL sequence from 3E10-7 antibody

<400> SEQUENCE: 97

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Phe
                85                  90                  95

Thr Phe Gly Ser Gly Thr Lys Leu Glu Ile Lys
            100                 105

<210> SEQ ID NO 98
<211> LENGTH: 120
<212> TYPE: PRT
<213> ORGANISM: Artificial Sequence
<220> FEATURE:
<223> OTHER INFORMATION: VH sequence from LT22 antibody

<400> SEQUENCE: 98

Glu Val Gln Leu Val Glu Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Met
        35                  40                  45

Gly Asn Ile Tyr Pro Ser Asp Ser Phe Thr Asn Tyr Asn Gln Lys Phe
    50                  55                  60

Lys Asp Arg Val Thr Ile Thr Ala Asp Lys Ser Thr Ser Thr Val Tyr
65                  70                  75                  80

Leu Glu Leu Arg Asn Leu Arg Ser Asp Thr Ala Val Tyr Tyr Cys
                85                  90                  95

Thr Arg Asp Thr Gln Glu Arg Ser Trp Tyr Phe Asp Val Trp Gly Gln
            100                 105                 110

Gly Thr Leu Val Thr Val Ser Ser
        115                 120

<210> SEQ ID NO 99
<211> LENGTH: 113
<212> TYPE: PRT
<213> ORGANISM: Artificial Sequence
<220> FEATURE:
<223> OTHER INFORMATION: VL sequence from LT22 antibody

<400> SEQUENCE: 99

Asp Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Ala Arg Phe Ser Gly Ser Gly Ser Gly Ala Glu Phe Thr Leu Thr Ile
65                  70                  75                  80

Ser Ser Leu Gln Ser Glu Asp Phe Ala Val Tyr Tyr Cys Ser Gln Ser
                85                  90                  95

Thr His Val Pro Trp Thr Phe Gly Gln Gly Thr Arg Leu Glu Ile Lys
            100                 105                 110

Arg

<210> SEQ ID NO 100
<211> LENGTH: 121
<212> TYPE: PRT
<213> ORGANISM: Artificial Sequence
<220> FEATURE:
<223> OTHER INFORMATION: VH sequence from Inotuzumab G5_44 antibody

<400> SEQUENCE: 100

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Asn Tyr Ala Thr Tyr Arg Arg Lys Phe

```
                50                  55                  60
Gln Gly Arg Val Thr Met Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Glu Gly Tyr Gly Asn Tyr Gly Ala Trp Phe Ala Tyr Trp Gly
                100                 105                 110

Gln Gly Thr Leu Val Thr Val Ser Ser
        115                 120

<210> SEQ ID NO 101
<211> LENGTH: 113
<212> TYPE: PRT
<213> ORGANISM: Artificial Sequence
<220> FEATURE:
<223> OTHER INFORMATION: VL sequence from Inotuzumab G5_44 antibody

<400> SEQUENCE: 101

Asp Val Gln Val Thr Gln Ser Pro Ser Ser Leu Ser Ala Ser Val Gly
 1               5                  10                  15

Asp Arg Val Thr Ile Thr Cys Arg Ser Ser Gln Ser Leu Ala Asn Ser
                20                  25                  30

Tyr Gly Asn Thr Phe Leu Ser Trp Tyr Leu His Lys Pro Gly Lys Ala
             35                  40                  45

Pro Gln Leu Leu Ile Tyr Gly Ile Ser Asn Arg Phe Ser Gly Val Pro
         50                  55                  60

Asp Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Leu Gln Gly
                 85                  90                  95

Thr His Gln Pro Tyr Thr Phe Gly Gln Gly Thr Lys Val Glu Ile Lys
                100                 105                 110

Arg

<210> SEQ ID NO 102
<211> LENGTH: 127
<212> TYPE: PRT
<213> ORGANISM: Artificial Sequence
<220> FEATURE:
<223> OTHER INFORMATION: VH sequence from 9A8-1 antibody

<400> SEQUENCE: 102

Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Phe Ser Asn Phe
                20                  25                  30

Ala Met Ala Trp Val Arg Gln Pro Pro Thr Lys Gly Leu Glu Trp Val
             35                  40                  45

Ala Ser Ile Ser Thr Gly Gly Asn Thr Tyr Tyr Arg Asp Ser Val
         50                  55                  60

Lys Gly Arg Phe Thr Ile Ser Arg Asp Asp Ala Lys Asn Thr Gln Tyr
 65                  70                  75                  80

Leu Gln Met Asp Ser Leu Arg Ser Glu Asp Thr Ala Thr Tyr Tyr Cys
                 85                  90                  95

Ala Arg Gln Arg Asn Tyr Tyr Asp Gly Ser Tyr Asp Tyr Glu Gly Tyr
                100                 105                 110

Thr Met Asp Ala Trp Gly Gln Gly Thr Ser Val Thr Val Ser Ser
```

115            120            125

<210> SEQ ID NO 103
<211> LENGTH: 107
<212> TYPE: PRT
<213> ORGANISM: Artificial Sequence
<220> FEATURE:
<223> OTHER INFORMATION: VL sequence from 9A8-1 antibody

<400> SEQUENCE: 103

Asp Ile Gln Met Thr Gln Ser Pro Ser Ser Leu Ser Ala Ser Leu Gly
1               5                   10                  15

Asp Arg Val Thr Ile Thr Cys Arg Ser Ser Gln Asp Ile Gly Asn Tyr
            20                  25                  30

Leu Thr Trp Phe Gln Gln Lys Val Gly Arg Ser Pro Arg Arg Met Ile
        35                  40                  45

Tyr Gly Ala Ile Lys Leu Glu Asp Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Val Ala Asp Tyr Gln Cys Leu Gln Ser Ile Gln Tyr Pro Phe
                85                  90                  95

Thr Phe Gly Ser Gly Thr Lys Leu Glu Ile Lys
            100                 105

<210> SEQ ID NO 104
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 104

Arg Ala Glu Gly Arg Gly Ser Leu Leu Thr Cys Gly Asp Val Glu Glu
1               5                   10                  15

Asn Pro Gly Pro
            20

<210> SEQ ID NO 105
<211> LENGTH: 226
<212> TYPE: PRT
<213> ORGANISM: Homo sapiens

<400> SEQUENCE: 105

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro

```
            115                 120                 125
Pro Pro Arg Pro Phe Leu Asp Met Gly Glu Gly Thr Lys Asn Arg Ile
    130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
                180                 185                 190

Leu Asp Asp Cys Ser Met Tyr Glu Asp Ile Ser Arg Gly Leu Gln Gly
            195                 200                 205

Thr Tyr Gln Asp Val Gly Ser Leu Asn Ile Gly Asp Val Gln Leu Glu
    210                 215                 220

Lys Pro
225

<210> SEQ ID NO 106
<211> LENGTH: 229
<212> TYPE: PRT
<213> ORGANISM: Homo sapiens

<400> SEQUENCE: 106

Met Ala Arg Leu Ala Leu Ser Pro Val Pro Ser His Trp Met Val Ala
1               5                   10                  15

Leu Leu Leu Leu Leu Ser Ala Glu Pro Val Pro Ala Ala Arg Ser Glu
                20                  25                  30

Asp Arg Tyr Arg Asn Pro Lys Gly Ser Ala Cys Ser Arg Ile Trp Gln
            35                  40                  45

Ser Pro Arg Phe Ile Ala Arg Lys Arg Gly Phe Thr Val Lys Met His
50                  55                  60

Cys Tyr Met Asn Ser Ala Ser Gly Asn Val Ser Trp Leu Trp Lys Gln
65                  70                  75                  80

Glu Met Asp Glu Asn Pro Gln Gln Leu Lys Leu Glu Lys Gly Arg Met
                85                  90                  95

Glu Glu Ser Gln Asn Glu Ser Leu Ala Thr Leu Thr Ile Gln Gly Ile
            100                 105                 110

Arg Phe Glu Asp Asn Gly Ile Tyr Phe Cys Gln Gln Lys Cys Asn Asn
            115                 120                 125

Thr Ser Glu Val Tyr Gln Gly Cys Gly Thr Glu Leu Arg Val Met Gly
    130                 135                 140

Phe Ser Thr Leu Ala Gln Leu Lys Gln Arg Asn Thr Leu Lys Asp Gly
145                 150                 155                 160

Ile Ile Met Ile Gln Thr Leu Leu Ile Leu Phe Ile Ile Val Pro
                165                 170                 175

Ile Phe Leu Leu Leu Asp Lys Asp Asp Ser Lys Ala Gly Met Glu Glu
                180                 185                 190

Asp His Thr Tyr Glu Gly Leu Asp Ile Asp Gln Thr Ala Thr Tyr Glu
            195                 200                 205

Asp Ile Val Thr Leu Arg Thr Gly Glu Val Lys Trp Ser Val Gly Glu
    210                 215                 220

His Pro Gly Gln Glu
225

<210> SEQ ID NO 107
<211> LENGTH: 5
```

```
<212> TYPE: PRT
<213> ORGANISM: Artificial Sequence
<220> FEATURE:
<223> OTHER INFORMATION: VH CDR sequence, CDR1

<400> SEQUENCE: 107

Asn Tyr Gly Met Asn
1               5

<210> SEQ ID NO 108
<211> LENGTH: 16
<212> TYPE: PRT
<213> ORGANISM: Artificial Sequence
<220> FEATURE:
<223> OTHER INFORMATION: VH CDR sequence, CDR2

<400> SEQUENCE: 108

Arg Ile Tyr Pro Gly Ser Gly Ser Thr Asn Tyr Gln Lys Phe Lys Gly
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: VL CDR sequence, CDR1

<400> SEQUENCE: 109

Arg Ser Ser Gln Ser Ile Val His Ser Asn Gly Asn Thr Tyr Leu Glu
1               5                   10                  15

<210> SEQ ID NO 110
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 110

Lys Val Ser Asn Arg Pro Ser
1               5

<210> SEQ ID NO 111
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 111

Phe Gln Gly Ser His Val Pro Trp Thr
1               5

<210> SEQ ID NO 112
<211> LENGTH: 5
<212> TYPE: PRT
<213> ORGANISM: Artificial Sequence
<220> FEATURE:
<223> OTHER INFORMATION: glycine-serine linker

<400> SEQUENCE: 112

Gly Gly Gly Gly Ser
1               5

<210> SEQ ID NO 113
<211> LENGTH: 8
<212> TYPE: PRT
```

```
<213> ORGANISM: Artificial Sequence
<220> FEATURE:
<223> OTHER INFORMATION: VH CDR sequence, CDR1

<400> SEQUENCE: 113

Gly Phe Thr Phe Ser Asn Ala Ala
1               5

<210> SEQ ID NO 114
<211> LENGTH: 10
<212> TYPE: PRT
<213> ORGANISM: Artificial Sequence
<220> FEATURE:
<223> OTHER INFORMATION: VH CDR sequence, CDR2

<400> SEQUENCE: 114

Ile Arg Thr Lys Pro Asn Asn Tyr Ala Thr
1               5                   10

<210> SEQ ID NO 115
<211> LENGTH: 12
<212> TYPE: PRT
<213> ORGANISM: Artificial Sequence
<220> FEATURE:
<223> OTHER INFORMATION: VH CDR sequence, CDR3

<400> SEQUENCE: 115

Thr Tyr Tyr Asp Gly Ser Ser Tyr Ala Met Asp Ala
1               5                   10

<210> SEQ ID NO 116
<211> LENGTH: 11
<212> TYPE: PRT
<213> ORGANISM: Artificial Sequence
<220> FEATURE:
<223> OTHER INFORMATION: VL CDR sequence, CDR1

<400> SEQUENCE: 116

Gln Ser Leu Glu Tyr Ser Asp Gly Tyr Thr Tyr
1               5                   10

<210> SEQ ID NO 117
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 117

Phe Gln Ala Thr His Asp Pro Tyr Thr
1               5

<210> SEQ ID NO 118
<211> LENGTH: 121
<212> TYPE: PRT
<213> ORGANISM: Artificial Sequence
<220> FEATURE:
<223> OTHER INFORMATION: VH sequence from 2E8 antibody

<400> SEQUENCE: 118

Ala Val Gln Leu Val Glu Ser Gly Gly Gly Leu Val Gln Pro Lys Glu
1               5                   10                  15

Ser Leu Lys Ile Ser Cys Ala Ala Ser Gly Phe Thr Phe Ser Asn Ala
            20                  25                  30

Ala Met Tyr Trp Val Arg Gln Ala Pro Gly Lys Gly Leu Glu Trp Val
        35                  40                  45
```

```
Ala Arg Ile Arg Thr Lys Pro Asn Asn Tyr Ala Thr Asn Tyr Ala Asp
        50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Thr Glu Asp Thr Ala Met Tyr
                    85                  90                  95

Tyr Cys Thr Tyr Tyr Asp Gly Ser Ser Tyr Ala Met Asp Ala Trp Gly
                100                 105                 110

Gln Gly Thr Ser Val Thr Val Ser Ser
            115                 120

<210> SEQ ID NO 119
<211> LENGTH: 112
<212> TYPE: PRT
<213> ORGANISM: Artificial Sequence
<220> FEATURE:
<223> OTHER INFORMATION: VL sequence from 2E8 antibody

<400> SEQUENCE: 119

Asp Val Val Leu Thr Gln Thr Pro Val Ser Leu Ser Val Thr Leu Gly
1               5                   10                  15

Asp Gln Ala Ser Ile Ser Cys Arg Ser Ser Gln Ser Leu Glu Tyr Ser
                20                  25                  30

Asp Gly Tyr Thr Tyr Leu Asp Trp Tyr Leu Gln Lys Pro Gly Gln Ser
            35                  40                  45

Pro Gln Leu Leu Ile Tyr Glu Val Ser Asn Arg Phe Ser Gly Val Pro
        50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Asp Pro Tyr Thr Phe Gly Ala Gly Thr Lys Leu Glu Ile Lys
                100                 105                 110

<210> SEQ ID NO 120
<211> LENGTH: 250
<212> TYPE: PRT
<213> ORGANISM: Artificial Sequence
<220> FEATURE:
<223> OTHER INFORMATION: 2E8 scFV sequence

<400> SEQUENCE: 120

Asp Val Val Leu Thr Gln Thr Pro Val Ser Leu Ser Val Thr Leu Gly
1               5                   10                  15

Asp Gln Ala Ser Ile Ser Cys Arg Ser Ser Gln Ser Leu Glu Tyr Ser
                20                  25                  30

Asp Gly Tyr Thr Tyr Leu Asp Trp Tyr Leu Gln Lys Pro Gly Gln Ser
            35                  40                  45

Pro Gln Leu Leu Ile Tyr Glu Val Ser Asn Arg Phe Ser Gly Val Pro
        50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Asp Pro Tyr Thr Phe Gly Ala Gly Thr Lys Leu Glu Ile Lys
                100                 105                 110

Arg Ser Gly Gly Gly Gly Ser Gly Gly Gly Gly Ser Gly Gly Gly Gly
```

```
                115                 120                 125
Ser Ala Val Gln Leu Val Glu Ser Gly Gly Gly Leu Val Gln Pro Lys
    130                 135                 140

Glu Ser Leu Lys Ile Ser Cys Ala Ala Ser Gly Phe Thr Phe Ser Asn
145                 150                 155                 160

Ala Ala Met Tyr Trp Val Arg Gln Ala Pro Gly Lys Gly Leu Glu Trp
                165                 170                 175

Val Ala Arg Ile Arg Thr Lys Pro Asn Asn Tyr Ala Thr Asn Tyr Ala
            180                 185                 190

Asp Ser Val Lys Gly Arg Phe Thr Ile Ser Arg Asp Asp Ser Lys Ser
        195                 200                 205

Met Val Tyr Leu Gln Met Asp Asn Leu Lys Thr Glu Asp Thr Ala Met
    210                 215                 220

Tyr Tyr Cys Thr Tyr Tyr Asp Gly Ser Ser Tyr Ala Met Asp Ala Trp
225                 230                 235                 240

Gly Gln Gly Thr Ser Val Thr Val Ser Ser
                245                 250
```

<210> SEQ ID NO 121
<211> LENGTH: 8
<212> TYPE: PRT
<213> ORGANISM: Artificial Sequence
<220> FEATURE:
<223> OTHER INFORMATION: VH CDR sequence, CDR1

<400> SEQUENCE: 121

```
Gly Phe Thr Phe Ser His Thr Ala
1               5
```

<210> SEQ ID NO 122
<211> LENGTH: 10
<212> TYPE: PRT
<213> ORGANISM: Artificial Sequence
<220> FEATURE:
<223> OTHER INFORMATION: VH CDR sequence, CDR2

<400> SEQUENCE: 122

```
Ile Arg Ile Gln Pro Lys Asn Tyr Ala Thr
1               5                   10
```

<210> SEQ ID NO 123
<211> LENGTH: 9
<212> TYPE: PRT
<213> ORGANISM: Artificial Sequence
<220> FEATURE:
<223> OTHER INFORMATION: VH CDR sequence, CDR3

<400> SEQUENCE: 123

```
Thr Ala Ala Gly Phe Gly Phe Asp Tyr
1               5
```

<210> SEQ ID NO 124
<211> LENGTH: 11
<212> TYPE: PRT
<213> ORGANISM: Artificial Sequence
<220> FEATURE:
<223> OTHER INFORMATION: VL CDR sequence, CDR1

<400> SEQUENCE: 124

```
Gln Ser Leu Glu Tyr Ser Asp Gly Asn Thr Tyr
1               5                   10
```

```
<210> SEQ ID NO 125
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 125

Leu Gln Ala Thr His Asp Pro Phe Thr
1               5

<210> SEQ ID NO 126
<211> LENGTH: 118
<212> TYPE: PRT
<213> ORGANISM: Artificial Sequence
<220> FEATURE:
<223> OTHER INFORMATION: VH sequence from 3H2 antibody

<400> SEQUENCE: 126

Ala Val Gln Leu Val Glu Ser Gly Gly Gly Leu Val Gln Pro Lys Glu
1               5                   10                  15

Ser Leu Lys Leu Ser Cys Ala Ala Ser Gly Phe Thr Phe Ser His Thr
                20                  25                  30

Ala Met Tyr Trp Val Arg Gln Ala Pro Gly Lys Gly Leu Glu Cys Val
            35                  40                  45

Ala Arg Ile Arg Ile Gln Pro Lys Asn Tyr Ala Thr Tyr Tyr Ala Asp
        50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Thr Glu Asp Thr Ala Met Tyr
                85                  90                  95

Tyr Cys Thr Ala Ala Gly Phe Gly Phe Asp Tyr Trp Gly Gln Gly Val
            100                 105                 110

Met Val Thr Val Ser Ser
        115

<210> SEQ ID NO 127
<211> LENGTH: 112
<212> TYPE: PRT
<213> ORGANISM: Artificial Sequence
<220> FEATURE:
<223> OTHER INFORMATION: VL sequence from 3H2 antibody

<400> SEQUENCE: 127

Asp Val Val Leu Thr Gln Thr Pro Val Ser Leu Ser Val Thr Leu Gly
1               5                   10                  15

Asp Gln Ala Ser Ile Ser Cys Arg Ser Ser Gln Ser Leu Glu Tyr Ser
                20                  25                  30

Asp Gly Asn Thr Tyr Leu Glu Trp Tyr Leu Gln Lys Pro Gly Gln Ser
            35                  40                  45

Pro Gln Leu Leu Ile Tyr Glu Val Ser Lys Arg Phe Ser Gly Val Pro
        50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Ile Tyr Tyr Cys Leu Gln Ala
                85                  90                  95

Thr His Asp Pro Phe Thr Phe Gly Ser Gly Thr Lys Leu Glu Ile Lys
            100                 105                 110

<210> SEQ ID NO 128
```

```
<211> LENGTH: 247
<212> TYPE: PRT
<213> ORGANISM: Artificial Sequence
<220> FEATURE:
<223> OTHER INFORMATION: 3H2 scFv sequence

<400> SEQUENCE: 128
```

Asp Val Val Leu Thr Gln Thr Pro Val Ser Leu Ser Val Thr Leu Gly
1               5                   10                  15

Asp Gln Ala Ser Ile Ser Cys Arg Ser Ser Gln Ser Leu Glu Tyr Ser
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Glu Val Ser Lys Arg Phe Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Ile Tyr Tyr Cys Leu Gln Ala
                85                  90                  95

Thr His Asp Pro Phe Thr Phe Gly Ser Gly Thr Lys Leu Glu Ile Lys
            100                 105                 110

Arg Ser Gly Gly Gly Gly Ser Gly Gly Gly Ser Gly Gly Gly Gly
        115                 120                 125

Ser Ala Val Gln Leu Val Glu Ser Gly Gly Leu Val Gln Pro Lys
130                 135                 140

Glu Ser Leu Lys Leu Ser Cys Ala Ala Ser Gly Phe Thr Phe Ser His
145                 150                 155                 160

Thr Ala Met Tyr Trp Val Arg Gln Ala Pro Gly Lys Gly Leu Glu Cys
                165                 170                 175

Val Ala Arg Ile Arg Ile Gln Pro Lys Asn Tyr Ala Thr Tyr Tyr Ala
            180                 185                 190

Asp Ser Val Lys Gly Arg Phe Thr Ile Ser Arg Asp Asp Ser Lys Ser
        195                 200                 205

Met Val Tyr Leu Gln Met Asp Asn Leu Lys Thr Glu Asp Thr Ala Met
    210                 215                 220

Tyr Tyr Cys Thr Ala Ala Gly Phe Gly Phe Asp Tyr Trp Gly Gln Gly
225                 230                 235                 240

Val Met Val Thr Val Ser Ser
                245

```
<210> SEQ ID NO 129
<211> LENGTH: 10
<212> TYPE: PRT
<213> ORGANISM: Artificial Sequence
<220> FEATURE:
<223> OTHER INFORMATION: VH CDR sequence, CDR3

<400> SEQUENCE: 129
```

Thr Ala Asp Gly Gly Tyr Gly Phe Asp Tyr
1               5                   10

```
<210> SEQ ID NO 130
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 130
```

```
Phe Gln Gly Thr His Asp Pro Tyr Thr
1               5
```

```
<210> SEQ ID NO 131
<211> LENGTH: 119
<212> TYPE: PRT
<213> ORGANISM: Artificial Sequence
<220> FEATURE:
<223> OTHER INFORMATION: VH sequence from 4G11 antibody

<400> SEQUENCE: 131
```

```
Ala Val Gln Leu Val Glu Ser Gly Gly Gly Leu Val Gln Pro Glu Glu
1               5                   10                  15

Ser Leu Lys Ile Ser Cys Ala Ala Ser Gly Phe Thr Phe Ser Asn Ala
                20                  25                  30

Ala Met Phe Trp Val Arg Gln Ala Pro Gly Lys Gly Leu Glu Trp Ile
            35                  40                  45

Ala Arg Ile Arg Thr Lys Pro Asn Asn Tyr Ala Thr Tyr Tyr Val Asp
        50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Thr Glu Asp Thr Ala Met Tyr
                85                  90                  95

Tyr Cys Thr Ala Asp Gly Gly Tyr Gly Phe Asp Tyr Trp Gly Gln Gly
            100                 105                 110

Val Met Val Thr Val Ser Ser
        115
```

```
<210> SEQ ID NO 132
<211> LENGTH: 112
<212> TYPE: PRT
<213> ORGANISM: Artificial Sequence
<220> FEATURE:
<223> OTHER INFORMATION: VL sequence from 4G11 antibody

<400> SEQUENCE: 132
```

```
Asp Val Val Leu Thr Gln Thr Pro Val Ser Leu Ser Val Thr Leu Gly
1               5                   10                  15

Asp Gln Ala Ser Ile Ser Cys Arg Ser Gln Ser Leu Glu Tyr Ser
                20                  25                  30

Asp Gly Tyr Thr Tyr Leu Glu Trp Tyr Leu Gln Lys Pro Gly Gln Ser
            35                  40                  45

Pro Gln Leu Leu Ile Tyr Glu Val Ser Asn Arg Phe Ser Gly Val Pro
        50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Leu Tyr Tyr Cys Phe Gln Gly
                85                  90                  95

Thr His Asp Pro Tyr Thr Phe Gly Ala Gly Thr Lys Leu Glu Ile Lys
            100                 105                 110
```

```
<210> SEQ ID NO 133
<211> LENGTH: 248
<212> TYPE: PRT
<213> ORGANISM: Artificial Sequence
<220> FEATURE:
<223> OTHER INFORMATION: 4G11 scFv sequence

<400> SEQUENCE: 133
```

```
Asp Val Val Leu Thr Gln Thr Pro Val Ser Leu Ser Val Thr Leu Gly
```

```
  1               5                  10                 15
Asp Gln Ala Ser Ile Ser Cys Arg Ser Ser Gln Ser Leu Glu Tyr Ser
                20                 25                 30

Asp Gly Tyr Thr Tyr Leu Glu Trp Tyr Leu Gln Lys Pro Gly Gln Ser
                35                 40                 45

Pro Gln Leu Leu Ile Tyr Glu Val Ser Asn Arg Phe Ser Gly Val Pro
        50                 55                 60

Asp Arg Phe Ile Gly Ser Gly Ser Gly Thr Asp Phe Thr Leu Lys Ile
65                  70                 75                 80

Ser Arg Val Glu Pro Glu Asp Leu Gly Leu Tyr Tyr Cys Phe Gln Gly
                85                 90                 95

Thr His Asp Pro Tyr Thr Phe Gly Ala Gly Thr Lys Leu Glu Ile Lys
                100                105                110

Arg Ser Gly Gly Gly Gly Ser Gly Gly Gly Ser Gly Gly Gly Gly
                115                120                125

Ser Ala Val Gln Leu Val Glu Ser Gly Gly Leu Val Gln Pro Glu
        130                135                140

Glu Ser Leu Lys Ile Ser Cys Ala Ala Ser Gly Phe Thr Phe Ser Asn
145                 150                155                160

Ala Ala Met Phe Trp Val Arg Gln Ala Pro Gly Lys Gly Leu Glu Trp
                165                170                175

Ile Ala Arg Ile Arg Thr Lys Pro Asn Asn Tyr Ala Thr Tyr Tyr Val
                180                185                190

Asp Ser Val Lys Gly Arg Phe Thr Ile Ser Arg Asp Asp Ser Lys Ser
                195                200                205

Met Val Tyr Leu Gln Met Asp Asn Leu Lys Thr Glu Asp Thr Ala Met
        210                215                220

Tyr Tyr Cys Thr Ala Asp Gly Gly Tyr Gly Phe Asp Tyr Trp Gly Gln
225                 230                235                240

Gly Val Met Val Thr Val Ser Ser
                245

<210> SEQ ID NO 134
<211> LENGTH: 112
<212> TYPE: PRT
<213> ORGANISM: Artificial Sequence
<220> FEATURE:
<223> OTHER INFORMATION: VL sequence from 7G4 antibody

<400> SEQUENCE: 134

Asp Val Val Leu Thr Gln Thr Pro Val Ser Leu Ser Val Thr Leu Gly
1               5                  10                 15

Asp Gln Ala Ser Ile Ser Cys Arg Ser Ser Gln Ser Leu Glu Tyr Ser
                20                 25                 30

Asp Gly Tyr Thr Tyr Leu Asp Trp Tyr Leu Gln Lys Pro Gly Gln Ser
                35                 40                 45

Pro Gln Leu Leu Ile Tyr Glu Ile Ser Asn Arg Phe Ser Gly Val Pro
        50                 55                 60

Asp Arg Phe Ile Gly Ser Gly Ser Gly Thr Asp Phe Thr Leu Lys Ile
65                  70                 75                 80

Ser Arg Val Glu Pro Glu Asp Leu Gly Val Tyr Tyr Cys Phe Gln Ala
                85                 90                 95

Thr His Asp Pro Tyr Thr Phe Gly Ala Gly Thr Lys Leu Glu Ile Lys
                100                105                110
```

```
<210> SEQ ID NO 135
<211> LENGTH: 250
<212> TYPE: PRT
<213> ORGANISM: Artificial Sequence
<220> FEATURE:
<223> OTHER INFORMATION: 7G4 scFv sequence

<400> SEQUENCE: 135

Asp Val Val Leu Thr Gln Thr Pro Val Ser Leu Ser Val Thr Leu Gly
1               5                   10                  15

Asp Gln Ala Ser Ile Ser Cys Arg Ser Ser Gln Ser Leu Glu Tyr Ser
            20                  25                  30

Asp Gly Tyr Thr Tyr Leu Asp Trp Tyr Leu Gln Lys Pro Gly Gln Ser
        35                  40                  45

Pro Gln Leu Leu Ile Tyr Glu Ile Ser Asn Arg Phe Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Asp Pro Tyr Thr Phe Gly Ala Gly Thr Lys Leu Glu Ile Lys
            100                 105                 110

Arg Ser Gly Gly Gly Gly Ser Gly Gly Gly Ser Gly Gly Gly Gly
        115                 120                 125

Ser Ala Val Gln Leu Val Glu Ser Gly Gly Gly Leu Val Gln Pro Lys
    130                 135                 140

Glu Ser Leu Lys Ile Ser Cys Ala Ala Ser Gly Phe Thr Phe Ser Asn
145                 150                 155                 160

Ala Ala Met Tyr Trp Val Arg Gln Ala Pro Gly Lys Gly Leu Glu Trp
                165                 170                 175

Val Ala Arg Ile Arg Thr Lys Pro Asn Asn Tyr Ala Thr Asn Tyr Ala
            180                 185                 190

Asp Ser Val Lys Gly Arg Phe Thr Ile Ser Arg Asp Asp Ser Lys Ser
        195                 200                 205

Met Val Tyr Leu Gln Met Asp Asn Leu Lys Thr Glu Asp Thr Ala Met
210                 215                 220

Tyr Tyr Cys Thr Tyr Tyr Asp Gly Ser Ser Tyr Ala Met Asp Ala Trp
225                 230                 235                 240

Gly Gln Gly Thr Ser Val Thr Val Ser Ser
                245                 250

<210> SEQ ID NO 136
<211> LENGTH: 8
<212> TYPE: PRT
<213> ORGANISM: Artificial Sequence
<220> FEATURE:
<223> OTHER INFORMATION: VH CDR sequence, CDR1

<400> SEQUENCE: 136

Gly Phe Thr Phe Ser Asn Thr Ala
1               5

<210> SEQ ID NO 137
<211> LENGTH: 11
<212> TYPE: PRT
<213> ORGANISM: Artificial Sequence
<220> FEATURE:
<223> OTHER INFORMATION: VL CDR sequence, CDR1

<400> SEQUENCE: 137
```

```
Gln Arg Leu Glu Tyr Ser Asp Gly Asn Thr Tyr
1               5                   10

<210> SEQ ID NO 138
<211> LENGTH: 118
<212> TYPE: PRT
<213> ORGANISM: Artificial Sequence
<220> FEATURE:
<223> OTHER INFORMATION: VH sequence from 9F1 antibody

<400> SEQUENCE: 138

Ala Val Gln Leu Val Glu Ser Gly Gly Gly Leu Val Arg Pro Lys Glu
1               5                   10                  15

Ser Leu Lys Ile Ser Cys Ala Ala Ser Gly Phe Thr Phe Ser Asn Thr
            20                  25                  30

Ala Met Tyr Trp Val Arg Gln Ala Pro Gly Lys Gly Leu Glu Cys Val
        35                  40                  45

Ala Arg Ile Arg Ile Gln Pro Lys Asn Tyr Ala Thr Phe Tyr Ala Asp
    50                  55                  60

Ser Val Lys Gly Arg Phe Thr Ile Ser Arg Asp Asp Ser Lys Ser Met
65                  70                  75                  80

Val Tyr Leu Arg Met Asp Asn Leu Lys Thr Glu Asp Thr Ala Met Tyr
                85                  90                  95

Tyr Cys Thr Ala Ala Gly Phe Gly Phe Asp Tyr Trp Gly Gln Gly Val
            100                 105                 110

Met Val Thr Val Ser Ser
        115

<210> SEQ ID NO 139
<211> LENGTH: 112
<212> TYPE: PRT
<213> ORGANISM: Artificial Sequence
<220> FEATURE:
<223> OTHER INFORMATION: VL sequence from 9F1 antibody

<400> SEQUENCE: 139

Asp Val Val Leu Thr Gln Thr Pro Val Ser Leu Ser Val Thr Leu Gly
1               5                   10                  15

Asp Gln Ala Ser Ile Ser Cys Arg Ser Ser Gln Arg Leu Glu Tyr Ser
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Glu Val Ser Glu Arg Phe Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Leu Gln Ala
                85                  90                  95

Thr His Asp Pro Phe Thr Phe Gly Ser Gly Thr Lys Leu Glu Ile Lys
            100                 105                 110

<210> SEQ ID NO 140
<211> LENGTH: 247
<212> TYPE: PRT
<213> ORGANISM: Artificial Sequence
<220> FEATURE:
<223> OTHER INFORMATION: 9F1 scFv sequence

<400> SEQUENCE: 140
```

```
Asp Val Val Leu Thr Gln Thr Pro Val Ser Leu Ser Val Thr Leu Gly
1               5                   10                  15

Asp Gln Ala Ser Ile Ser Cys Arg Ser Ser Gln Arg Leu Glu Tyr Ser
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Glu Val Ser Glu Arg Phe Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Leu Gln Ala
                85                  90                  95

Thr His Asp Pro Phe Thr Phe Gly Ser Gly Thr Lys Leu Glu Ile Lys
                100                 105                 110

Arg Ser Gly Gly Gly Ser Gly Gly Gly Ser Gly Gly Gly Gly
                115                 120                 125

Ser Ala Val Gln Leu Val Glu Ser Gly Gly Leu Val Arg Pro Lys
    130                 135                 140

Glu Ser Leu Lys Ile Ser Cys Ala Ala Ser Gly Phe Thr Phe Ser Asn
145                 150                 155                 160

Thr Ala Met Tyr Trp Val Arg Gln Ala Pro Gly Lys Gly Leu Glu Cys
                165                 170                 175

Val Ala Arg Ile Arg Ile Gln Pro Lys Asn Tyr Ala Thr Phe Tyr Ala
                180                 185                 190

Asp Ser Val Lys Gly Arg Phe Thr Ile Ser Arg Asp Asp Ser Lys Ser
                195                 200                 205

Met Val Tyr Leu Arg Met Asp Asn Leu Lys Thr Glu Asp Thr Ala Met
    210                 215                 220

Tyr Tyr Cys Thr Ala Ala Gly Phe Gly Phe Asp Tyr Trp Gly Gln Gly
225                 230                 235                 240

Val Met Val Thr Val Ser Ser
                245

<210> SEQ ID NO 141
<211> LENGTH: 8
<212> TYPE: PRT
<213> ORGANISM: Artificial Sequence
<220> FEATURE:
<223> OTHER INFORMATION: VH CDR sequence, CDR1

<400> SEQUENCE: 141

Gly Phe Thr Phe Ser Ser Ala Ala
1               5

<210> SEQ ID NO 142
<211> LENGTH: 121
<212> TYPE: PRT
<213> ORGANISM: Artificial Sequence
<220> FEATURE:
<223> OTHER INFORMATION: VH sequence from 10C11 antibody

<400> SEQUENCE: 142

Ala Val Gln Phe Val Glu Ser Gly Gly Gly Leu Val Gln Pro Lys Glu
1               5                   10                  15

Ser Leu Lys Ile Ser Cys Ala Ala Ser Gly Phe Thr Phe Ser Ser Ala
            20                  25                  30

Ala Met Tyr Trp Val Arg Gln Ala Pro Gly Lys Gly Leu Glu Trp Leu
            35                  40                  45
```

```
Ala Arg Ile Arg Thr Lys Pro Asn Asn Tyr Ala Thr Asn Tyr Ala Asp
     50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Thr Glu Asp Ser Ala Met Tyr
                 85                  90                  95

Tyr Cys Thr Tyr Tyr Asp Gly Ser Ser Tyr Ala Met Asp Ala Trp Gly
                100                 105                 110

Gln Gly Thr Ser Val Thr Val Ser Ser
            115                 120

<210> SEQ ID NO 143
<211> LENGTH: 112
<212> TYPE: PRT
<213> ORGANISM: Artificial Sequence
<220> FEATURE:
<223> OTHER INFORMATION: VL sequence from 10C11 antibody

<400> SEQUENCE: 143

Asp Val Val Leu Thr Gln Thr Pro Val Ser Leu Ser Val Thr Leu Gly
1               5                  10                  15

Asp Gln Ala Ser Ile Ser Cys Arg Ser Ser Gln Ser Leu Glu Tyr Ser
                20                  25                  30

Asp Gly Tyr Thr Tyr Leu Asp Trp Tyr Leu Gln Lys Pro Gly Gln Ser
            35                  40                  45

Pro Gln Leu Leu Ile Ser Glu Val Ser Asn Arg Phe Ser Gly Val Pro
        50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Asp Pro Tyr Thr Phe Gly Ala Gly Thr Lys Leu Glu Ile Lys
                100                 105                 110

<210> SEQ ID NO 144
<211> LENGTH: 250
<212> TYPE: PRT
<213> ORGANISM: Artificial Sequence
<220> FEATURE:
<223> OTHER INFORMATION: 10C11 scFv sequence

<400> SEQUENCE: 144

Asp Val Val Leu Thr Gln Thr Pro Val Ser Leu Ser Val Thr Leu Gly
1               5                  10                  15

Asp Gln Ala Ser Ile Ser Cys Arg Ser Ser Gln Ser Leu Glu Tyr Ser
                20                  25                  30

Asp Gly Tyr Thr Tyr Leu Asp Trp Tyr Leu Gln Lys Pro Gly Gln Ser
            35                  40                  45

Pro Gln Leu Leu Ile Ser Glu Val Ser Asn Arg Phe Ser Gly Val Pro
        50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Asp Pro Tyr Thr Phe Gly Ala Gly Thr Lys Leu Glu Ile Lys
                100                 105                 110

Arg Ser Gly Gly Gly Gly Ser Gly Gly Gly Gly Ser Gly Gly Gly Gly
```

```
              115                 120                 125
Ser Ala Val Gln Phe Val Glu Ser Gly Gly Gly Leu Val Gln Pro Lys
        130                 135                 140

Glu Ser Leu Lys Ile Ser Cys Ala Ala Ser Gly Phe Thr Phe Ser Ser
145                 150                 155                 160

Ala Ala Met Tyr Trp Val Arg Gln Ala Pro Gly Lys Gly Leu Glu Trp
                165                 170                 175

Leu Ala Arg Ile Arg Thr Lys Pro Asn Asn Tyr Ala Thr Asn Tyr Ala
            180                 185                 190

Asp Ser Val Lys Gly Arg Phe Thr Ile Ser Arg Asp Asp Ser Lys Ser
        195                 200                 205

Met Val Tyr Leu Gln Met Asp Asn Leu Lys Thr Glu Asp Ser Ala Met
    210                 215                 220

Tyr Tyr Cys Thr Tyr Tyr Asp Gly Ser Ser Tyr Ala Met Asp Ala Trp
225                 230                 235                 240

Gly Gln Gly Thr Ser Val Thr Val Ser Ser
                245                 250

<210> SEQ ID NO 145
<211> LENGTH: 111
<212> TYPE: PRT
<213> ORGANISM: Homo sapiens

<400> SEQUENCE: 145

Leu Trp Met His Lys Val Pro Ala Ser Leu Met Val Ser Leu Gly Glu
1               5                   10                  15

Asp Ala His Phe Gln Cys Pro His Asn Ser Ser Asn Asn Ala Asn Val
                20                  25                  30

Thr Trp Trp Arg Val Leu His Gly Asn Tyr Thr Trp Pro Pro Glu Phe
            35                  40                  45

Leu Gly Pro Gly Glu Asp Pro Asn Gly Thr Leu Ile Ile Gln Asn Val
        50                  55                  60

Asn Lys Ser His Gly Gly Ile Tyr Val Cys Arg Val Gln Glu Gly Asn
65                  70                  75                  80

Glu Ser Tyr Gln Gln Ser Cys Gly Thr Tyr Leu Arg Val Arg Gln Pro
                85                  90                  95

Pro Pro Arg Pro Phe Leu Asp Met Gly Glu Gly Thr Lys Asn Arg
            100                 105                 110

<210> SEQ ID NO 146
<211> LENGTH: 131
<212> TYPE: PRT
<213> ORGANISM: Homo sapiens

<400> SEQUENCE: 146

Ala Arg Ser Glu Asp Arg Tyr Arg Asn Pro Lys Gly Ser Ala Cys Ser
1               5                   10                  15

Arg Ile Trp Gln Ser Pro Arg Phe Ile Ala Arg Lys Gly Phe Thr
                20                  25                  30

Val Lys Met His Cys Tyr Met Asn Ser Ala Ser Gly Asn Val Ser Trp
            35                  40                  45

Leu Trp Lys Gln Glu Met Asp Glu Asn Pro Gln Gln Leu Lys Leu Glu
        50                  55                  60

Lys Gly Arg Met Glu Glu Ser Gln Asn Glu Ser Leu Ala Thr Leu Thr
65                  70                  75                  80

Ile Gln Gly Ile Arg Phe Glu Asp Asn Gly Ile Tyr Phe Cys Gln Gln
```

```
                85                  90                  95
Lys Cys Asn Asn Thr Ser Glu Val Tyr Gln Gly Cys Gly Thr Glu Leu
            100                 105                 110

Arg Val Met Gly Phe Ser Thr Leu Ala Gln Leu Lys Gln Arg Asn Thr
        115                 120                 125

Leu Lys Asp
    130

<210> SEQ ID NO 147
<211> LENGTH: 124
<212> TYPE: PRT
<213> ORGANISM: Artificial Sequence
<220> FEATURE:
<223> OTHER INFORMATION: VH sequence from 1G3-4 antibody

<400> SEQUENCE: 147

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Thr Asn Ile Trp Trp Asp Asp Lys Tyr Asn Pro Ser
    50                  55                  60

Leu Lys Asn Arg Leu Thr Ile Ser Lys Asp Thr Ser Ile Asn Gln Ala
65                  70                  75                  80

Phe Leu Lys Ile Thr Asn Val Asp Thr Ala Asp Ala Thr Tyr Tyr
                85                  90                  95

Cys Ala Arg Ile Ala His Tyr Phe Asp Gly Tyr Tyr Val Met Asp
            100                 105                 110

Val Trp Gly Gln Gly Thr Ser Val Thr Val Ser Ser
        115                 120

<210> SEQ ID NO 148
<211> LENGTH: 107
<212> TYPE: PRT
<213> ORGANISM: Artificial Sequence
<220> FEATURE:
<223> OTHER INFORMATION: VL sequence from 1G3-4 antibody

<400> SEQUENCE: 148

Asp Ile Gln Met Thr Gln Ser Pro Ala Ser Leu Ser Ala Ser Leu Gly
1               5                   10                  15

Glu Thr Val Ser Ile Glu Cys Leu Ala Ser Gly Gly Ile Ser Asn Asp
            20                  25                  30

Leu Ala Trp Tyr Gln Gln Lys Ser Gly Lys Ser Pro Gln Leu Leu Ile
        35                  40                  45

Tyr Ala Ala Ser Arg Leu Gln Asp Gly Val Pro Ser Arg Phe Ser Gly
        50                  55                  60

Ser Gly Ser Gly Thr Arg Tyr Ser Leu Lys Ile Ser Gly Met Gln Ser
65                  70                  75                  80

Glu Asp Glu Ala Asp Tyr Phe Cys Gln Gln Ser Tyr Lys Tyr Pro Tyr
                85                  90                  95

Thr Phe Gly Gly Gly Thr Lys Leu Glu Leu Lys
            100                 105
```